US008323621B2

(12) United States Patent
Bornhop et al.

(10) Patent No.: US 8,323,621 B2
(45) Date of Patent: *Dec. 4, 2012

(54) MULTI-USE MULTIMODAL IMAGING CHELATES

(75) Inventors: Darryl J. Bornhop, Nashville, TN (US); H. Charles Manning, Nashville, TN (US); Timothy Goebel, Lubbock, TX (US)

(73) Assignees: Vanderbilt University, Nashville, TN (US); Texas Tech University System, Lubbock, TX (US)

( * ) Notice: Subject to any disclaimer, the term of this patent is extended or adjusted under 35 U.S.C. 154(b) by 899 days.

This patent is subject to a terminal disclaimer.

(21) Appl. No.: 12/042,281

(22) Filed: Mar. 4, 2008

(65) Prior Publication Data

US 2008/0241074 A1  Oct. 2, 2008

Related U.S. Application Data

(63) Continuation-in-part of application No. 10/233,672, filed on Sep. 4, 2002, now Pat. No. 7,338,651.

(60) Provisional application No. 60/316,284, filed on Sep. 4, 2001, provisional application No. 60/316,303, filed on Sep. 4, 2001.

(51) Int. Cl.
 *A61B 5/00* (2006.01)
 *A61B 5/055* (2006.01)
 *C07D 255/02* (2006.01)
 *C07F 5/00* (2006.01)

(52) U.S. Cl. ...... 424/9.6; 424/9.3; 424/9.32; 424/9.322; 424/9.36; 424/9.361; 424/9.363; 424/9.364; 424/9.365; 540/474; 534/11; 534/16

(58) Field of Classification Search ................. 424/9.3, 424/9.36, 9.361, 9.364, 9.365, 9.6, 9.32, 424/9.322, 9.631, 9.363; 540/474; 534/11, 534/16

See application file for complete search history.

(56) References Cited

U.S. PATENT DOCUMENTS

| | | | |
|---|---|---|---|
| 5,531,978 A | 7/1996 | Berg et al. | |
| 5,622,821 A * | 4/1997 | Selvin et al. | ................. 435/6.11 |
| 5,630,997 A | 5/1997 | Sherry et al. | |
| 5,928,627 A | 7/1999 | Kiefer | |
| 5,998,624 A | 12/1999 | Goodman et al. | |
| 7,338,651 B2 | 4/2008 | Bornhop et al. | |
| 7,754,884 B2 | 7/2010 | Bornhop et al. | |
| 2003/0129579 A1* | 7/2003 | Bornhop et al. | ................. 435/4 |
| 2008/0031823 A1 | 2/2008 | Bornhop et al. | |
| 2008/0241074 A1 | 10/2008 | Bornhop et al. | |
| 2008/0241873 A1 | 10/2008 | Bornhop et al. | |
| 2009/0105128 A1 | 4/2009 | Bornhop et al. | |
| 2010/0278739 A1 | 11/2010 | Bornhop et al. | |
| 2010/0324130 A1 | 12/2010 | Bornhop et al. | |

FOREIGN PATENT DOCUMENTS

| | | |
|---|---|---|
| AU | 2002323528 | 3/2008 |
| CA | 2459724 | 2/2011 |
| EP | 1429783 | 6/2004 |
| EP | 1841466 | 10/2007 |
| WO | WO 89/01476 | 2/1989 |
| WO | WO 95/01346 | 1/1995 |
| WO | WO 99/25389 | 5/1999 |
| WO | WO03020701 | 3/2003 |
| WO | WO2006074129 | 7/2006 |

OTHER PUBLICATIONS

Baykal, et al.; Synthesis and Phosphodiester Transesterification Activity of the La3+-Complex of a Novel Functionalized Octadentate Ligand; Tetrahedron Letters; 1998; 39; pp. 5861-5864.
Bornhop, "Simple, high yielding synthesis of trifunctional fluorescent lanthanide chelates," Tetrahedron Letters, Elsevier Science Ltd., (2001).
Chappell, et al.; Synthesis, Characterization, and Evaluation of a Novel Bifunctional Chelating Agents for the Lead Isotopes 203Pb and 212Pb; Nuclear Medicine & Biology; 2000; vol. 27; pp. 93-100.
Geraldes, et al.; Relaxometry, Animal Biodistribution, and Magnetic Resonance Imaging Studies of Some New Gadolinium (III) Macrocyclic Phosphinate and Phosphonate Monoester Complexes; Academic Press; 1993; vol. 30, No. 6; pp. 696-703.
Griffin, et al.; Simple, High Yielding Synthesis of Trifunctional Fluorescent Lanthanide Chelates; Tetrahedron Letters; 2001. Huber, "Fluorescently Detectable Magnetic Resonance Imaging Agents," Bioconjugate Chem., American Chemical Society, vol. 9 (No. 2), p. 242-249, (1998).
Kozikowski, "Wynthesis and Biology of a 7-Nitro-2,1,3-benzoxadiazol-4-yl Derivative of 2-Phenylindole-3-acetamide: A Fluorescent Probe for the Peripheral-Type Benzodiazepine Receptor," Journal of Medicinal Chemistry, American Chemical Society, vol. 40 (No. 16), (Aug. 1, 1997).
Manning, et al.; Facile, Efficient Conjugation of a Trifunctional Lanthanide Chelate to a Peripheral Benzodiazepine Receptor Ligand; Organic Letters; 2002; vol. 4, No. 7; pp. 1075-1078.

* cited by examiner

*Primary Examiner* — Michael G Hartley
*Assistant Examiner* — Leah Schlientz
(74) *Attorney, Agent, or Firm* — Stites & Harbison PLLC; Richard S. Myers, Jr.

(57) ABSTRACT

Cyclen-based chelates can be used as contrast agents for multi-modal imaging of tissue cells. The cyclen-based chelates are preferably polyazamacrocyclic molecules formed from 1,4,7,10 tetraazacyclododecane ("cyclen") having varying chelating ions, phosphoester chains, and light harvesting moieties. By changing the chelating ion, phosphoester chain length and/or the light harvesting moiety different imaging techniques, such as MRI, CT, fluorescence and absorption, x-ray and NIR, may be employed to image the tissue cells. Additionally, the cyclen-based chelates may be conjugated to provide for site-specific delivery of the cyclen-based chelate to the desired tissue cells. The cyclen-based chelates may also be delivered to the tissue cells by attaching the cyclen-based to a polymeric delivery vehicle. Although these cyclen-based chelates have a wide variety of application, the preferred use is for imaging of cancer cells, such as brain cancer, for improving resection of a cancerous tissue.

18 Claims, 11 Drawing Sheets

Gd agent: $5.94 s^{-1} mM^{-1}$
Magnevist: $6.45 s^{-1} mM^{-1}$

MULTI-USE MULTIMODAL IMAGING CHELATES

CROSS REFERENCE TO RELATED APPLICATION

This application is a continuation-in-part of U.S. Pat. No. 7,338,651, filed Sep. 4, 2002, which claims benefit of U.S. Provisional Application Nos. 60/316,284 and 60/316,303, both filed Sep. 4, 2001. All of the prior applications are incorporated herein by reference in their entirety.

BACKGROUND OF THE INVENTION

1. Field of the Invention

The present invention relates generally to the formation of contrast agents containing cyclen-based chelates in order to produce multimodal images of a sample of cells.

2. Background Information

The American Cancer Society estimates that 16,800 new intracranial tumors were diagnosed in 1999, more than double the number of diagnosed cases of Hodgkin's disease, and over half the number of cases of melanoma. Moreover, in the same year, primary cancer of the central nervous system was the cause of death in approximately 13,100 people. Despite aggressive treatment strategies including surgical resection, irradiation and chemotherapy, most patients die from the disease, with median survival measured in months.

Patients with malignant gliomas 18-44 years old have a median survival rate of 107 weeks, whereas patients older than 65 survive just 23 weeks on average. Age, history of previous low-grade tumor, histologic composition of the tumor and treatments (i.e. radiation, surgery and chemotherapy) all affect prognosis. Yet, it is impossible to over-emphasize the importance imaging and detection techniques play in influencing the success in treating a variety of cancers.

Surgical therapy plays an important role in determining outcome for patients with primary brain tumors and other cancerous tumors. Gross total resection is associated with both longer survival and improved neurologic function. Therefore, every effort is made to remove as much of the tumor as possible. The degree to which a complete resection can be carried out in the brain is limited, however, by a number of factors unique to the central nervous system. One variable that directly influences the extent of resection is the difficulty of visually detecting differences between normal brain tissue and malignant tissue. Primary brain tumors are infiltrating lesions and the margins of the tumor are indistinct. For this reason, patients with malignant intrinsic brain tumors often undergo subtotal resection. Alternatively, patients may experience unexpected neurological morbidity if the resection is inadvertently carried into normal surrounding brain tissue. Additionally, current tumor imaging methods are limited because they image the tumor indirectly. Normally, imaging methods measure alterations in blood brain barrier permeability, detect edema or use non-specific MRI signal changes within the tumor and adjacent the brain. Thus it is difficult to identify radiation necrosis and inflammatory changes, as well as to assess response to therapy or to provide the capability of following disease progression. Furthermore, classical MRI contrast enhanced imaging fails to demarcate primary infiltrating glial tumors, with scans often indicating a discreet lesion border even though tumor cells typically extend several centimeters away. Because outcome is so closely linked to the extent of surgical resection, and the degree of resection is limited by difficulties in visually detecting tumors, there is a pressing need to develop new strategies to aid in intraoperative detection and imaging of brain cancer.

The ideal imaging method for enhancing brain cancer detection would be tumor specific, non-invasive, provide real time intraoperative imaging and correlation with anatomic imaging (MRI), and define infiltrating tumor margins.

In patients where computed tomography (CT) or magnetic resonance imaging (MRI) are used to aid in providing "complete" resection of the tumor, the median survival period is 70 weeks. However, patients who undergo "only biopsy of the tumor" have a median survival rate of just 19 weeks. Even with this dramatic improvement, MRI and CT scans cannot be used to identify the outermost border of the malignant brain tumor. It has been repeatedly shown that areas that appear "normal" during surgery contain tumor cells. While contrast enhanced MRI scans often suggest the presence of a discreet border to the lesion, brain tumors are widely infiltrative with tumor cells typically extending microscopically several centimeters away from the obvious area of the disease. Current imaging methods do not adequately assess the extent of disease or differentiate between viable tumor infiltration, radiation necrosis, or inflammatory changes. For these reasons, current imaging modalities are not ideal for following disease progression or assessing response to therapy. If it were possible to perform guided resection using a fluorescent contrast agent to image brain cancer cells on a microscopic scale in the operating room in combination with macroscopic scale MRI, the long-term survival rate would significantly improve.

Recent discoveries in molecular imaging play a vital role in the early detection, diagnosis, and treatment of disease, as well as in the study of biological and biochemical mechanisms, immunology, and neuroscience. Since current molecular-level technologies primarily focus on in-vitro methods, it is crucial to develop imaging methodologies that have high spatial and temporal resolution in-vivo and spectroscopy techniques for imaging at the cellular or molecular scales. Presently, in-vivo detection and surgical resection means are limited to either macroscopic gross visualization, white-light endoscopy or white-light microscopic visualization. The visual assessment of any tissue depends on many factors, including the experience of the clinician, his/her ability to identify the suspect lesions and their resection or biopsy skill. The visual cues, such as signal to noise ratio (S/N), for the determination of a pathologic state are small or low, especially for brain cancer which tends to infiltrate normal tissue. When the contrast for disease is low as it is for small foci of cancer cells, it makes surgical resection problematic. These techniques tend to miss disease at its earliest stage because of low concentrations of the endogenous chromophores leading to contrast between normal tissue and disease. The need for better contrast agents to assist in identifying disease is not limited to the brain. For example, patients undergoing back-to-back colonoscopies, performed by an experienced colonoscopist, may have as many as 15% to 24% of their neoplastic polyps smaller than 1 cm overlooked. Furthermore, up to 6% of larger polyps may escape detection as well. In short, clinical outcomes are dependent on the design of new contrast agents and imaging methodologies. Clearly, there is a significant need for the enhancement of disease detection to improve the clinical outcomes.

Recent advances in optical imaging, high spatial resolution MR, and nuclear imaging play an important role in obtaining molecular information. Early-stage disease detection, evaluation of molecular markers for therapy assessment, and imaging of gene expression or protein levels are just a few of the applications immediately available. High-affinity ligands developed rationally, combinatorially, or by chance must have the ability to reach the intended target at sufficient concentration and for a sufficient length of time to be detectable in-vivo. Through the use of compounds with multiple signatures, this goal is more readily achieved.

Although MRI remains the hallmark imaging modality for examining many types of cancers, MRI does not provide a clinician with real-time intra-operative maps once surgery commences. Thus, new MR contrast agents that can also offer real time intra-operative fluorescence visualization of disease need to be developed in order to take full advantage of conventional MRI examination. While there are numerous exogenous, topical or injectable agents being used to aid in the demarcating of normal tissue from disease tissue, including acetic acid, indocyanine green (ICG), methylene and toluidine blue, and 5-aminolevulinic acid (ALA), none of these agents can be used as an MRI agent. These agents are also restricted in use due to tissue toxicity, low specificity, and/or long manifestation times, with contrast primarily based on differential permeability of the agent between normal and diseased tissue. Generally they provide only modest diagnostic utility, primarily because of an inherent lack of specificity.

Several research groups have investigated laser-induced fluorescence spectroscopy (LIFS) of endogenous fluorophores as a potential tool for tissue diagnostics, targeting cardiovascular and oncological applications. Pertinent reviews in the field of Laser-Induced Fluorescence Spectroscopy (LIFS) for tissue diagnostic applications, and in particular, oncological applications have been presented. Evidence exists that tissue staging can be accomplished allowing transformation from dysplasia to cancer to be quantified. All tissue contains fluorophores or endogenous chromophores that absorb light and subsequently emit light at a longer wavelength. Nicotinamide adenine dinucleotide (NAD[H]), flavins, collagen, and elastin are commonly known tissue fluorophores. It is currently believed that autofluorescence primarily detects changes in concentration or distribution of these components. As normal tissue becomes dysplastic the concentration or distribution of these endogenous fluorophores changes thus leading to a detectable change in the resulting fluorescent spectrum. These changes are wavelength dependent and correlate with changes in histology. These techniques, while showing great promise, still suffer from relatively low S/N stemming from small changes in concentration of the solutes detected in early disease and the large background arising from other fluorophores, scattering, and reflected light. Combining these technical advances with new contrast agents will advance the field of molecular imaging.

Moreover, while steady-state LIFS techniques have been extensively investigated and are currently routinely used in research clinics for characterization of endogenous and exogenous fluorescence, only a few research groups have explored the TR-LIFS techniques for diagnostics. In this regard, both time- and frequency-domain time-resolved instrumentation have been employed. This early work suggests that time-resolved fluorescence spectroscopy improves the specificity of fluorescence measurements in tissue and enhances the ability of LIFS to characterize tissue composition. The use of time-resolved fluorescence approach for tissue characterization is suitable for several reasons. Time-resolved fluorescence measurement a) can resolve the spectral overlap of endogenous fluorophores in tissue (main limitation of LIFS steady-state), b) is independent of fluorescence emission intensity as long as the signal to noise is commensurable, thus independent to the presence of the endogenous chromophores in tissue (hemoglobin) or to excitation-collection geometry (optical assembly), and c) is sensitive to microenvironmental parameters in tissue (pH, enzymatic activity, temperature), thus various tissue parameters can be monitored. Cellular level detection and evaluation of glioma could be facilitated by combining the power of time-resolved spectroscopic imaging with contrast agents.

Another example of contrast enhancement agents or site-directed chemical agents that have seen recent success is the PhotoDynamic Therapy (PDT) class of markers. While these types of markers have shown promise in a diagnostic setting, there are limitations. Long delays for accumulation in tumors, prolonged photosensitization of skin, and phototoxicity of tissues being imaged are some examples of these limitations. Preclinical studies in rat brain-tumor model with hematoporphyrin derivative (HpD) demonstrated an increase in the HpD fluorescence in the brain tumor relative to the adjacent normal tissue. Second generation photosensitizers such as chloroaluminium phthalocyanine have been shown to increase the accuracy with which rat brain tumor margins can be defined during resection in-vivo. More recently, 5-Aminolevulinic acid-(ALA) induced porphyrin (PpIX) fluorescence has been used in clinical studies. The results suggest that ALA-induced PpIX may label malignant gliomas and enhance the tumor removal. However, to date, their efficiency in intraoperative detection of tumor margins has been limited.

Improved site-directed delivery of contrast agents can be accomplished when a carrier molecules or ligand specific for a receptor is conjugated to some signaling species. In general the result is enhanced accumulation or association of this ligand with or in a certain type of cell, leading to high detection specificity when using of fluorescence imaging. For example, it has recently been demonstrated that implanted pancreatic acinar tumors, that over express the somatostatin receptor, could be imaged using a DOTA and a Indocyanine Green (ICG) conjugate. Another example of site directed contrast enhanced imaging is the use of folate to target several different kinds of cancer cells that are known to upregulate a receptor for this complex. One drawback of this approach to cancer detection is that the chemistry required for conjugation can often be quite complicated or require great synthetic skill.

Pyclen-based lanthanide chelates can be used as exogenous markers for epithelial carcinoma. Pyclen-based terbium chelate having the following chemical structure have been used to detect chemically induced colon cancers in the Sprague Dawley rat. As shown below, lanthanide chelates can be derived from the following ligands: 3,6,9-tris(methylene phosphonic acid n-butyl ester)-3,6,9,15-tetraaza-bicyclo[9.3.1]pentadeca-1(15),11,13-triene (PCTMB), 3,6,9-tris (methylene phosphonic acid)-3,6,9,15-tetraaza-bicyclo[9.3.1]pentadeca-1(13),11,13

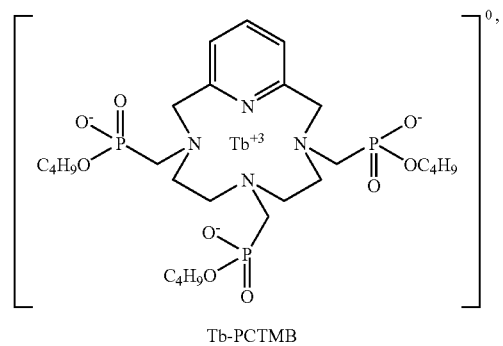

Tb-PCTMB

-continued

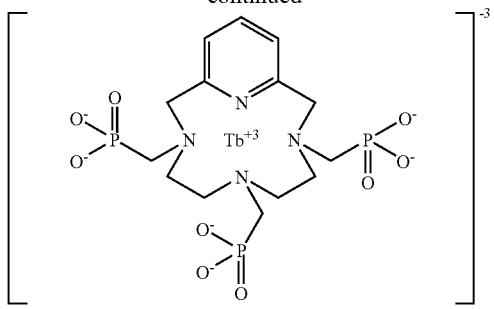

Tb-PCTMP

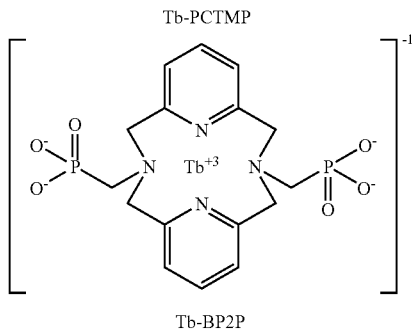

Tb-BP2P triene (PCTMP) and N,N'-bis(methylene phosphonic acid)-2,11-diaza[3.3]-(2,6)pyridinophane (BP2P). The molecule, Tb-[N-(2-pryidylmethyl)-N',N",N'''-tris(methylenephosphonic acid butyl ester)-1,4,7,10 tetraazacyclododecane] or Tb-PCTMB has excellent fluorescent properties, good specificity, and low toxicity. Preliminary work indicates that Tb-PCTMB can be used as an exogenous marker for dysplastic tissues with sensitivity as high as 94.7%. Using the bright green fluorescence from a tributyl ester $Tb^{3+}$ chelate with a tethered antenna, and subsequent histopathology, it is possible to detect squamous cell carcinoma lesions in the Syrian Hamster Cheek Pouch which are not visible by standard white light imaging. However, a major concern with using these pyclen-based lanthanide chelates is that the harvesting moiety, pyridine, requires high energy UV light (270 nm) to excite the lanthanide, which can be harmful to tissues. Therefore, a new class of chelates that does not require high energy UV light yet still retains a high degree of specificity and sensitivity is desirable.

When used as molecular imaging agents, contrast agents having conjugated complexes have the potential for high discrimination between histologically dissimilar (i.e. normal vs. diseased) tissues on the molecular level. In particular, mitochondrial function, specifically the over-expression of the peripheral benzodiazepine receptor (PBR) in cancerous tissue, has been suggested as an effective target with which to direct contrast agents for the identification of disease, especially cancers of the CNS. Although PBRs are widely expressed throughout the body in all steroid-producing tissues, their density in the CNS is primarily limited to the ependymal cells and glia. This 18 kDa protein is associated with many biological functions including the regulation of cellular proliferation, immunomodulation, porphyrin transport and heme biosynthesis, anion transport, regulation of steroidogensis and apoptosis, all processes that would be amplified in immortalized, rapidly proliferating tumor cells. The exploitation of PBR over expression has been shown to be a viable targeting technique for numerous times. A known high affinity PBR ligand PK11195 has been used both as an in-vitra and in-vivo PET agent for visualizing both human and rat gliomblastoma, and as a targeted therapeutic agent when conjugated to the drug gemcitabine. It has also been shown that a PBR ligand which is closely related to PK-11195, 7-Nitro-2,1,3-benzoxadiazol-4-yl, could be conjugated to a fluorescent label, 2-Phenylindole-3-acetamide, retaining the ability label PBR in glioma cell lines. While this compound is attractive, it provides only an optical signature and has not been conjugated to the most attractive PBR ligand, PK-11195.

For various reasons, including non-ideal interstitial solute transport properties and complicated pharmokinetics, the approach of using high-affinity vector molecules as contrast agents has been limited by poor specificity when used in vivo. This has not been the case when the isoquinoline, PK-11195, has been used as a ligand to target the peripheral-type benzodiazepine, a PBR ligand that labels glioma cells. Human glial tumors have been shown to display a high density of peripheral benzodiazepine binding (PBR) sites. The presence of such high concentrations of specific PBR receptors on glial tumors suggests that human primary brain tumors could be imaged and diagnosed using PBR ligands. Recent reports have demonstrated the feasibility of this hypothesis and have identified the peripheral benzodiazepine receptor ligand PK-11195 as an excellent candidate molecule. Intravenously administered $^3$H-PK-11195 has been shown to selectively label glioma cells in rat brains studied in-vitro and in-vivo. Moreover, autoradiograms of postmortem brain sections containing glioma revealed that $^3$H-PK-11195 bound specifically to intact tumor cells and not to cells of normal cortex or necrotic areas of the tumor. A clinical positron emission tomography (PET) study was carried out with $^{C11}$PK-11195 and demonstrated that saturable, high-affinity binding of the ligand corresponded directly to the tumor. Taken together, these findings provide support for the use of PK-11195 to image human gliomas. However, these studies have not been fully explored nor demonstrate the potential use of PK-11195 as a vehicle for contrast enhancement in brain cancer imaging. In addition, to imaging brain cancer, PK11195 may be useful in the identification of other forms of cancer. For example, breast cancer cells over-express substantial quantities of PBR as well.

At this time, there are no specific markers for neoplastic glial cells, thus allowing the unambiguous discrimination of human brain tumors from normal tissue. While there is a marker for glial cells called glial fibrillary acidic protein (GFAP), it is also present in reactive and normal glial cells. Furthermore, GFAP is inconsistently detectable in glioma cells. A sensitive and specific marker for neoplastic glial (glioma) cells would be of particular assistance in the identification of low cellularity infiltrating glioma cells amidst reactive glia. It may also have utility as a marker for distinguishing gliomas from other malignancies.

Current MRI modalities significantly improve patient diagnosis when tumor tissue is clearly distinguishable from normal tissue. In an attempt to fully identify a tumor in its entirety, clinicians infuse patients with a $Gd^{3+}$ containing contrast agent that exploits the varying degrees of angiogenesis between normal and diseased tissue. An effective method for increasing MR contrast in-vivo is to increase the relaxivity of the contrast agent, thus yielding greater differentiation between diseased and normal tissue with a $T_1$ weighted image, facilitating smaller agent doses to be administered reducing toxicity. Several groups have shown that by attaching $Gd^{3+}$ chelating agents to macromolecules the relaxivity of the combined contrast agent can increase substantially. Additionally by attaching several molecules of the contrast agent to polylysine (PL) and/or poly(ethylene glycol) (PEG), relaxivities in the 2500 mM$^{-1}$s$^{-1}$ range can be obtained. These relaxivities are three orders of magnitude better than commercially available MR contrast agents, because the greater size and amount of Gd$^{3+}$ present. It has recently been shown that paramagnetic ions can also be bound to proteins to yield an increase in relaxivity. Alternately, MR contrast can be improved by more effectively targeting the delivery of the agent. Iron complexes have been investigated, but as single entities they show no real enhancement over those of Gd(III).

Lanthanides containing compounds have also been used as temperature sensors. The optical fiber community has exploited this temperature dependent fluorescence of rare earths for some time relying on changes in the up-converted ionic fluorescent intensity or fluctuations in the ionic fluorescence lifetime. Current detection methodologies rely primarily on changes in the up-converted ionic fluorescent intensity or fluctuations in the ionic fluorescence lifetime. Typical fiber optic temperature sensors are temperature sensitive in the range from 20° C. to 140° C., with sensitivities on the order of 1×10$^{-2}$ Δ° C.$^{1}$. A new class of compounds that provides both improved tissue imaging, which also has the ability to exploit the temperature sensitivity of lanthanide series ions would be desirable.

BRIEF SUMMARY OF THE INVENTION

Multiple-signature, multi-modal imaging is possible by introducing an effective amount of a cyclen-based chelate into a sample of cells. When multiple cyclen-based chelates, each capable of delivering a single unique signature, are introduced as a single contrast agent, multi-modal imagining of diseases and tissues are possible. Multi-modal imaging is possible by detecting a first signal from the cyclen-based chelate and a second signal from a second imaging agent present in a contrast agent. The preferred cyclen-based chelates are non-toxic and useful for in-vitro diagnostics and in-vivo detection. The cyclen-based chelates produce new contrast agents that are useful in bi-modal imaging and therapy tracking. Cyclen-based chelates are used as contrast agents to provide in-vitro diagnostics and in-vivo disease detection. Sub-picomolar in-vivo detection limits can be achieved for these cyclen-base chelates. Time resolved detection is possible allowing improved site discrimination. Naked eye visualization of early stage epithelia lesions can be accomplished in-vivo. Contrast agents containing cyclen-based chelates provide a new molecular imaging tool that improves cancer detection, facilitates surgical assistance and provides in-vivo and in vitro measurements previously not possible.

This new class of cyclen-based chelates is essentially a series of molecules containing 1,4,7,10 tetraazacyclododecane ("cyclen") with different chelating ions and light harvesting moieties. The cyclen-based chelates may contain a variety of chelating ions depending on the type of imaging desired. Possible chelating ions include carbon (C), nitrogen (N), oxygen (O), flourine (F), bromine (Br), gallium (Ga), copper (Cu), nickel (Ni), selenium (Se), indium (In), technetium (Tc), yttrium (Y) and lanthanide (Ln) series ions. However, the preferred chelating ions are lanthanide series ions, which are hereinafter referred to as cyclen-based lanthanide chelates. By simply changing the chelating ion, a contrast agent can be prepared that provides imaging over a range of wavelengths. For example, by adding a radioactive lanthanide as the chelating ion, a PET tracer for molecular imaging may be formed. Different light harvesting moieties, known as sensitizers, are tethered to the cyclen macrocycle resulting in a simplified synthesis of the cyclen-based chelates. By tethering the sensitizer to the cyclen a wide variety of sensitizers may be used. Alternatively, the phosphoester chain length of the cyclen-based chelate may be altered to significantly change the biodistribution. When combining the ability to modify the sensitizer with the option to use different chelating ions within the cyclen, a broad range of fluorescent wavelengths ranging from green to the near infrared can be accessed.

When used as a mixture or cocktail, multi-modal imaging is possible which facilitates macroscopic and microscopic scale images of the same site providing fluorescent contrast, MRI contrast, CT contrast, PET contrast and x-ray contrast. For example, when preparing a cocktail containing cyclen-based lanthanide chelates with different fluorescing lanthanide ions, for example Gd$^{+3}$ or Sm$^{+3}$, multiple signature imaging agents are possible. Thus, multiple scales of imaging are possible from the same contrast agent. These contrast agents may be used to detect superficial lesions in epithelial tissue and show promise as molecular imaging agents in other tissues. "Diapeutic" compounds, those that have both diagnostic and therapeutic potentials, can be based on this strategy as well by combining radioactive metals and MRI active gadolinium as chelating ions. The resulting cyclen-based chelates produce a class of molecular probes whose spectral properties and biospecificity can be easily modified.

Additionally, a conjugable variation of the cyclen-based chelates (hereinafter referred to as "conjugable cyclen-based chelates") may be used as molecular imaging agents to produce site-directed delivery. Some preferred targeting agents that may be attached to the cyclen-based chelates include receptor ligands, antibodies, peptides and similar directing vectors. For example, a peripheral benzodiazepine receptor (PBR) specific ligand, such as PK-11195, can be coupled to a cyclen-based lanthanide chelate, yielding a contrast agent that will provide either a MRI or fluorescence signature and can be uptaken by glial cells. A contrast agent prepared as a cocktail of a Gd$^{+3}$-based lanthanide chelate conjugated with PK-11195 provide macroscopic scale images by MRI and a cocktail of the Eu$^{+3}$ or Tb$^{+3}$-based lanthanide chelate conjugated with PK-11195 will provide microscopic scale by fluorescence imaging from the same tissue. These contrast agents can be used to improve brain cancer clinical outcomes while facilitating an improved understanding of glial tumor development. In addition to the detection of brain cancer tumors, a cyclen-based lanthanide chelate conjugated with PK-11195 can be used to detect a variety of other types of cancer, including, but not limited to, breast cancer.

The cyclen-based chelates containing lanthanide ions are a special class of molecules that can produce unique contrast agents, in part because they can give various spectroscopic signatures including luminescence, radioactivity and NMR shift, but also because they have relative long fluorescence life-times. Cyclen-based lanthanide chelates can serve as platforms to facilitate NMR (MRI) signatures, commonly Gd$^{+3}$, gamma ray signatures ($^{166}$Ho$^{+3}$), beta particle signatures ($^{153}$Sm$^{+3}$), as well as the production of singlet oxygen. Due to the long lifetimes produced by this class of cyclen-based lanthanide chelates (100's of microseconds to several milliseconds), inexpensive gated detection methods may be employed to discriminate the signal from the background noise. Thus the complex can be detected even at low levels in the presence of high concentrations of other fluorophores such as collagen, NADH, ATP, DNA, etc.

Contrast agents may be prepared in the form of a cocktail or a bimetallic complex. The cocktail approach has advantages in that small molecules are easily delivered and relatively non-toxic. However, an integrated bimetallic complex also serves as a useful dual macromolecular imaging agent. Bimetallic complexes have been reported previously, yet none possessed the appropriate integrated multi-functionality. The present bimetallic complexes containing cyclen-base lanthanide chelates have bright fluorescence and a strong MR signature facilitating microscale and macroscale imaging from the same molecule. They also have long lifetimes allowing gated detection for further S/N gains, are non-toxic and non-immunogenic, and if necessary have long circulation times.

Cyclen-based lanthanide chelates have long emission lifetimes for detection in the zero noise regime, spectroscopic thermal sensitivity allowing the opportunity for use as molecular-level temperature probes and MRI relaxivity that is sensitive to pH making them potentially useful as nanoscale pH indicators.

The relaxivity of the contrast agent may be increase by creating a moiety of the cyclen-based chelates by attaching the cyclen-based chelates to macromolecules. Non-immunogenic synthetic polymers, such as poly(vinyl alcohol), poly(ethylene glycol), and natural polymers such as multi-valent sugars, carbohydrates, antibodies, proteins, peptibodies and peptides may be used in vivo as delivery vehicles for contrast agents and therapeutics. Polyethylene glycol, of PEG, may be employed to increase in vivo circulation time.

BRIEF DESCRIPTION OF THE DRAWINGS

The features and advantages of the present invention will become apparent from the following detailed description of the preferred embodiments thereof, taken in conjunction with the accompanying drawings, in which.

DETAILED DESCRIPTION OF PREFERRED EMBODIMENTS

Figure 1:
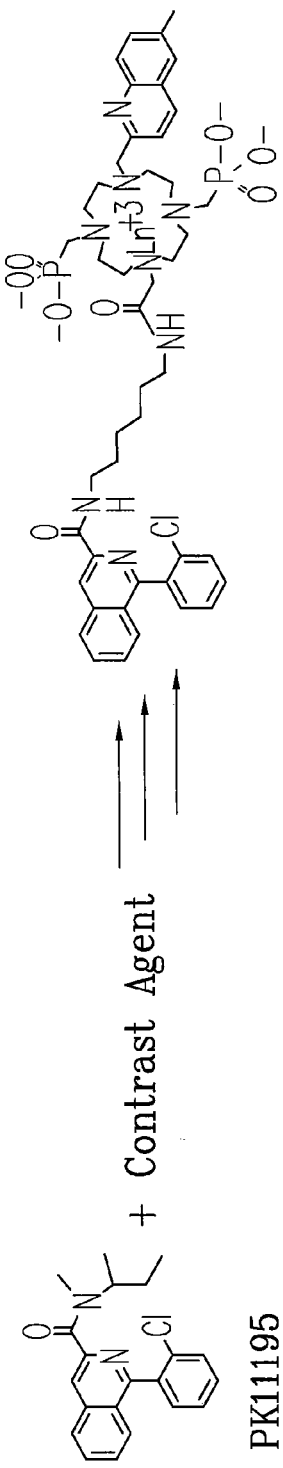
FIG. 1 depicts a general synthetic strategy for delivering a multi-signature contrast agent containing a PK11195 conjugated cyclen-based lanthanide chelate to PBR over-expressing tissues.

Cyclen-based chelates 1 used as contrast agents for multi-modal imaging are polyazamacrocyclic molecules preferably formed from 1,4,7,10 tetraazacyclododecane ("cyclen") containing various chelating ions, M, having a general formula as shown below.

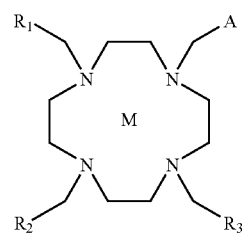

$R_1$, $R_2$, and $R_3$ are selected from the group comprising

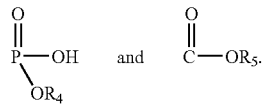

$R_4$ is H, $CH_3$, $C_2H_5$, $C_3H_7$, $C_4H_9$, $C_5H_{11}$, $C_6H_{13}$.

The chelating ion, M, may be selected from a wide range of elements depending on the type of imaging desired. Examples of chelating ions include, but are not limited to, carbon (C), nitrogen (N), oxygen (O), flourine (F), bromine (Br), gallium (Ga), copper (Cu), nickel (Ni), selenium (Se), indium (In), technetium (Tc), yttrium (Y) and lanthanide (Ln) series ions. PET imaging is possible with cyclen-based chelates containing $^{68}Ga$, $^{58}NI$, $^{73}Se$, $^{100m}In$, $^{94m}Tc$, $^{60}Cu$, $^{64}Cu$, $^{86}Y$, $^{11}C$, $^{13}N$, $^{15}O$, $^{18}F$, $^{75}Br$ and $^{76}Br$ ions as chelating ions. MI imaging, fluorescent imaging, CT imaging, and x-ray imaging are possible with lanthanide series ions as the chelating ion. Different light harvesting moieties may be attached to the cyclen by tethering a sensitizer, A, to the cyclen structure. Additionally, the phosphoester chain length of the cyclen-based chelate may be altered to change biodistribution. The phosphoester chain length may be altered by adding alkyl groups to the phosphoester, with R=H, $CH_3$, $C_2H_5$, $C_3H_7$, $C_4H_9$, $C_5H_{11}$, and $C_6H_{13}$. Cyclen-based chelates that contain lanthanide series ions (Ln) as the chelating ion are hereinafter referred to as cyclen-based lanthanide chelates. Preferred sensitizers, A, for the cyclen-based chelates are selected from the group listed below:

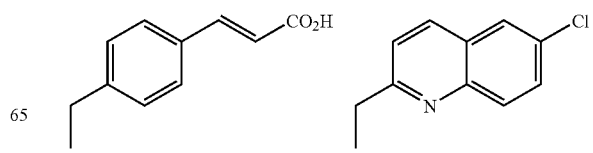

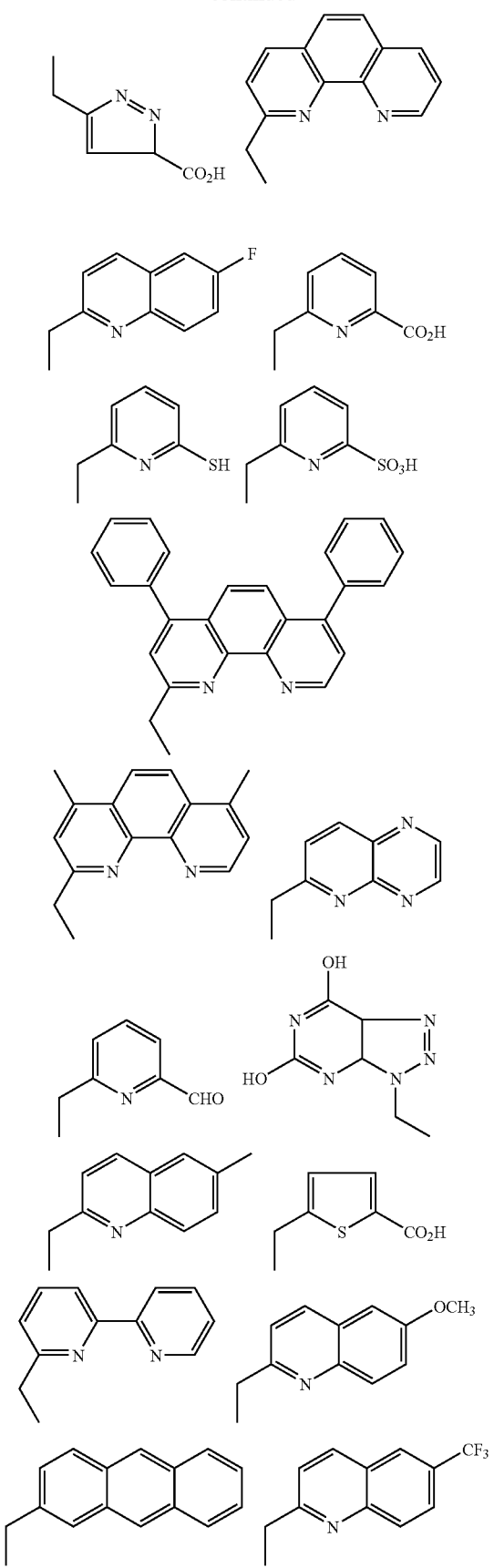
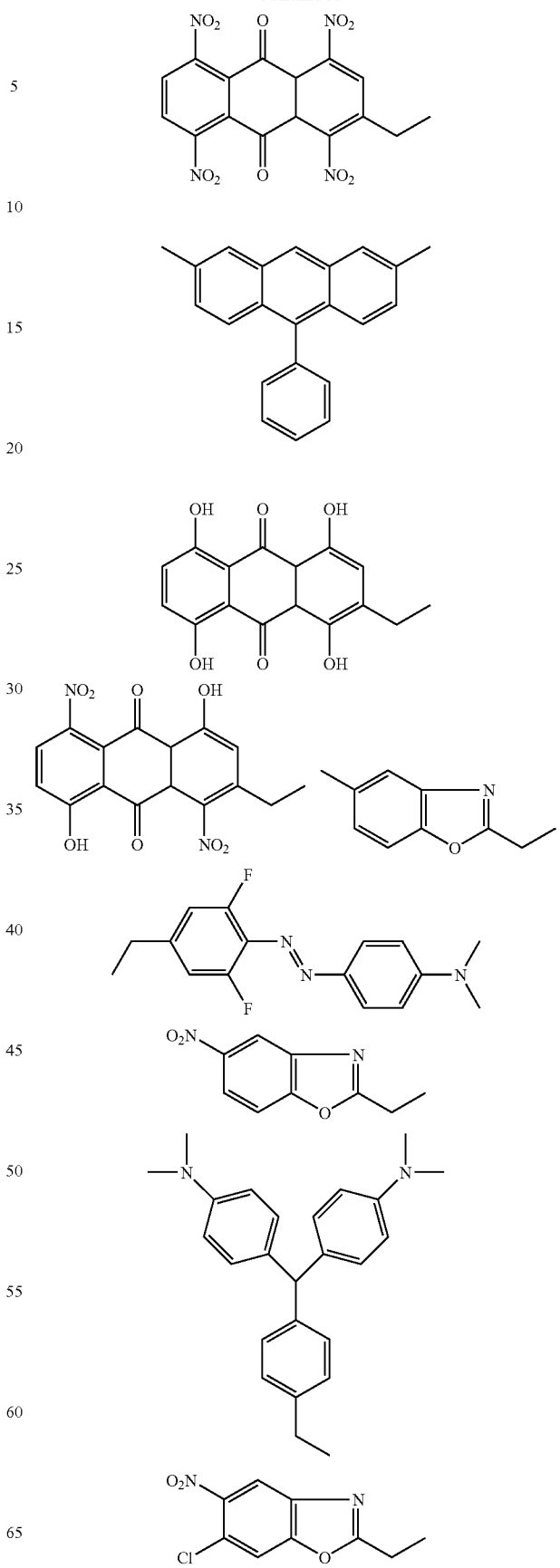

-continued
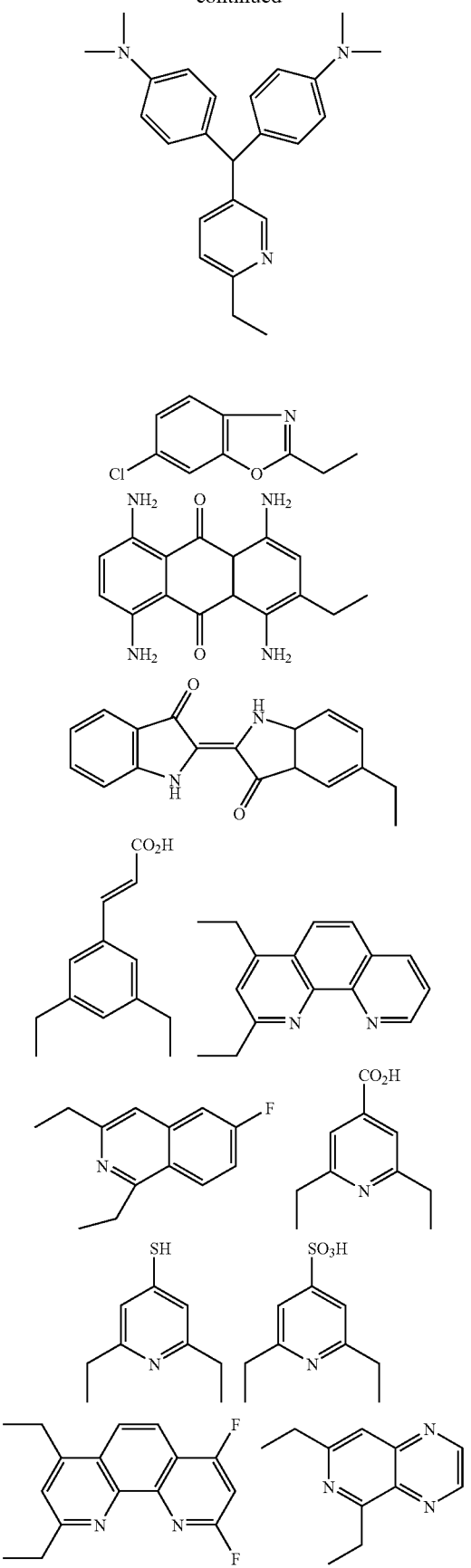
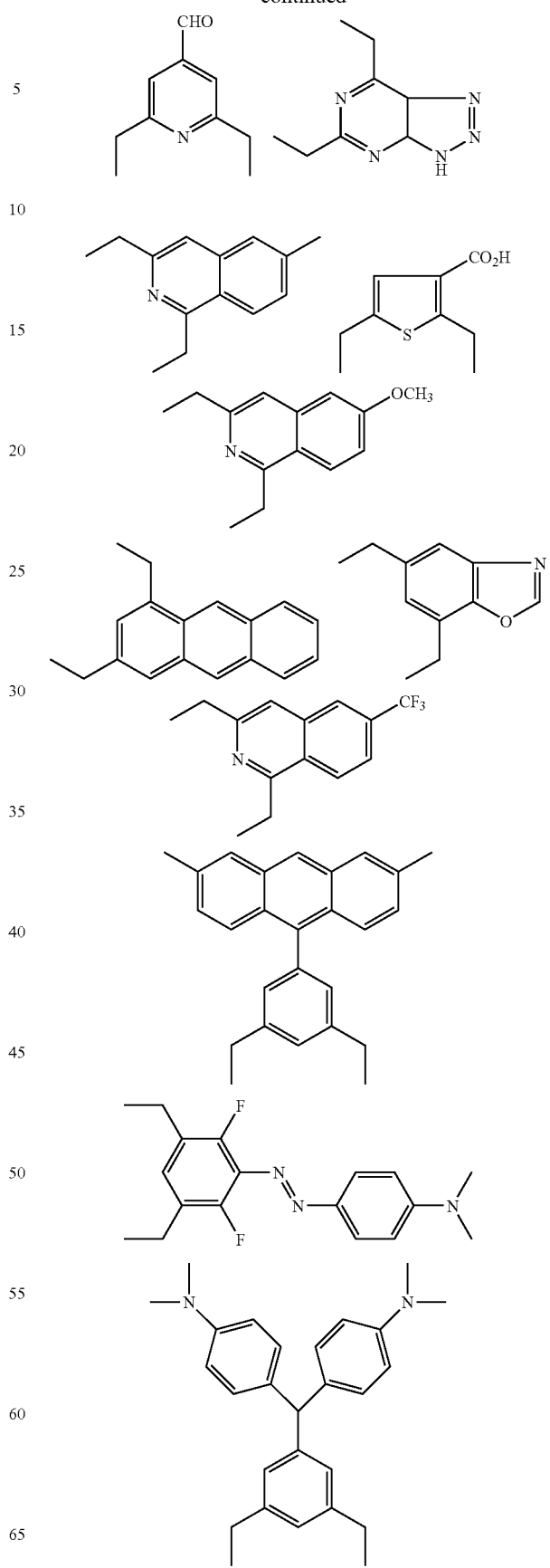

-continued

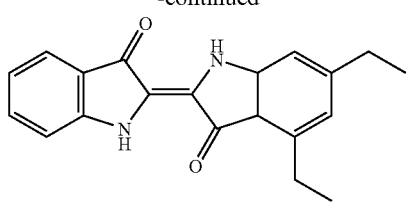

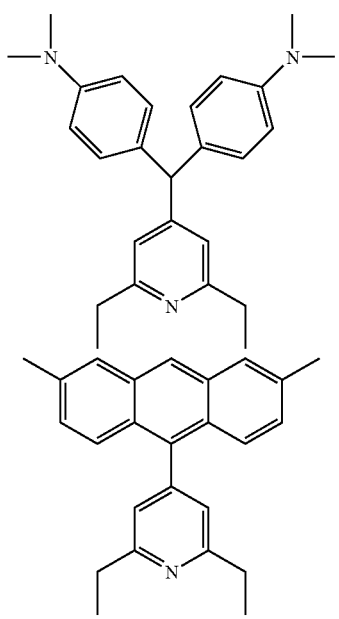

The lanthanide series ion (Ln) may be selected from any of the lanthanide series of atoms. Preferably the lanthanide series ion is selected from the group comprising gadolinium (Gd), terbium (Tb), europium (Eu), ytterbium (Yb), neodymium (Nd), and erbium (Er). By preparing cocktails of both the $Gd^{+3}$ and $Eu^{3+}$ or $Tb^{+3}$ cyclen-based chelates, it is possible to obtain macroscopic scale images by MRI and perform microscopic scale detection by fluorescence imaging on the same cell or tissue.

One embodiment of the present invention is a method for delivering an agent to a sample of cells that comprises: (a) providing a compound the following formula:

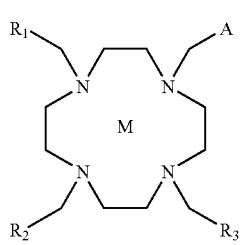

wherein:

M is a chelating ion selected from the group consisting of gallium (Ga), copper (Cu), nickel (Ni), indium (In), technetium (Tc), yttrium (Y) and lanthanide (Ln) series ions;

$R_1$ and $R_3$ are, independently,

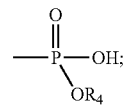

$R_2$ is

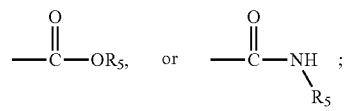

$R_4$ is H, $CH_3$, $C_2H_5$, $C_3H_7$, $C_4H_9$, $C_5H_{11}$, $C_6H_{13}$;
A is a sensitizer; and
$R_5$ is:

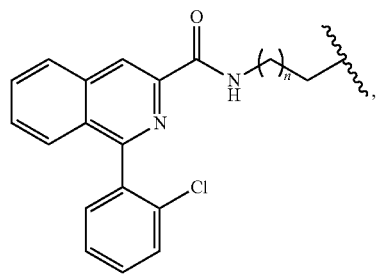

with n is 0-10; and (b) introducing the conjugate to the sample of cells.

Another embodiment of the present invention is a method for multi-modal imaging a sample of cells that comprises (a) administering to said sample of cells an effective amount of a cyclen-based chelate of the Formula (I):

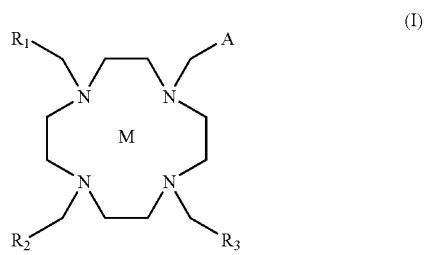

wherein:

M is a chelating ion selected from the group comprising gallium (Ga), copper (Cu), nickel (Ni), indium (In), technetium (Tc), yttrium (Y) and lanthanide (Ln) series ion;

$R_1$ and $R_3$ are, independently,

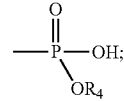

$R_2$ is

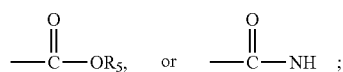

$R_4$ is H, $CH_3$, $C_2H_5$, $C_3H_7$, $C_4H_9$, $C_5H_{11}$, $C_6H_{13}$;

A is a photo-stable sensitizer;

$R_5$ is a compound of the formula:

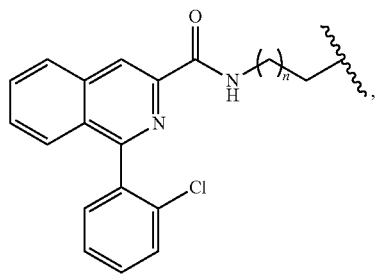

wherein n is 0-10; and (b) detecting a signal from said cyclen-based chelate.

The lanthanide series ions may be easily changed allowing a significant portion of the electromagnetic spectrum to be accessed. Table 2 shows that lanthanide emission from blue to the near infrared is possible depending on the chelating ion used.

TABLE 2

| | |
|---|---|
| $Tb^{+3}$ | 470-625 nm |
| $Eu^{3+}$ | 575-710 nm |
| $Yb^{+3}$ | 1000 nm |
| $Nd^{3+}$ | 1064 nm |
| $Er^{+3}$ | 1575 nm |

As shown below, the cyclen-based lanthanide chelates 7 may be formed by adapting pyclen-based lanthanide chelates 3 and then tethering antennas to the resulting cyclen-based lanthanide chelate 5. By way of example, a pyclen-based lanthanide chelate 3 is generally transformed into a cyclen-based lanthanide chelate 7 by the following mechanism:

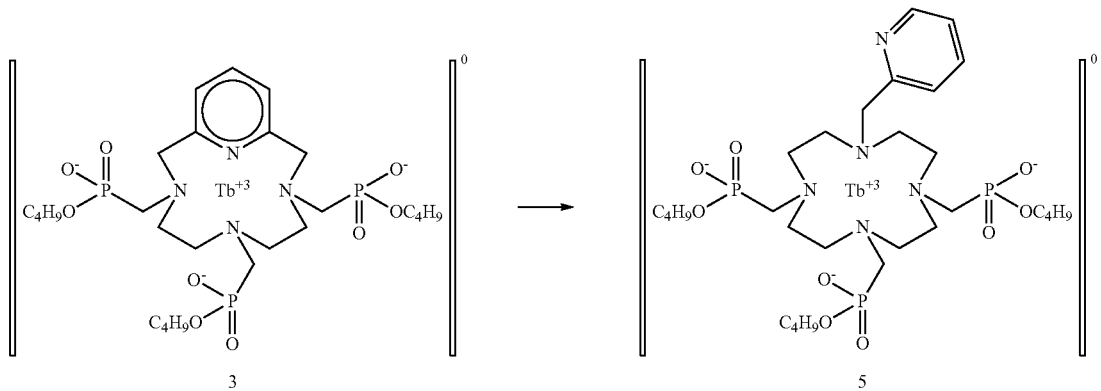

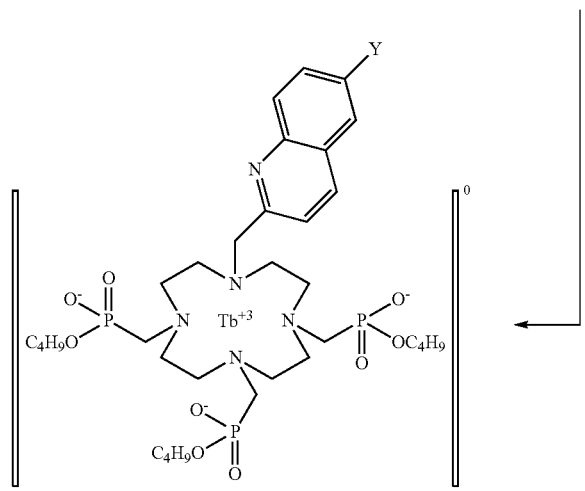

For synthetic reasons, the antenna is preferably tethered to the cyclen macrocycle 5, rather than attempting to modify the pyridyl group that is incorporated into the macrocycle in the pyclen-based lanthanide chelates 3.

A variety of cyclen-based chelates may be formed in order to obtain the desired diagnosis of a particular disease by altering the phosphoester chain length. Non-conjugated cyclen-based lanthanide chelates 8, as shown below, are useful as imaging agents.

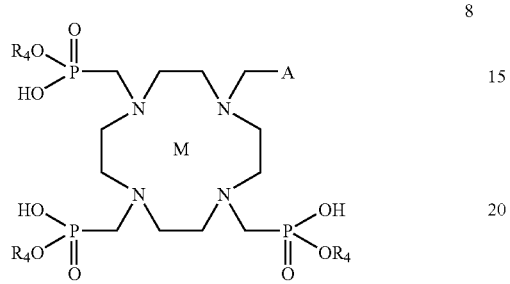

8

When high lipophilicity is desirable, the chain length of the cyclen-base lanthanide chelate can be lengthened, even beyond six carbons (i.e. $R=C_6H_{13}$). If a non-lipophilic solute is desirable, full phosphonic acids can be synthesized (i.e. R=hydrogen). Rat biodistibution data confirms that these types of structural modifications lead to site directed delivery. This first set of lanthanide chelates 8 may be native, physiologically molecules transported by charge, mass, lipophilicity, etc. This first set of lanthanide chelates is fully compatible for diagnostic use in vivo and in vitro, as well as many other functions.

Additionally, a second set of conjugable cyclen-based chelates is produced yielding trifunctional markers. This second set of conjugable cyclen-based chelates retains the capability of signaling and stability, yet are also fully conjugable to bioactive species such as receptor ligands, peptides, antibodies, molecular probes and certain cell signaling metabolites. The conjugable cyclen-based chelates in the second set may be tailored to produce molecular probes for site directed delivery with selectable optical superficial UV/Visible, deep tissue NIR-IR wavelengths, MRI and radiation signaling properties. A preferred carboxylate conjugated cyclen-based chelate 9 is depicted below.

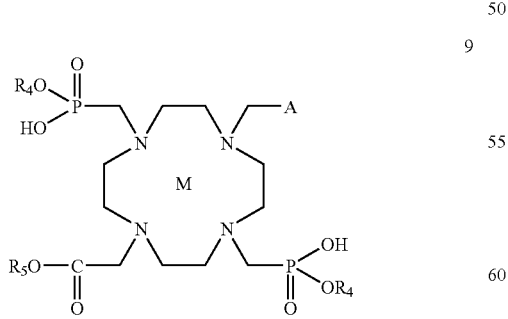

9

As in the first set of cyclen-based chelates 1, M, A, $R_1$, $R_2$, $R_3$ and $R_4$ are as previously defined. $R_5$ indicates the place where the conjugation of the biological species occurs. Examples of preferred PBR conjugable ligands include the following:

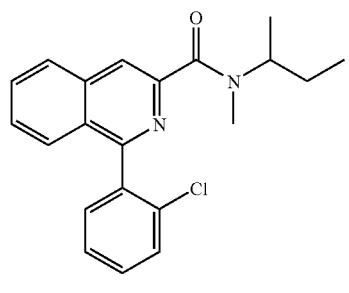

PK11195

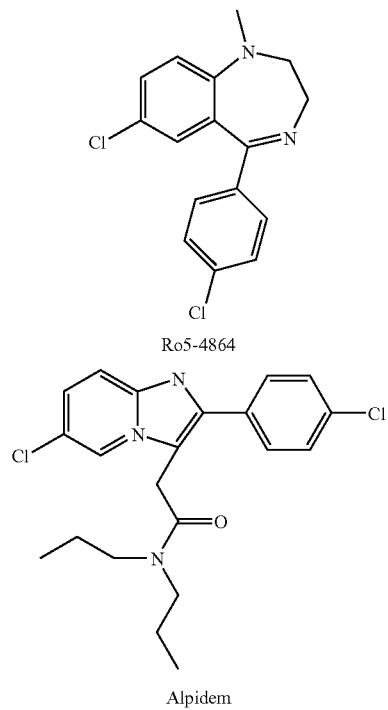

Ro5-4864

Alpidem

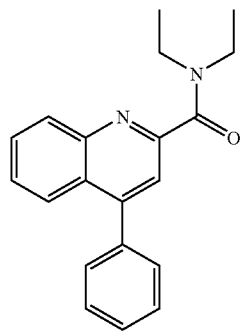

Figure 2:
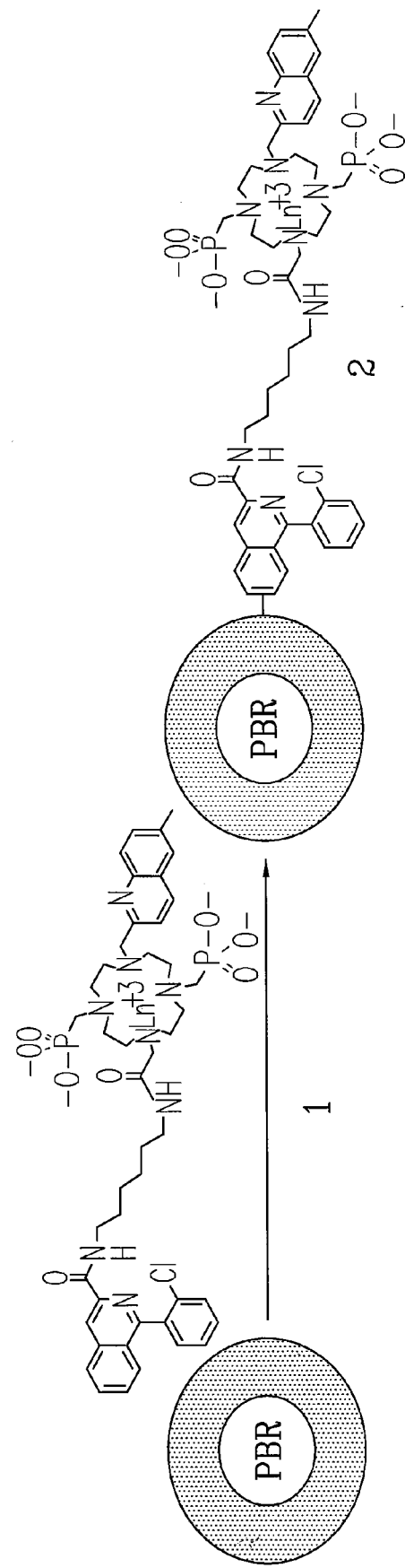
FIG. 2 depicts a strategy for the selective targeting of contrast agents to PBR-over expressing cancerous tissues.

FIG. 1 illustrates the general synthetic strategy for delivering multi-signature contrast agents to PBR over-expressing tissue. More specifically, FIG. 1 shows an analogue of PK11195 conjugated to a cyclen-based lanthanide chelate. FIG. 2 shows a strategy for the selective targeting of a contrast agents containing a cyclen-based lanthanide chelate conjugated to PK11195 to PBR-over expressing cancerous tissue.

The total charge of the cyclen-based chelates can easily be varied by modifying the pendant arms, yielding complexes charged negatively, positively, or neutral. Thus, a wide range of functionality is possible when using these cyclen-based chelates. For example, the following cyclen-based lanthanide chelate 11 exhibits infinite water solubility while maintaining high lipophilicity and strong chelating ability.

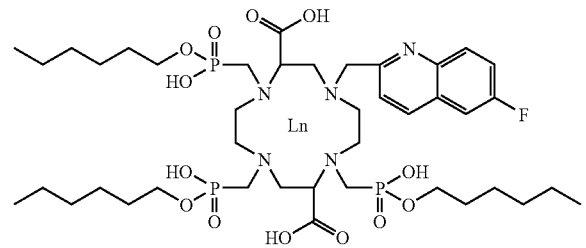

11

The contrast agent may be formed by preparing either cocktails or bimetallic complexes of the cyclen-based chelates. There are numerous reasons for preparing a bimetallic complex that has the capability of ligating two different metals, including the realization of multi-signature complexes and even the possibility of directly monitoring a therapeutic dose while delivering it. Taking advantage of the unique properties of cyclen-based chelates, this new bimetallic complex gives both MRI and bright fluorescent signatures simultaneously.

Alternately, imaging may be performed by preparing two different cell lines, each with a different cyclen-based chelate. The preference for a first cell line could be tracked in relation to a second cell line. This technique could also be used to separate two different cell lines. For example, one cell line could contain Nd as the chelating ion and the second cell line could contain Yb as the chelating ion.

The cyclen-based chelates may also be used as molecular agents for nano-scale temperature sensing. There are numerous scenarios in biological research where it is desirable to measure changes in temperature of a local environment. Temperature determination would be possible by preparing mixtures of cyclen-based lanthanide chelates that are and are not temperature sensitive. For example, by using the relative change in luminescence intensity at 615 nm (Eu) and 550 nm (Tb), the temperature can be extracted.

Non-immunogenic synthetic polymers, such as poly(vinyl alcohol), poly(ethylene glycol), and natural polymers such as multi-valent sugars, carbohydrates, antibodies, proteins, peptibodies, and peptides can be used in vivo as delivery vehicles for both contrast agents and therapeutics. These polymers can be both site directed by coupling a targeting moiety to the polymer such as a high binding affinity receptor ligand, an antibody, a peptide, and such, or the polymer can be a long circulating perfusion agent. A moiety containing the cyclen-based chelates may be formed by coupling to the delivery vehicle cyclen-based chelates, such as those yielding fluorescent, PET, MRI, X-Ray, and/or ultrasound signatures, for multi-modal visualization of a disease state. For targeted therapy, a moiety may be formed which contains cyclen-based chelates having site-directing moieties coupled to the delivery vehicle. The following is an illustration of a hetero-multimeric visualization moiety 14 with multiple scales of imaging possible from one molecule.

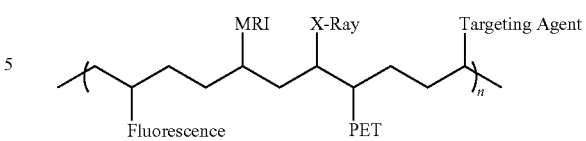

14

In similar fashion to the hetero-multimeric visualization moiety 14, these delivery vehicles can be used for therapeutics as well. Using poly(vinyl alcohol), poly(ethylene glycol) and similar non-immunogenic polymers, or natural polymers such as multi-valent sugars, carbohydrates, antibodies, proteins, peptibodies, and peptides, therapeutics such as radio nuclides, therapeutic antibodies and/or genes, singlet oxygen producers, and/or antibiotics can be delivered to the site of a disease. As shown in the following hetero-multimeric therapeutic moiety 15, a targeting moiety such as a receptor ligand, an antibody, a peptide or similar directing vector can also be utilized.

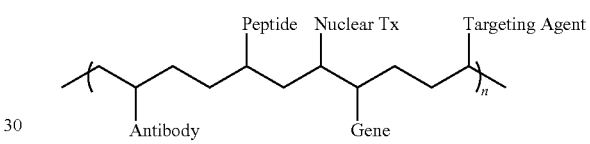

15

In similar fashion to the hetero-multimeric visualization moiety 14 and hetero-multimeric therapeutic moiety 15 above described, therapeutic agents can be incorporated with imaging agents, all delivered by a single polymeric backbone. Incorporated imaging therapeutics provides real-time therapy monitoring, affording the clinician the ability to monitor the therapeutic dose and efficiently visualize the dose-disease response. Additionally, by utilizing the multi-modal concept, multiple scales of imaging are possible. This hetero-multimeric incorporated imaging therapeutic 16 is illustrated below.

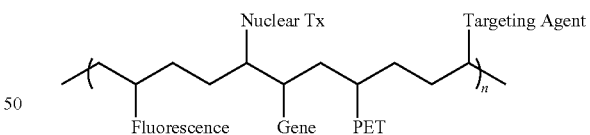

16

By way of example, poly(ethylene glycol) (PEG) or synthetic polypeptides such as poly(lysine) (PL)PEG and PEG-PL may be used as synthetic polymeric carriers for the cyclen-based lanthanide chelates in an effort to demonstrate long blood half-life, large MR signatures, and disease specificity. Synthetic carriers, such as poly(ethylene glycol) (PEG) or synthetic polypeptides such as poly(lysine) (PL), are less toxic and less immunogenic than natural carriers. Even though smaller polymer supports typically result in rather fast clearance (90% in 1 hour), larger supports and branched polymers undoubtedly increase blood pool half-life. Polyethylene glycol, PEG, can easily be incorporated into the cyclen-based lanthanide chelates to afford increased plasma stability and blood circulation time.

EXAMPLE 1
Method of Making Cyclen-Based Lanthanide Chelates
Scheme I shows a method of preparing a first class of cyclen-based lanthanide chelates by attaching quinoline antennae to cyclen and then functionalizing the macrocycle.
Scheme I
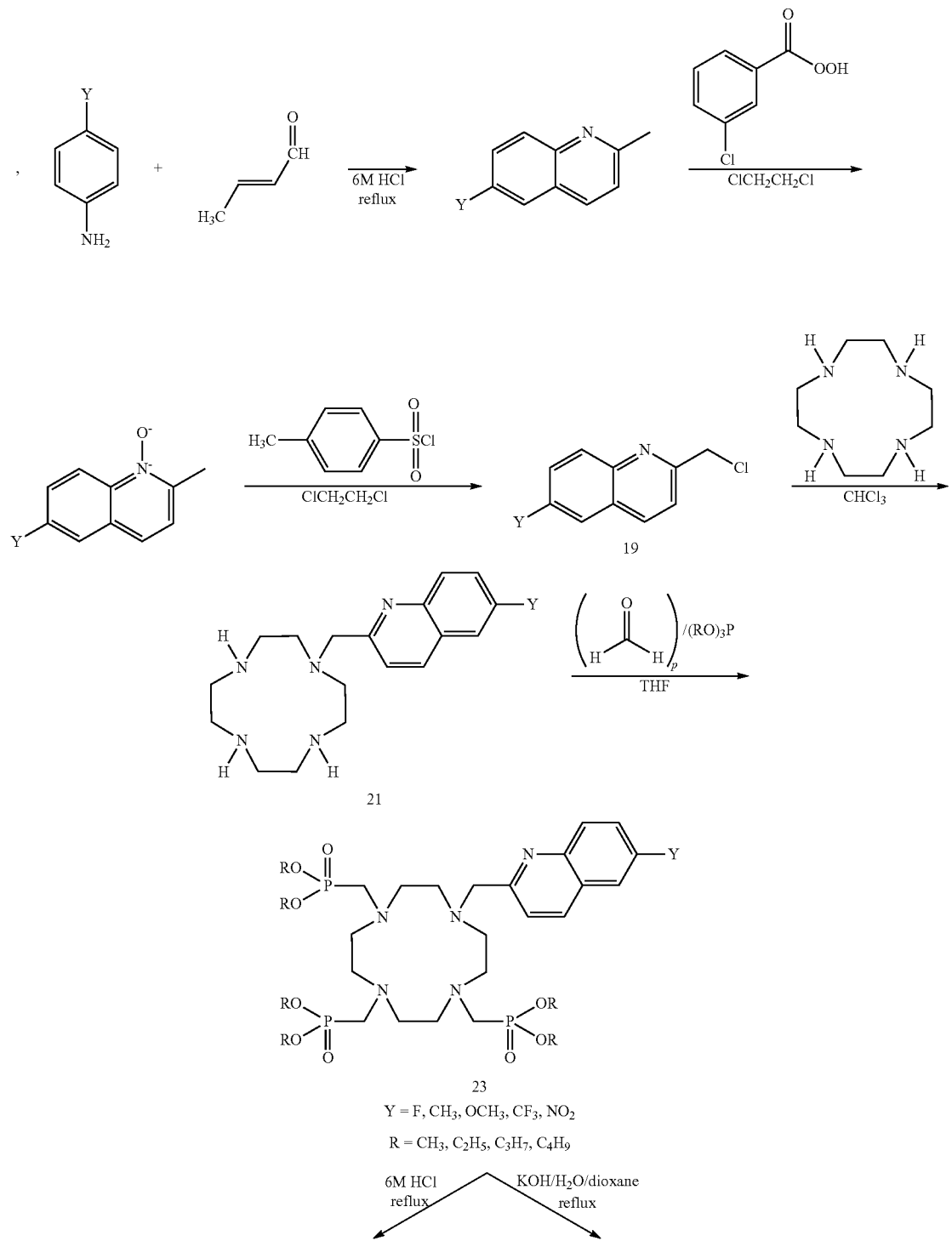
$Y = F, CH_3, OCH_3, CF_3, NO_2$
$R = CH_3, C_2H_5, C_3H_7, C_4H_9$
6M HCl reflux    KOH/H$_2$O/dioxane reflux

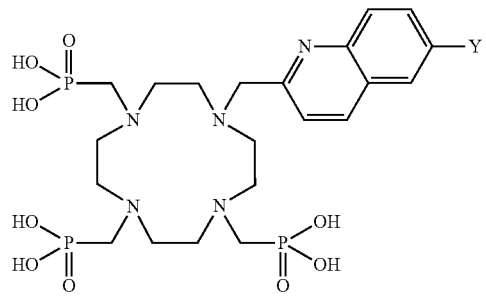

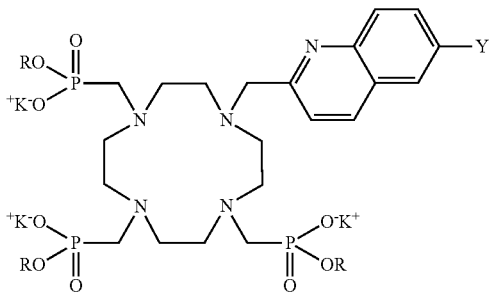

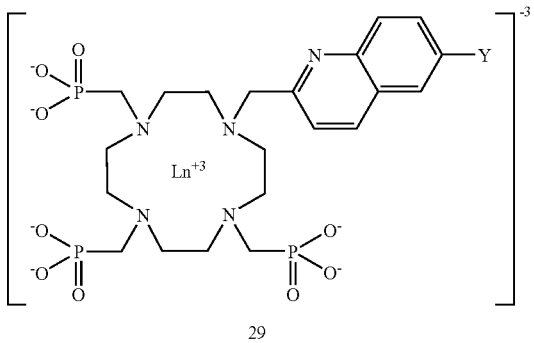

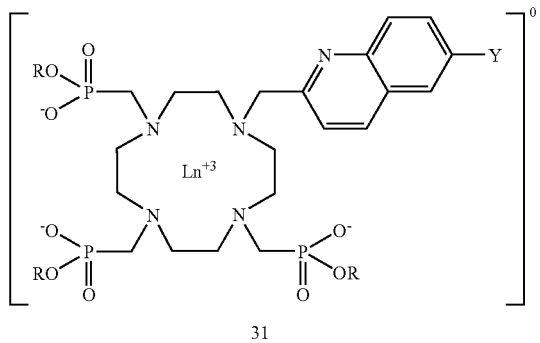

First, to a stirring solution of cyclen (3.52 g, 0.0204 mol) in chloroform (525 mL) was added 2-(Chloromethyl)-6-fluoroquinoline 19 (2 g, 0.0102 mol). The reaction was then allowed to stir until completion as determined by TLC, concentrated and purified on silica using a gradient elution system starting with 50:1 $CHCl_3$:MeOH; 150:4:1 $CHCl_3$:MeOH:$NH_4OH$; 100:4:1; 50:4:1; and finally with 20:4:1 to afford 2.54 g (75%) of a pale yellow oil that solidified on standing to an off-white solid. The resulting compound is N-(6-fluoro-2-quinolylmethyl)-1,4,7,10 tetraazacyclododecane 21.

Formation of N-(6-fluoro-2-quinolylmethyl)-N',N'',N'''-tris(methylene phosphonic acid)-1,4,7,10 tetraazacyclododecane 25, wherein Y=F To a stirring solution of the resulting N-(6-fluoro-2-quinolylmethyl)-1,4,7,10 tetraazacyclododecane 21 (1 g, 0.00302 mol) in dry THF (50 mL) under $N_2$ was added paraformaldehyde (0.298 g, 0.00942 mol). The reaction was allowed to stir for 3 hours at room temperature. Tributylphosphite (2.48 g, 0.00942 mol) is then added to N-(6-fluoro-2-quinolylmethyl)-1,4,7,10 tetraazacyclododecane 21 the mixture slowly and allowed to stir until the solution turns completely clear. The completed reaction mixture was concentrated and dried under high vacuum for 24 hours to afford a pale yellow oil. The resulting oil was dissolved in 6 M HCl (50 mL) and heated with stirring to a gentle reflux for 4 days. The solution was allowed to cool and excess HCl was removed by azeotropic distillation with water to afford a pale yellow solid. The product was then further purified, if necessary, by recrystallization with anhydrous isopropyl alcohol to afford 2.17 g (90%) of a white solid. The compound was isolated in its fully protonated form.

Formation of N-(6-fluoro-2-quinolylmethyl)-N',N'',N'''-tris(methylene phosphonic acid ethyl ester)-1,4,7,10 tetraazacyclododecane 27, where Y=F and R=$C_2H_5$ To a stirring solution of the resulting N-(6-fluoro-2-quinolylmethyl)-1,4,7,10 tetraazacyclododecane 21 (1 g, 0.00302 mol) in dry THF (50 mL) under $N_2$ was added paraformaldehyde (0.298 g, 0.00942 mol). The reaction was allowed to stir for 3 hours at room temperature. Triethylphosphite (1.59 g, 0.00942 mol) was then added to the mixture and allowed to stir until the solution turned completely clear. The completed reaction mixture was concentrated and dried under high vacuum for 24 hours to afford a pale yellow oil. The oil was then refluxed for four days with 27 equivalents of KOH dissolved in 20 mL of $H_2O$ with enough dioxane to achieve solubility. The resulting mixture volume was then reduced under vacuum to produce thick oil. The oil was then washed with a series of increasing chloroform concentration methanol/chloroform solutions with filtration and removal of solvent. The resulting oil was then dissolved in a minimal amount of chloroform and acetonitrile was then added until the solution became cloudy. The mixture was allowed to stand to precipitate the pure product, which was then filtered, dissolved in water, and lyphilized to produce 1.83 g of white, flaky solid.

Formation of N-(6-fluoro-2-quinolylmethyl)-N',N'',N'''-tris(methylene phosphonic acid butyl ester)-1,4,7,10 tetraazacyclododecane formation 27, where Y=F and R=$C_4H_9$ To a stirring solution of the resulting N-(6-fluoro-2-quinolylmethyl)-1,4,7,10 tetraazacyclododecane 21 (1 g, 0.00302 mol) in dry THF (50 mL) under $N_2$ was added paraformaldehyde (0.298 g, 0.00942 mol). The reaction was allowed to stir for 3 hours at room temperature. Tributylphosphite (2.48 g, 0.00942 mol) was then added to the mixture and allowed to stir until the solution turned completely clear. The completed reaction mixture was concentrated and dried under high vacuum for 24 hours to afford a pale yellow oil. The oil was then refluxed for four days with 27 equivalents of KOH dissolved in 20 mL of $H_2O$ with enough dioxane to achieve solubility. The resulting mixture volume was then reduced under vacuum to produce thick oil. The oil was then washed with a series of increasing chloroform concentration methanol/chloroform solutions with filtration and removal of solvent. The resulting oil was then dissolved in a minimal amount of chloroform and acetonitrile was then added until the solution became cloudy. The mixture was allowed to stand to precipitate the pure product, which was then filtered, dissolved in water, and lyophilized to produce 1.75 g (65%) of a white, flaky solid.

Method of Making Cyclen-Based Lanthanide Chelates 29 and 31

The following chelation procedure for europium (Eu) and the butyl half-ester is demonstrated to produce a lanthanide chelate designated Eu-Q{F}-CTMB. A potassium salt of N-(6-fluoro-2-quinolylmethyl)-N',N'',N'''-tris(methylene phosphonic acid butyl ester)-1,4,7,10 tetraazacyclododecane 27 (where Y=F and R=$C_4H_9$), (300 mg, $3.77\times10^{-4}$ mol) is dissolved in 100 mL of distilled water. The pH of the solution, which was around 10.5 to start, was then adjusted to 6.5 using dilute hydrochloric acid. Europium chloride hexahydrate (128 mg, $3.77\times10^{-4}$ mol) was dissolved in 50 mL of distilled water and added to the butyl half ester solution dropwise with stirring. The pH was maintained at around pH=6 with a dilute potassium hydroxide solution. Addition of potassium hydroxide was terminated after all the europium salt had been added and when the pH had settled around 6.4. The solution was then lypholized, redissolved in chloroform and filtered through celite. The resulting filtrate was then concentrated producing a glassy solid. The solid was then taken up in water and filtered through a microfilter to remove $Eu(OH)_3$ and lipholized to produce a flocculent white solid.

Testing Results

The cyclen-based lanthanide chelates have improved spectroscopic properties when compared to the pyclen-based chelates (PCTMX) and tethered pyclen-based chelates (T-PCTMX). Table 3 shows the results of a test of cytotoxicity of Eu-Q{F}-CTMB, average of three trials.

TABLE 3

|  | Control | Eu-QF-CTMB |
|---|---|---|
| Total cell population | $2.22 \times 10^6$ | $2.44 \times 10^6$ |
| Live Cells | 81.2% | 81.1% |
| Dead Cells | 18.8% | 18.9% |

Figure 3:
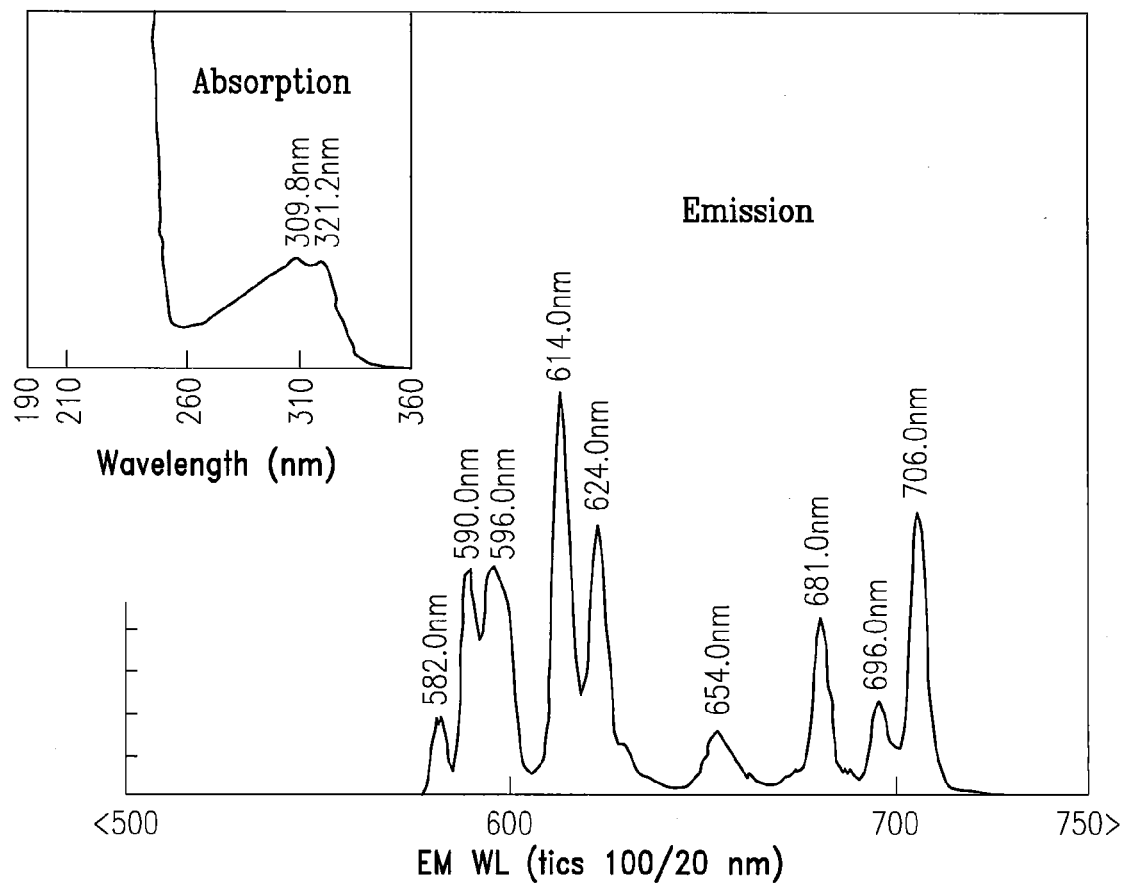
FIG. 3 are absorption and emission graphs showing the spectra and fluorescence of Eu-Q{m}-CTME.

In-vivo imaging was even used to aid in identifying early-stage cancerous lesions in the Golden Syrian Hamster cheek pouch model. Typical absorption and emission spectra are presented in FIG. 3. The quantum efficiency and molar extension coefficient for a red-shifted lanthanide cyclen-based chelates will depend on the lanthanide ion, pendent arm functionality (ethyl or butyl ester, free acid group) and the identity of the antenna, but as shown in FIG. 3, the absorption is blue shifted to the safer 310-340 nm region. The inset in FIG. 3 is a photograph that shows these quinoline-containing cyclen-based lanthanide chelates (Ln-Q-Y-CTMR) can have extremely bright fluorescence, even when using low power 300-400 nm excitation (long wavelength of a TLC plate reader).

Figure 4:
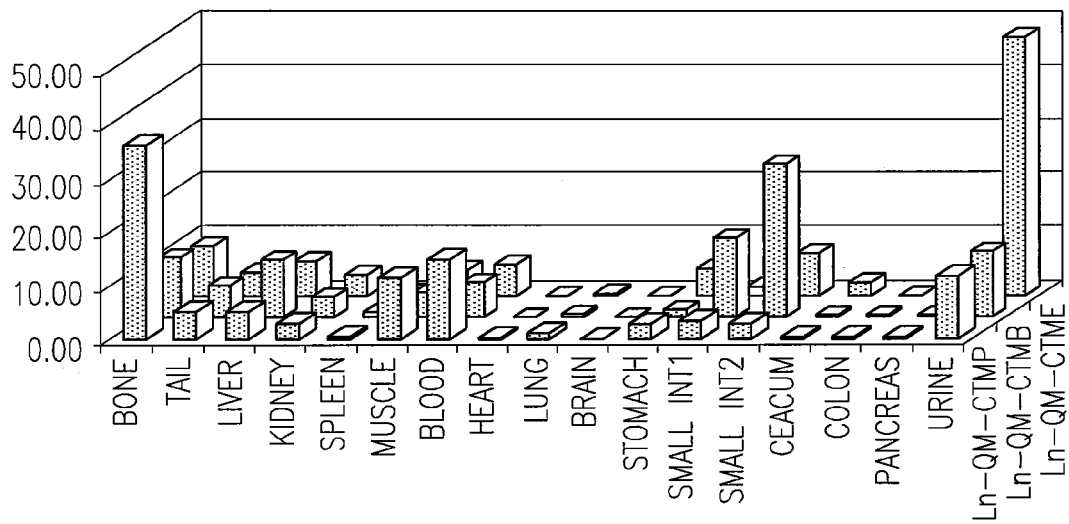
FIG. 4 is a graph showing the biodistribution for the quinoline methyl, acid, ethyl and butyl chelates.

The cyclen-based lanthanide chelates are advantageous because facile synthetic procedures can easily produce chelates with structural changes that influence biodistribution or transport in cells. This property makes them tunable. For example, by modifying the quinoline-containing cyclen-based lanthanide chelates (Ln-Q-Y-CTMR) from the full acid into a half-ester, rat tissue biodistribution is substantially changed as shown in FIG. 4. Here 1 mM solutions of the full acid, ethyl and butyl half esters of the $Lu^{3+}$ cyclen-based lanthanide chelates were administered to normal male Sprague Dawley rats by tail vein injection. Using the radioactive lanthanide ion Lu instead of Eu or Gd is common practice for such studies because it is assumed the identity does not influence the transport of the final cyclen-based lanthanide chelate. After two hours the animals are euthanised, organs are collected and ground-up, and the radioactivity from each tissue quantified. As shown in FIG. 4, the target organ or biodistribution is dependent upon the structure of the cyclen-based lanthanide chelate and that even subtle changes in structure, transformation from an ethyl to a butyl half ester (one $CH_3$ group), has a major effect on the delivery. In this series the full acid tends to associate with the bone, while the half esters can be directed to the intestine. Later time course data indicate that the butyl and ethyl half esters will 'traverse' the intestine moving from the small intestine to the colon and can be found primarily in the luminal walls.

In order to test the cyclen-based lanthanide chelates for suitability as topical contrast agents, the butyl and ethyl ester fluoro and methyl-quinoldine complexes of $Eu^{3+}$ were constructed and a series of disease detection studies were performed. In a pilot study a well-characterized protocol for oral epithelial carcinogenesis, such as dimethylbenzanthracene (DMBA), and a soft tissue inflammation model, such as sodium lauryl sulphate (SLS) as a benign lesion initiator, was used in combination with OCT, autofluorescence, PP-IX fluorescence and contrast enhanced imaging to demonstrate that the present contrast agents work well in demarcating cancer, but not benign disease. A topically applied 1 mM solution of the first tethered complex, Tb-T-PCTMB, marks very early stage lesions that are not detectable with the naked eye. The very bright, localized fluorescent signature of the suspect site was confirmed by OCT and H&E and determined to be a foci of dysplastic cells.

To definitively demonstrate that the cyclen-based lanthanide chelates, with improved spectroscopic properties, are suitable for in-vivo use, additional imaging experiments were performed. Here the pink-red fluorescent Eu(III) fluoro-quinoline tibutylester, (Eu-Q-F-CTMB) and Eu(III) methyl-quinoline tiethylester, (Eu-Q-Me-CTME) chelates were used in an expanded oral cancer study. The chelates provided significantly improved contrast for early-stage cancer lesions, under visual detection of live animals with distended cheek pouches. The red-shifted absorption of the cyclen-based lanthanide chelates, allowed for the use of innocuous wavelengths of light (320 nm-360 nm) and glass optics. Detection of reddish-pink light on a blue background repetitively gave extraordinarily bright, localized fluorescence in animals with oral cancer. It is also noteworthy that normal animals treated with this agent were devoid of detectable fluorescence, as was the animal pouches containing benign (inflammation) lesions.

EXAMPLE 2

A tri-functional cyclen-based lanthanide chelate may be used to facilitate molecular imaging and allow site-specific delivery. This tri-functional chelate is conjugated, via standard linking chemistry to a carboxylate group, is light sensitized through the antenna and is a strong ligating complex through the phosphonate pendent arms and heterocycle. This is a facile and efficient synthesis that can be used to make numerous imaging agents. In addition, the resulting 6-substituted quinaldines have light stability and are very inexpensive to prepare.

Method of Making

The general synthesis used to accomplish this task is shown in Scheme II and provides a vehicle to make numerous molecular imaging agents for targeted delivery, all of them having unique and improved absorption properties.

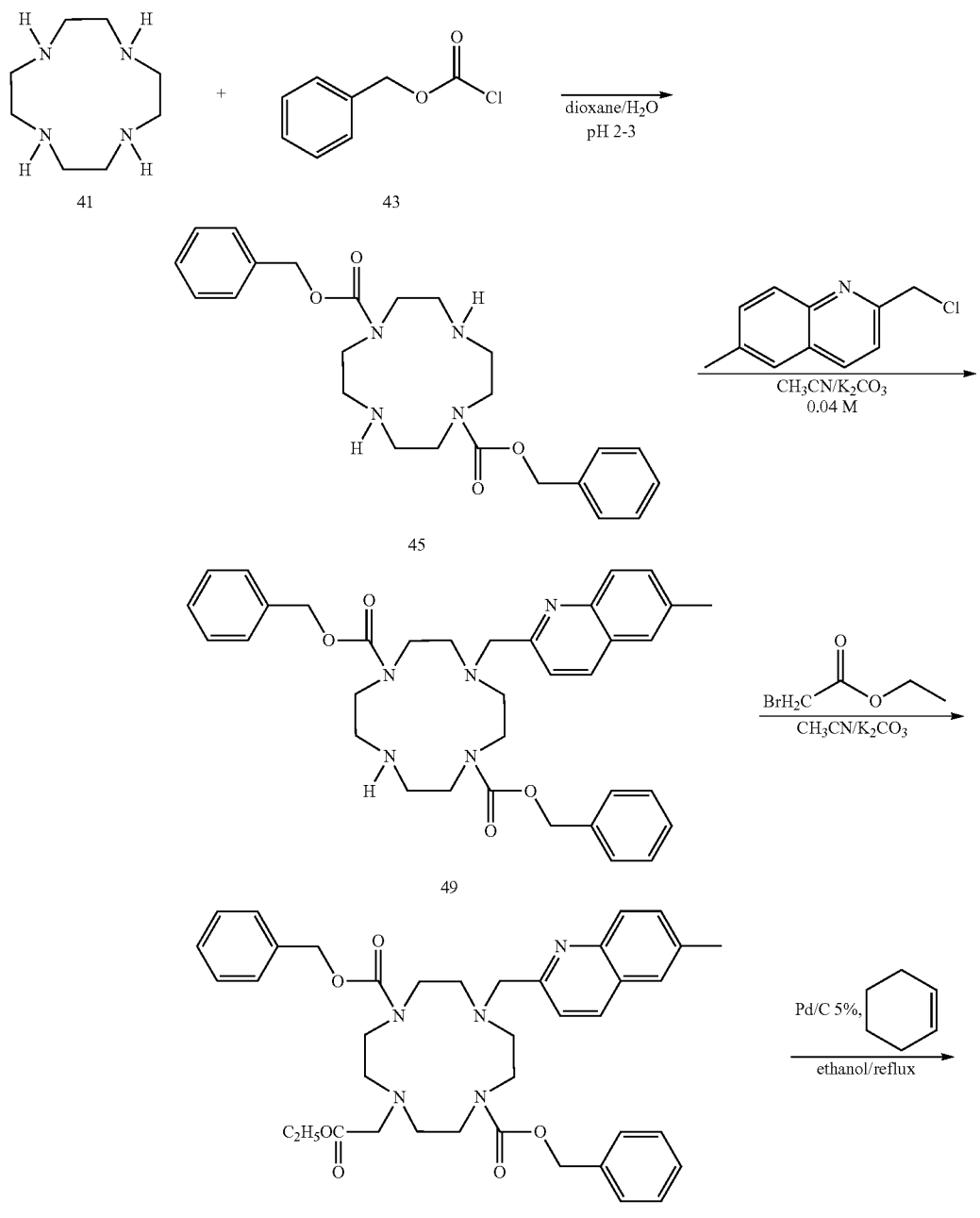

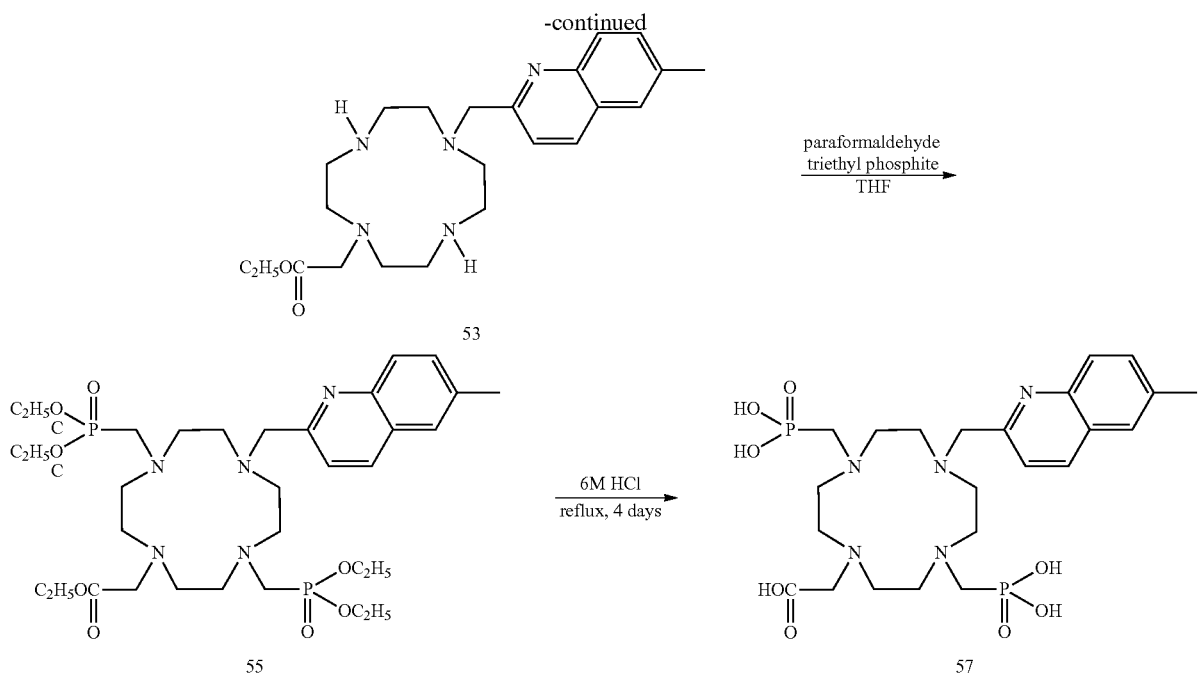

As depicted in Scheme II, the synthesis of a carboxylate derivation of a cyclen-based lanthanide chelate is produced using the following method. First, 1,7-Bis(bezyloxycarbonyl)-1,4,7,10-tetraazacyclododecane 45 is formed by the following process. To a large round-bottom flask 2.5 grams of 1,4,7,10 tetraazacyclododecane (cyclen) 41 was dissolved in 18 mL of H$_2$O and the pH was adjusted to 3 via the addition of 5 mL of 6M HCl. Next, 15 mL of 1,4 dioxane was added to the reaction mixture. Benzylchloroformate 43 (6.4 g) was dissolved in 1,4 dioxane (15 mL) and allowed to slowly drip into the reaction flask from an addition funnel over a period of 5 hours. The pH is maintained between 2-3 by the addition of 2M NaOH via a separate addition funnel. After the addition was complete, solvents were removed via rotary evaporation yielding a tan solid. The solid residue was extracted with dry Et$_2$O (4×50 mL) to remove any 1,4,7,10-tetrakis(benzyloxycarbonyl)-1,4,7,10-tetraazacyclododecane. NaOH (20% w/v, 25 mL) was added to the remaining residue and the aqueous mixture was extracted with Et$_2$O (4×50 mL). The organic fractions were collected, rewashed with NaOH (5% w/v) and dried over MgSO$_4$ Solvents were removed via rotary evaporation and dried under high vacuum to yield a colorless viscous oil (5.46 g).

In a medium round-bottom flask 0.500 grams of the resulting 1,7-Bis(bezyloxycarbonyl)-1,4,7,10-tetraazacyclododecane 45 was dissolved in 300 mL of dry CH$_3$CN. Dry K$_2$CO$_3$ (0.500 g) was added to the reaction mixture and allowed to stir. In one part, 0.218 grams of 2-chloromethylene-6-methyl quinoline 47 was added. The reaction was allowed to stir at 40° C. for four days. Reaction volume was reduced via rotary evaporation and the resulting crude was purified on a silica gel column eluting with a 30:1:0.1 mixture of methylene chloride, methanol, and ammonium hydroxide. Desired product was obtained in 80% yield.

In a medium round-bottom flask 0.500 g of the resulting 1,7-Bis(benzyloxycarbonyl)-4-(2-methylene-6-methyl quinoline)-1,4,7,10-tetraazacyclododecane 49 was dissolved in 300 mL of dry CH$_3$CN. One equivalent of ethyl bromoacetate was added in one part and the reaction was allowed to stir for 24 hours at rt. Desired product was isolated (78% yield) on a silica gel column eluting with a 75:4:1 mixture of chloroform, methanol, and ammonium hydroxide.

A solution of the resulting 1,7-Bis(benzyloxycarbonyl)-4-(2-methylene-6-methyl quinoline)-10-(ethylene acetate)-1,4,7,10-tetraazacyclododecane 51 (5 grams) in absolute ethanol was mixed with cyclohexene (5 molar excess per benzyloxycarbonyl group). Next, 1.00 gram of 5% Pd/C catalyst was added. The mixture was stirred at reflux for 4 hours. The mixture was concentrated via rotary vaporation, taken up in ethylacetate and then extracted with 20% NaOH. Organic layer was dried yield concentrated via rotary vaporation giving the desired product in 95% yield.

To a stirred solution of paraformaldehyde and triethylphosphite (2 equivalents respectively) in THF, 0.500 grams of the resulting 1-(2-methylene-6-methyl quinoline)-7-(ethylene acetate)-1,4,7,10-tetraazacyclododecane 53 was added in one part. The reaction was allowed to stir for three days at room temperature under positive N$_2$ pressure. Solvents were removed via rotary evaporation. Desired product was isolated (83% yield) using a silica gel column and eluting with a 20:4:1 mixture of chloroform, methanol, and ammonium hydroxide.

To 200 mL of 6M HCl, 0.500 grams of the resulting 1-(2-methylene-6-methyl quinoline)-4,10 Bis(methylene-phosphonicdiethylester)-7-(ethylene acetate)-1,4,7,10-tetraazacyclo-dodecane 55 was added and allowed to stir at room temperature for 3 days. The desired product was isolated (94%) via azeotropic distillation with water. The carboxylate derivate of the lanthanide chelate 1-(2-methylene-6-methyl quinoline)-4,10 Bis(methylene-phosphonic acid)-7-(acetic acid)-1,4,7,10-tetraazacyclododecane 57 was produced.

EXAMPLE 3

Subsequently, the cyclen-based lanthanide chelates obtained in EXAMPLE 2 can be conjugated to PK-11195 to give specificity of uptake and numerous signatures for co-registration diagnostic imaging and surgical guidance. Previous studies on PK-11195 and a closely related compound indicate that it can be conjugated, will retain it biological activity and can therefore be used as a molecular imaging agent to detect blastoglioma and study mitochondrial function.

Method of Making Conjugable PK-11195

An Ln-PK-11195 conjugated chelate (Eu-QM-CTMC-PK11195) can be prepared and will provide useful fluorescence and MR images. Scheme III illustrates a process for making a small quantity of high purity conjugable PK-11195.

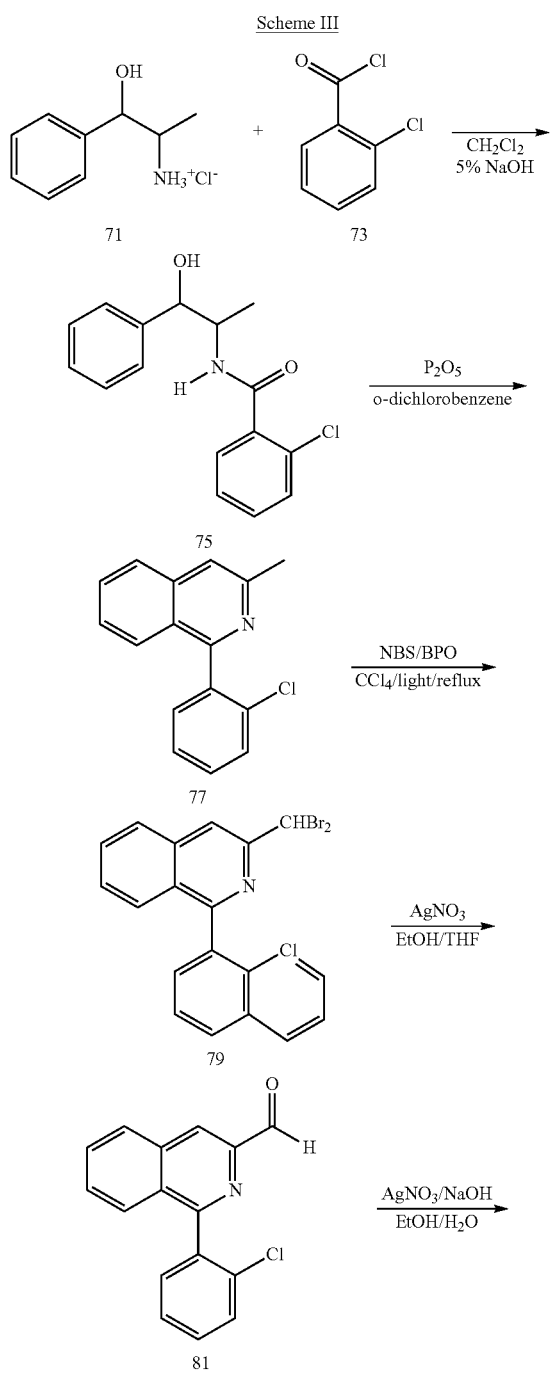

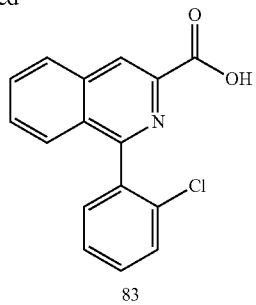

A conjugable form of PK-11195 is formed by first producing 2-Chloro-N-(2-hydroxy-1-methyl-2-phenylethyl)benzamide 75 by the following process. To an ice-cooled mixture of Norephedrine 71 HCl in $CH_2Cl_2$ (120 mL, 5.2 g, 27.8 mmol) and 40 mL of 5% NaOH was added dropwise a solution of 2-Chlorobenzoyl Chloride 73 (7.5 g, 28.1 mmol) in 15 mL $CH_2Cl_2$. The mixture was stirred for 4 hours at 0° C. The solvent was removed in vacuo. The residue was washed with $H_2O$ then dried and recrystallized from EtOH to afford 90% 9.5 g of a white solid.

Next, 1-(2-chlorophenyl)-3-methylisoquinoline 77 is formed by the following process. A mixture of 2-Chloro-N-(2-hydroxy-1-methyl-2-phenylethyl)benzamide 75 (9.5 g 24.9 mmol) and $P_2O_5$ in o-dichlorobenzene (150 mL) was refluxed overnight. Upon completion, the reaction was cooled to room temperature and then it was chilled to 0° C. 300 mL of $H_2O$ was cautiously added. The resulting dark solution was then washed with toluene (2×50 mL). The aqueous layer was cooled to 0° C. and made to pH 11 with 50% NaOH. The resulting mixture was then extracted with toluene (4×50 mL). The toluene layer was dried, filtered and concentrated in vacuo. The residue was then recrystallized from benzene to afford a white solid. (6.68, 80%).

Then 1-(2-clorophenyl)-3-isoquinolinecarboxylic acid 81 is formed by the following process. A mixture of 1-(2-clorophenyl)-3-methylisoquinoline 77 (6.68 g, 19.88 mmol), N-bromo-succinimide (NBS) (8.896 g, 19.98 mmol), and benzoyl peroxide (BPO) (0.57 g) in $CCl_4$ was heated to reflux while being illuminated by a flood lamp for 5 hours. The reaction was cooled to room temperature and filtered. The filtrate was washed with saturated $NaHCO_3$ (1×40 mL), dried with $Na_3SO_4$, filtered and concentrated in vacuo. The crude dibromide yellow product 79 was used in the next step. To a refluxing solution of the crude dibromide 79. (10.13 g) in EtOH (140 mL) and THF (70 mL) was added dropwise a solution of $AgNO_3$ (10.595 g) in $H_2O$ (6 mL). The mixture was refluxed for 1 hour and filtered hot. The filter cake was washed with hot THF (2×20). The combined filtrate was concentrated in vacuo to give crude 1-(2-clorophenyl)-3-isoquinolinecarboxaldehyde as a dark yellow oil. (9 g) This oil was used without purification. To a solution of the crude aldehyde in absolute EtOH (100 mL) was slowly added a solution of $AgNO_3$ (11.11 g) in 10 mL $H_2O$. to this stirred solution was added dropwise a solution of NaOH (9.43 g) in $H_2O$ (140 mL). The resulting black slurry was stirred at room temperature for 2 hours. The solution was then filtered through a Celite column. The filter cake was washed with ether. The ether was evaporated and the aqueous solution was made slightly acidic with concentrated HCl. The precipitate was collected by filtration, then washed with H$_2$O. It was then recrystallized from CH$_3$CN affording pale yellow crystals (2.63 g, 35%).

Finally, 1-(2-clorophenyl)-N-heptylamino-3-isoquinolinecarboxamide 83 (PK11195) is formed by the following process. To a mixture of 1-(2-clorophenyl)-3-isoquinolinecarboxylic acid 81 (0.1868 g, 0.5 mmol) and bezotriazol-1-yloxy-tris(dimethylamino)phosphonium hexafluorophosphate (BOP) (0.2219 g, 0.5 mmol) 1,7 diaminoheptane in DMF (8 mL) and triethylamine (0.42 mL, 4.5 mmol) was added. The reaction was stirred under positive N$_2$ at room temperature for 7 hours and quenched with the addition of H$_2$O (10 mL). The mixture was extracted with CH$_2$Cl$_2$ (3×15 mL). The organic layer was dried with MgSO$_4$, filtered and concentrated in vacuo. Residue was purified on a silica column with 1:1 ethyl acetate, hexanes. (0.1237 g, 65%).

Conjugation of Cyclen-Based Lanthanide Chelate with PK11195

Conjugation of 1-(2-methylene-6-methyl quinoline)-4,10 Bis(methylene-phosphonic acid)-7-(acetic acid)-1,4,7,10-tetraazacyclododecane to PK11195 is performed by the following process. Scheme IV shows a preferred synthesis and conjugation of a small quantity of a Ln-Q-Y-CTMX to PK-11195 complex.

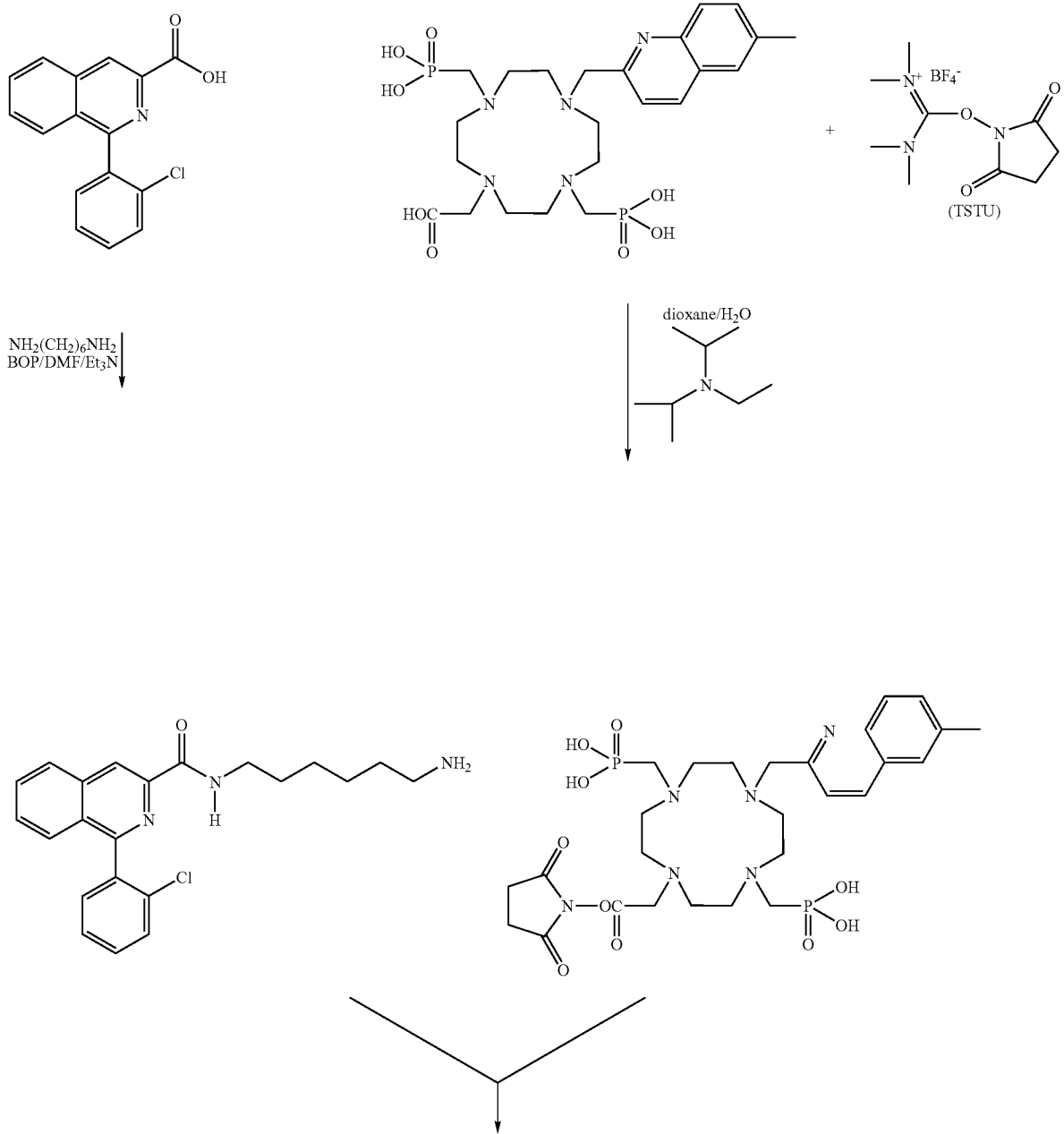

-continued

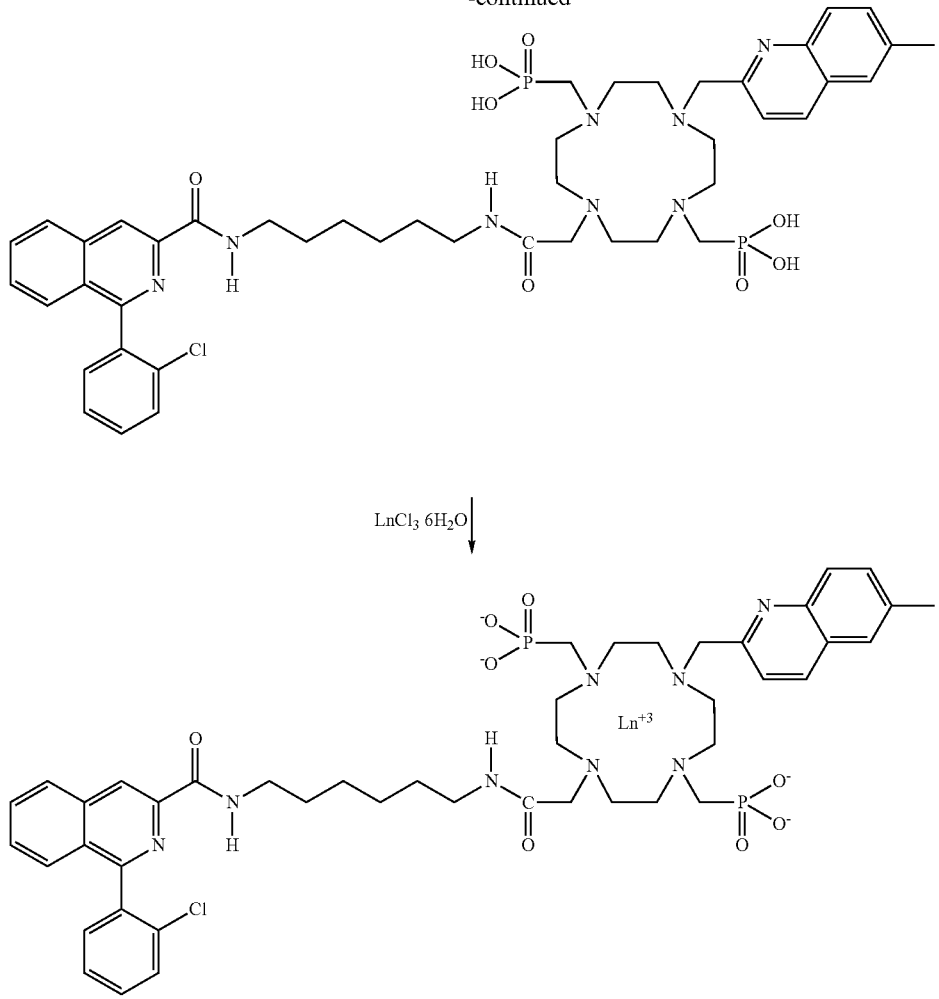

107

The specific procedures used are described herein. The complex 1-(2-methylene-6-methyl quinoline)-4,10 Bis(methylene-phosphonic acid)-7-(methylene-1-(2-chlorophenyl)-N-hexyl-3-iosoquinoline carboxamide)-1,4,7,10-tetraazacyclododecane 107 is prepared using the following process. To a stirring mixture of 1-(2-methylene-6-methyl quinoline)-4,10 Bis(methylene-phosphonic acid)-7-(acetic acid)-1,4,7,10-tetraazacyclododecane 57 and O—(N-Succinimidyl)-N,N,N',N'-Tetramethyluronium tetrafluoroborate (TSTU) (1 equivalent of each) in a water-dioxane solution, a mixture of 1-(2-chlorophenyl)-N-hexylamino-3-iosoquinoline carboxamide and one equivalent of triethyl amine was added slowly via canula. The resulting reaction mixture was allowed to stir at room temperature under positive $N_2$ pressure for 4 hours. The desired product was isolated (40%) on a silca gel column eluting with a 50:4:1 mixture of chloroform, methanol, and ammonium hydroxide.

Testing Results

Figure 5:
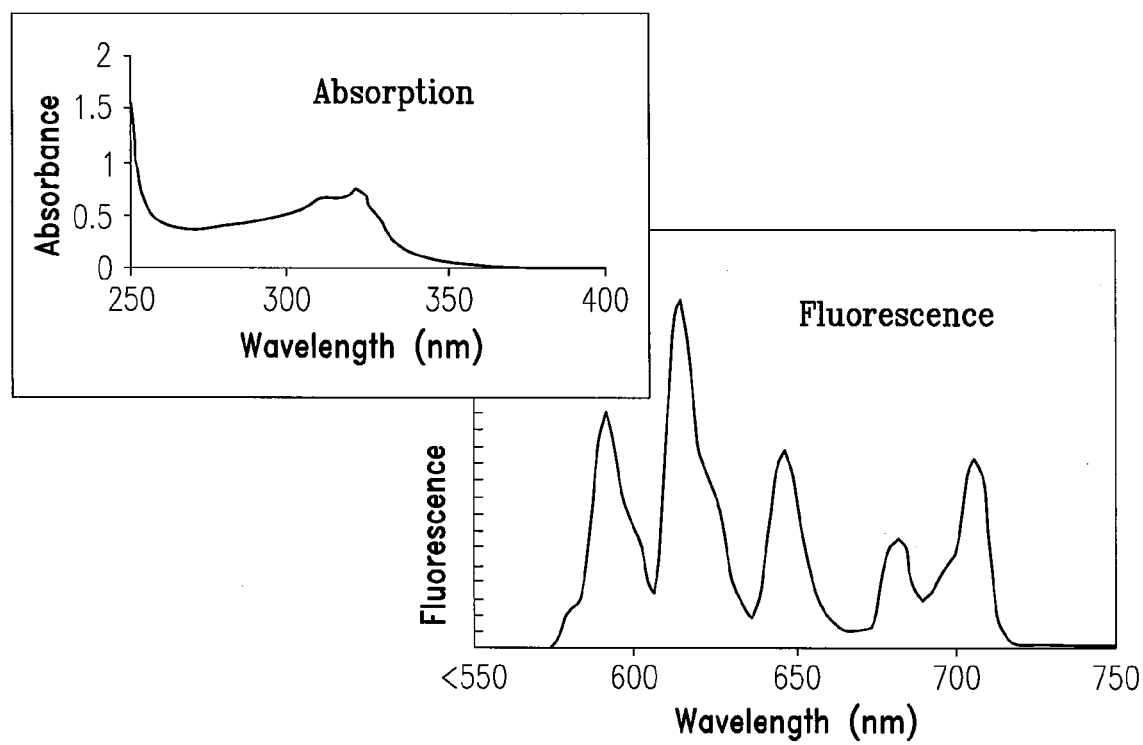
FIG. 5 is a graph showing the absorption and emission spectra for the Eu-Q{M}-CTMC-PK11195 chelate.

FIG. 5 shows the absorbance spectrum for one of the proposed agent obtained using a Shimadzu 1601 UV/Vis spectrophotometer. The sample was scanned from 400-250 nm with a sampling interval of 0.1 nm. Slit-width was 2 nm. Two distinct absorbing features were clearly visible, presumably, one for the quinoline sensitizer and the other for PK11195. Performing serial dilutions and preparing a Beer's law calibration plot provided a value of the molar absorptivity ($\epsilon \approx 3,500$ L/mol.cm). As seen in FIG. 16, the fluorescence spectrum of Eu-QM-CTMC-PK11195 was measured using an SLM 4800c fluorometer (Aminco) (0.5 nm resolution, 1 nm step size). Complex was excited at 320 nm and the sharp fluorescent emission bands were observed from 580 nm to 720 nm corresponding to the atomic fluorescence of $Eu^{3+}$ ($^5D_0 \rightarrow {}^7F_0$, $^7F_1$, $^7F_2$, $^7F_3$, $^7F_4$, $^7F_5$).

C6 Glioblastoma Cell Testing

Preliminary observations regarding the use of Ln-QM-CTMC-PK11195 to selectively image C6 glioblastoma, or brain cancer cells, are herein presented. Additionally, by simply changing the chelating ion in the complex, from $Eu^{3+}$ to $Gd^{3+}$, MR contrasts are obtained that are comparable to the standard clinical MRI perfusion agent, Magnevist™.

Figures 6A, 6B:
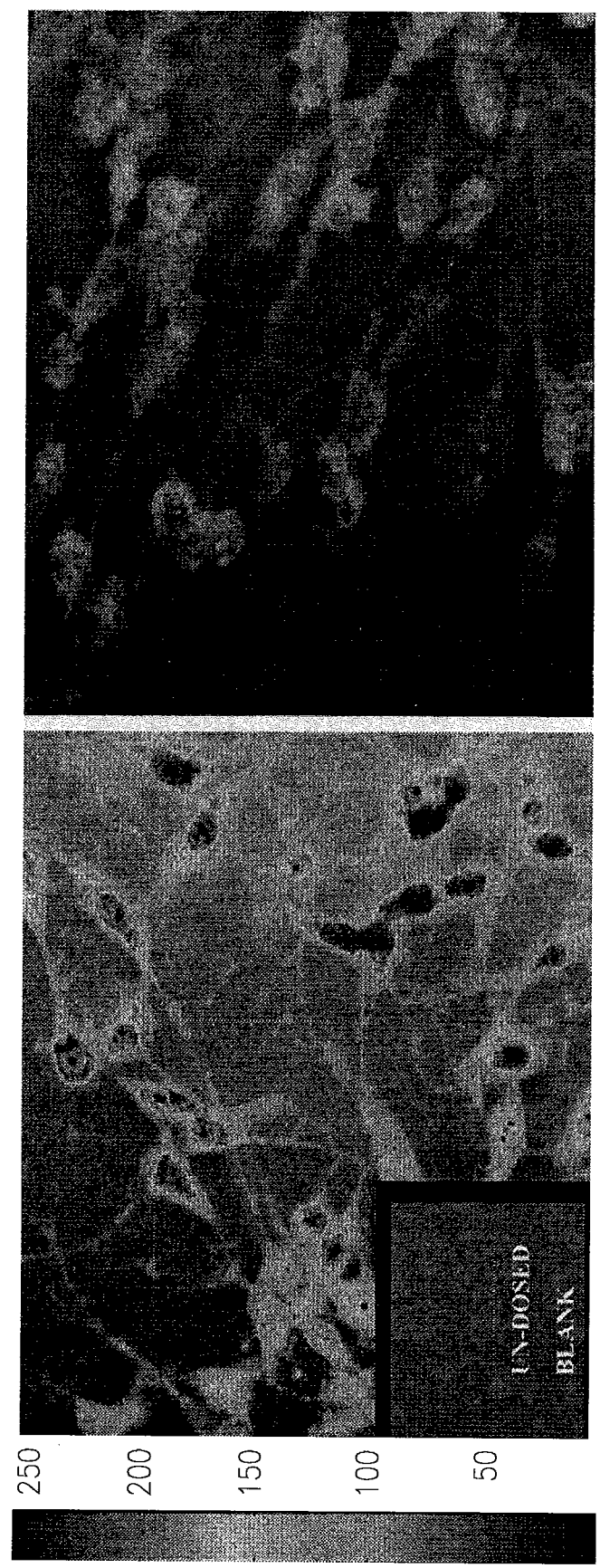
FIG. 6A depicts C6 glioblastoma cells after 60 minute incubation with Eu-QM-CTMC-PK11195 and viewed in fluorescence model at 40× (False light). Inset: undoes (blank) C6 glioblastoma cells.
FIG. 6B depicts C6 culture first incubated 60 minutes with Eu-QM-CTMC-PK11195, then counter incubated with PK11195 for 60 minutes.

The following testing was conducted to confirm that conjugated cyclen-based lanthanide chelates are uptaken by C6 glial cells. C6 glioblastoma cells were plated out on glass coverslips and incubated at 37° C. until just prior to confluency. Next, cells were dosed with 1 mL of a 25 µM solution of Eu-QM-CTMC-PK11195 and allowed to incubate at 37° C. for 60 minutes. At the end of the incubation time, the cells were thoroughly rinsed with saline and imaged in white light and fluorescence directly using a epi-illumination fluorescence microscope configured with an optical train consisting of a UG11 filter in the excitation path and 400 nm cutoff dichroic mirror (Chroma). Finally, fluorescence was collected through a 612 nm, 25 nm FWHM emission filter and directed onto a Photometrics PXL PVCAM cooled CCD camera. Integration time was 18 seconds for both the blank and inoculated samples. FIG. 6A illustrates the typical uptake of Eu-QM-CTMC-PK11195 by C6 glioblastoma cells (false colorized). Inset in the figure is the fluorescence blank, an un-dosed population of C6 cells of comparable density. Similar results have been obtained in multiple subsequent data sets. From FIG. 6A, one will readily note that the agent was substantially up-taken and that fluorescence seems to be emanating from distinct internal regions, suggesting specific organelle localization. The actual organelle(s) responsible for this localization have yet to be fractionally isolated and identified. The images presented were taken at 40× with an ultrafluar object (NA=0.5).

Figure 7:
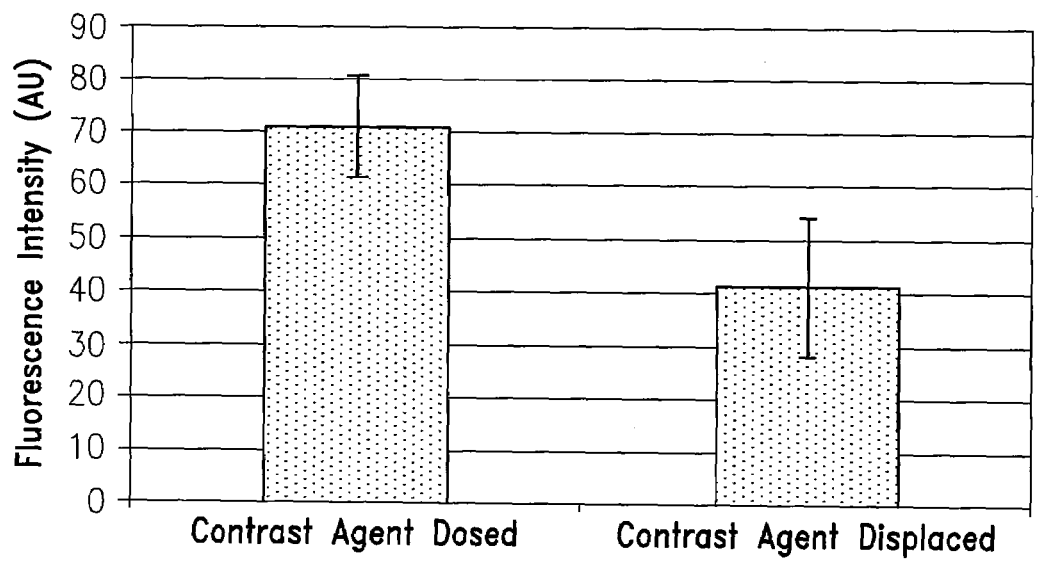
FIG. 7 shows the average fluorescence attenuation of C6 glioblastoma as a function of PK11195 displacement of contrast agent from PBR.

After demonstrating that the agent was significantly up-taken by cells, the next step was to determine whether the agent was truly binding the PBR or not. Cells were dosed with Ln-QM-CTMC-PK11195, the fluorescence intensity was quantified, then the same cells were incubated with the native PBR ligand (PK11195) and the reduction in fluorescence intensity was measured to determine if Ln-QM-CTMC-PK11195 was displaced from the PBR. The results of this experiment can be seen in FIG. 6B. This picture is the subsequent image (false colorized) after first dosing with Eu-QM-CTMC-PK11195, then counter incubation with excess native PK11195. Note, due to the procedure used to rinse the cells between incubations, minor repositioning of the cells occurs. For this reason, FIG. 6A and FIG. 6B look dissimilar despite being approximately the same region on the slide. As shown in FIG. 7, the average intensity attenuation (triplicate experiments) was determined to be 37%. This value is significant because only a six-fold excess of PK11195 was used to displace the present contrast agent, whereas the standard method employs a 100 fold excess of PK11195 to demonstrate quantifiable fluorescence attenuation and show PBR ligand functionality. By quantifying the attenuation of fluorescence upon displacement of Ln-QM-CTMC-PK11195 with the native PBR ligand PK11195, results indicate that the conjugated chelates is functioning as a true PBR ligand. These results seem to indicate that Eu-QM-CTMC-PK11195 is displaced by PK11195 and is functioning as a PBR ligand.

At the present time, four commercially available, non-radioactive lanthanide derived chelates are widely used as contrast enhancement agents for magnetic resonance imaging. A significant volume of literature shows that these complexes of $Gd^{3+}$, particularly those derived from and analogous to the present lanthanide chelate complexes, have the necessary properties to be good MRI contrast agents. For example, the macrocyclic derivatives (DOTAREM and PROHANCE) display a greater degree of thermodynamic inertness relative to the acyclic analogs, which means that they can be subjected to extreme environments for prolonged periods without degradation. These chelates also exhibit a high degree of kinetic inertness making them suitable for in-vivo applications and have been exhaustively studied and evaluated and are routinely used in humans at high dosages. LD50's are typically in the 10 mmol/kg range in the rat model for PROHANCE. These compounds are classified as perfusion agents and are administered IV at dosage levels ranging from 0.05-3 mmol/kg.

Recent studies to determine how the present cyclen-based lanthanide chelates will perform as contrast agents with MRI have been performed. In preliminary work, $Gd^{3+}$ chelates of the contrast agents (Gd-Q-Me-CTMX) were prepared and relaxivity experiments were performed. The water proton relaxivity ($r_1$), when observed at RT and 20 Mz, was found to range from $r_1$=1.4-3.2 $mM^{-1}s^{-1}$ with q=0 or 1. These results indicate that the quinoline-containing cyclen-based chelates should perform similarly to currently available MRI agents like PROHANCE. Experiments were conducted to show the MRI contrast possible with four of the un-conjugated cyclen-based lanthanide chelates. Here 2 mM solutions were placed in 3 mm tubes with a smaller tube containing buffer alone and imaged on the 11.7 T system at Caltech Biological Imaging Center using a standard spin echo sequence. For contrast agents currently on the market, about 50% of their relaxivity is due to the outer-sphere component, with the literature clearly showing that even q=0 complexes can be used effectively in tissues. These complexes generally show improved performance when bound to interstitial space or circulating proteins or to cell surfaces.

Figure 8:
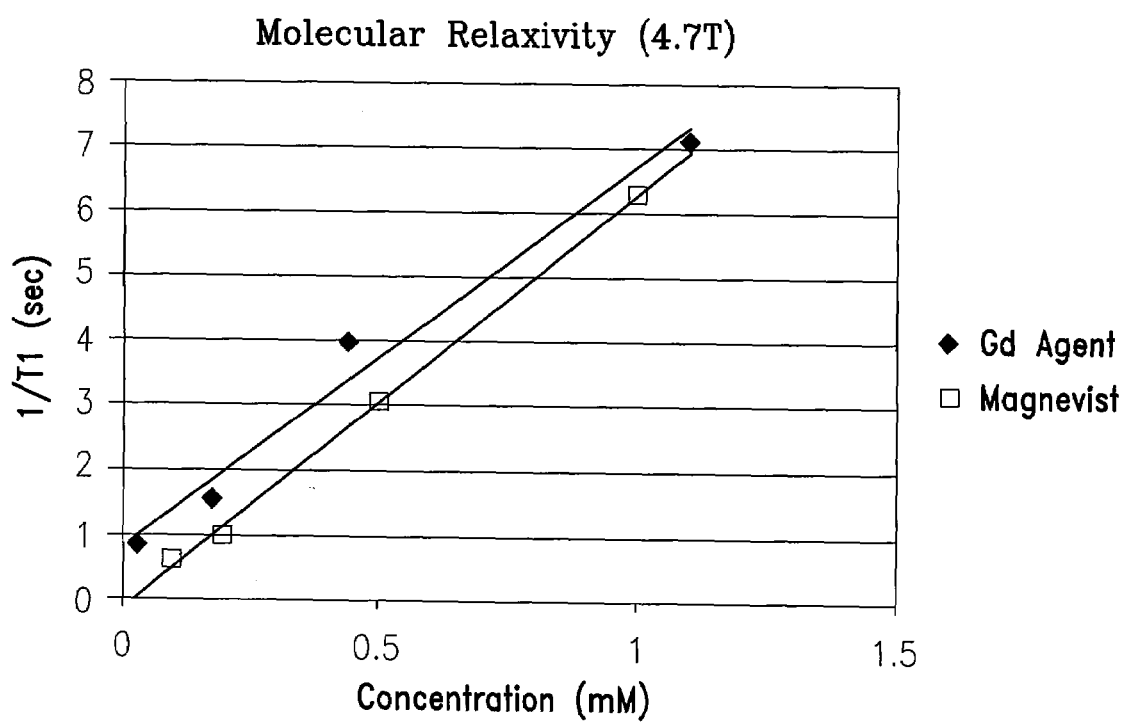
FIG. 8 is a graph demonstrating the relaxivity of Gd-PK11195 and Magnevist.
Figure 9:
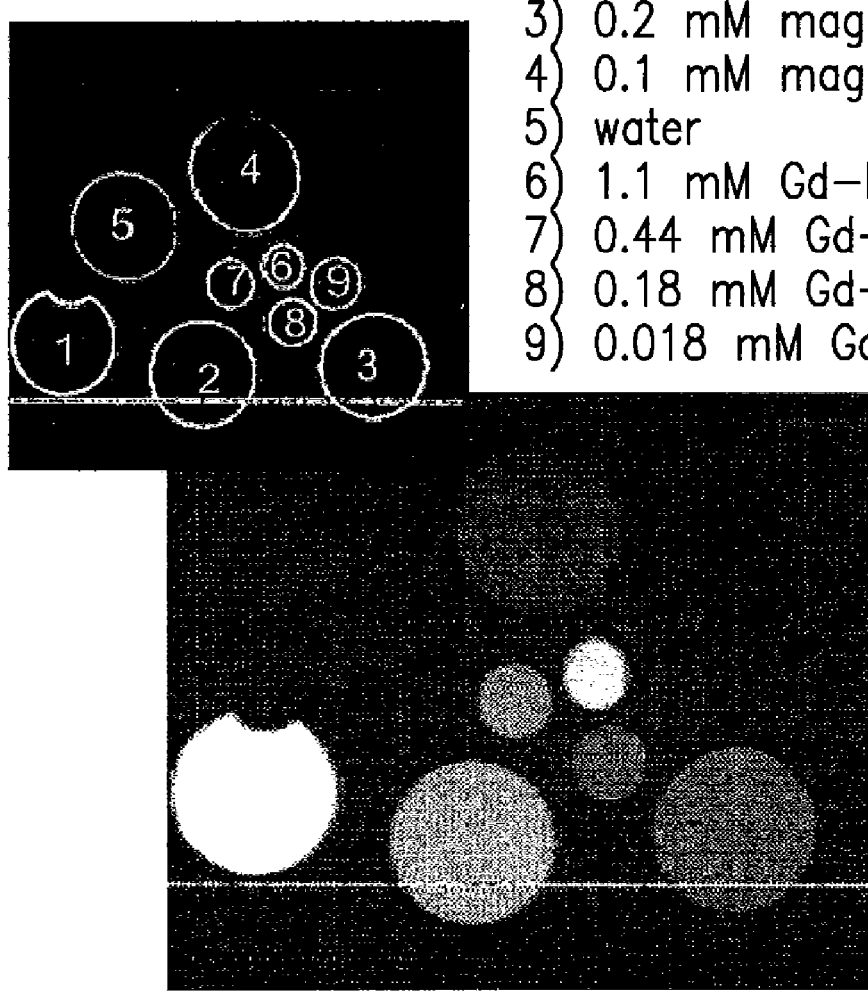
FIG. 9 shows the MRI contrast for Gd-PK11195 and Magnevist.
Figure 10:
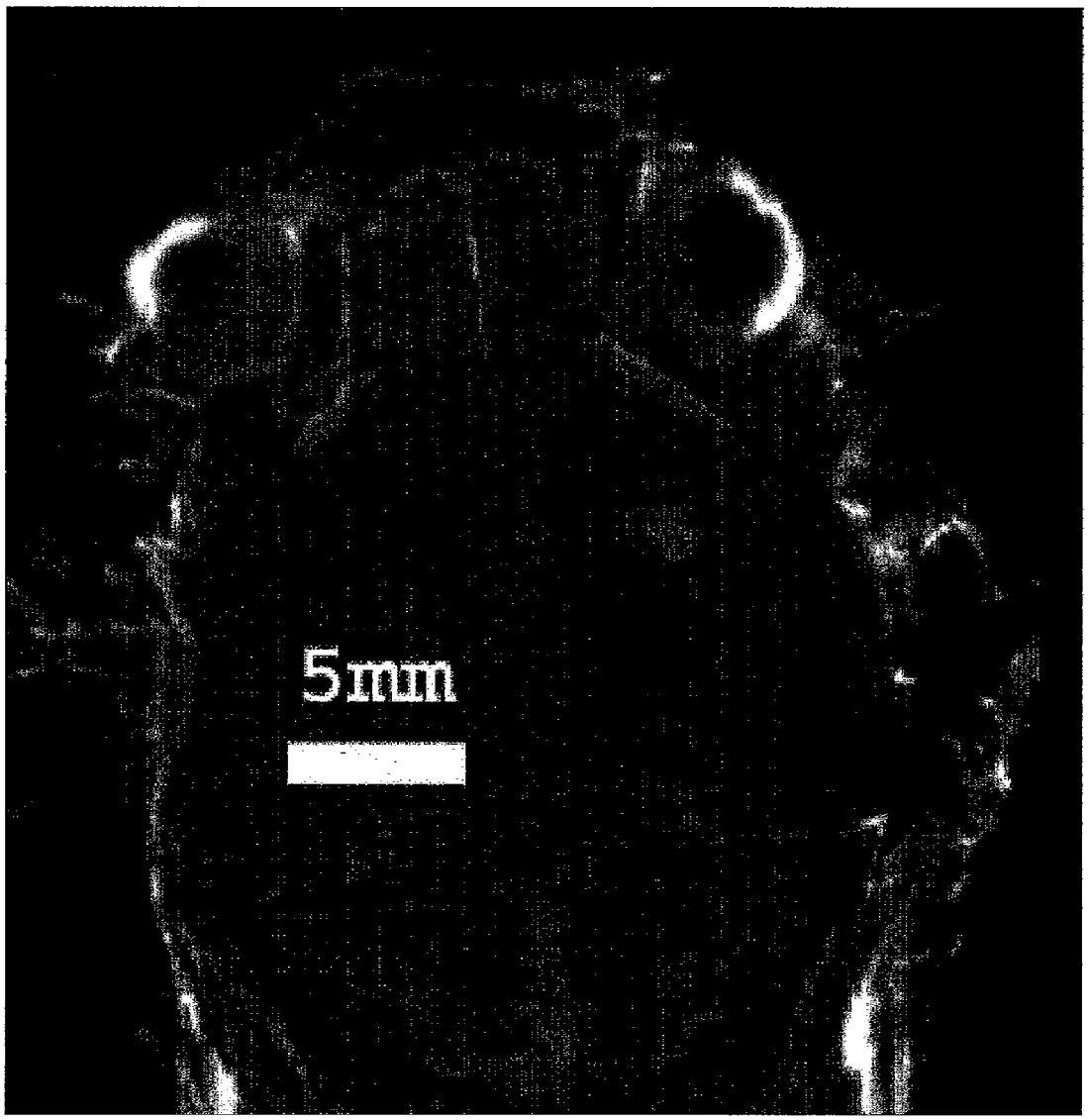
FIG. 10 shows a contrast enhanced high-resolution in-vivo imaging at 78×78×200 µm of mouse brain glioma in the 11.7 T MRI.

The relaxivity of the $Gd^{3+}$ chelate of Ln-PK-11195 was also evaluated. FIG. 8 shows the results of this determination, allowing a direct comparison to an existing agent ($r_{Gd=PK}$=5.94 $mM^{-1}sec^{-1}$ vs. $r_{Magnevist}$=6.45 $mM^{-1}sec^{-1}$). Under different conditions and using a different magnet at 20 Mhz, $r_1$=4.8 $mM^{-1}sec^{-1}$, the $T_1$ weighted proton imaging experiments, done at 4.2 T and using a $T_1$ weighted spin-echo sequence (TE/TR=12/400 msec), provide a more definitive illustration that the present contrast agents provide MRI contrast enhancement. FIG. 9 is nine images in which TE=12 msec was kept constant and TR was varied 100-3000 msec. Brightness for solutions of sequentially decreasing concentration of Ln-PK-11195 and Magnevist show that the present contrast agent can be used for MRI. Enhanced relaxivity is also expected for this compound upon cell binding or uptake. FIG. 10 shows the possible resolution as generated from MRI of a mouse brain by the co-PI Dr. Moats.

Figure 11:
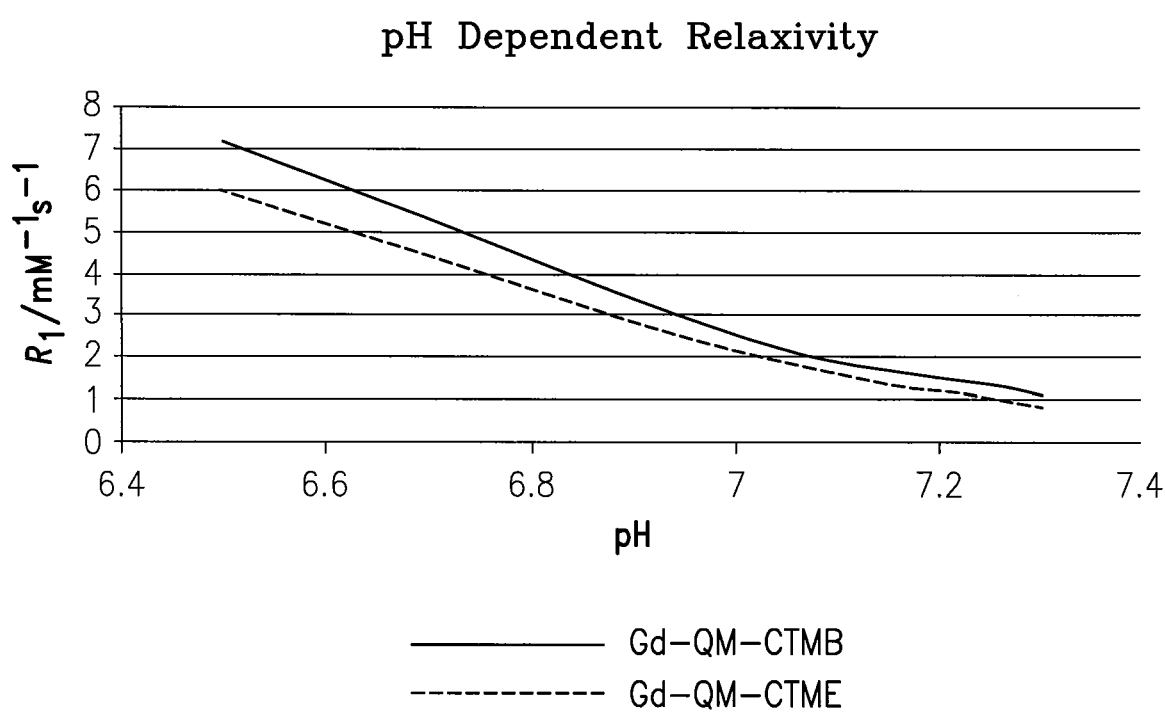
FIG. 11 is a graph demonstrating the pH dependent relaxivity of Gd-QM-CTME and Gd-QM-CTMB.

Both luminescent cyclen-based lanthanide chelates and those primarily yielding MR signatures have been shown to be sensitive to changes in pH. Luminescent probes used for sensing pH changes typically detect changes in the fluorescence lifetime of the lanthanide ion as a function of pH. Analogously, an MR contrast agent has recently been reported in which the water proton relaxivity could be modulated via changes in pH. In both cases by changing the pH in a given system, one can envision agents with enhanced contrast. Similarly, one can use these pH sensitive contrast agents as molecular reporters of various proton density gradients, with both industrial (monitoring industrial processes) and biomedical applications (tissue/disease mapping). Indeed our preliminary relaxivity measurements have also indicated that it might be possible to use the present molecular imaging agents as pH sensors. For example, FIG. 11 shows that both Gd-Q{M}-CTME and Gd-Q{M}-CTMB exhibit a pH relaxivity change (pH response) over physiologically interesting range.

The molecular imaging agent Ln-QM-CTMC-PK11195 addresses the need for glia-specific stain. By targeting the over-expressed PBR in human brain tumors, the Eu-PK-11195 contrast agent allows the discrimination of normal tissue versus infiltrating disease. A typical example of a thinly sliced cross-section of surgically resected human brain tumor (ex-vivo) that was paraffin fixed, incubated with the new molecular imaging agent and imaged using an epi-fluorescence microscope at 40× was prepared. Current data indicates that the ligand does mark glioblastoma multiforme cells. The paraffin sections of glioblastoma incubated with ligand demonstrate this potential as well as the pleomorphic morphology of glioma cells.

Cellular up-take and displacement of Ln-QM-CTMC-PK11195 in PBR over-expressing C6 glioblastoma cells has been demonstrated. Thus, the $Eu^{3+}$ chealte, when up-taken by cells will produce bright fluorescence which is easily detectable with standard instrumentation. Also, complexes with $Gd^{3+}$ Ln-QM-CTMC-PK11195 will generate a quantifiable MR signature which is comparable in brightness to commercially available and clinically used products.

Breast Cancer Studies

Figure 12:
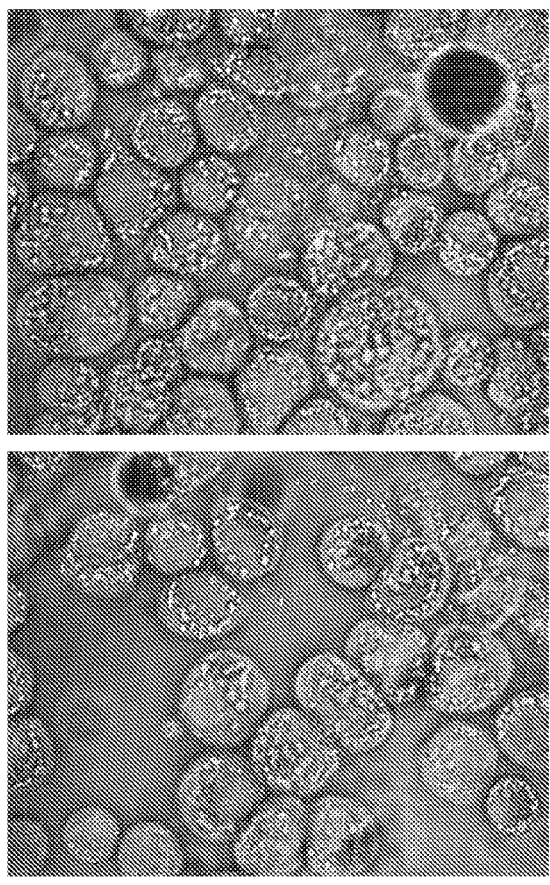
FIG. 12 shows images of un-dosed TTU-1 cells.
Figure 12:
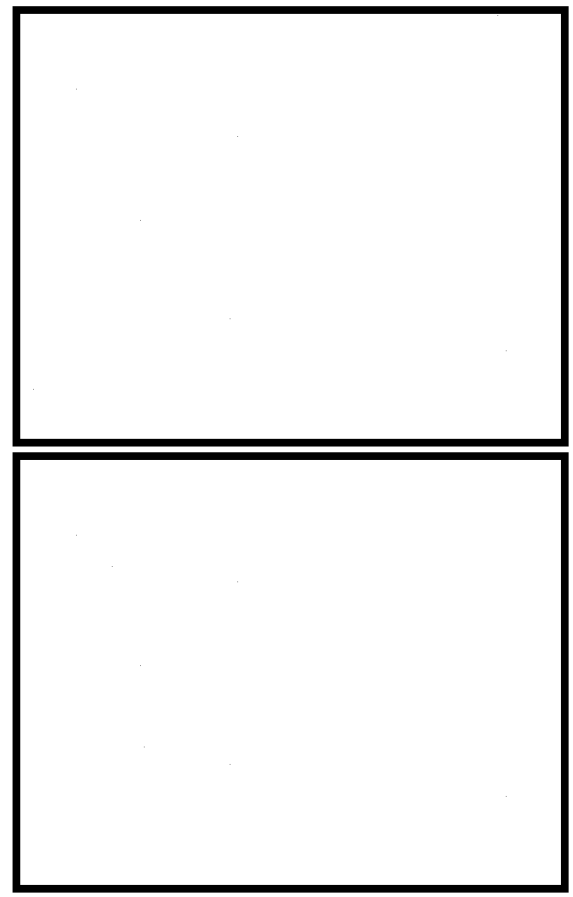

The cyclen-based lanthanide chelates conjugated with PK11195 may also be used to selectively demarcate PBR over-expressed breast cancer tissues. This has been demonstrated by dosing two different human cell lines, TTU-1 and MDA-231 with Ln-QM-CTMC-PK11195. FIG. 12 shows the white light and auto-fluorescence image of un-dosed TTU-1 cells. The images stem from two different regions of the same slide. To accomplish the imaging, the cells were grown to near confluency on glass coverslips. Next, the media was removed and the cells were dosed for 30 minutes with 0.10% saline. Finally, the cells were wet-mounted onto a glass slide and images in white-light and fluorescence modes. The undosed cells exhibit very little auto-fluorescence at the utilized 30 second integration time.

Figure 13:
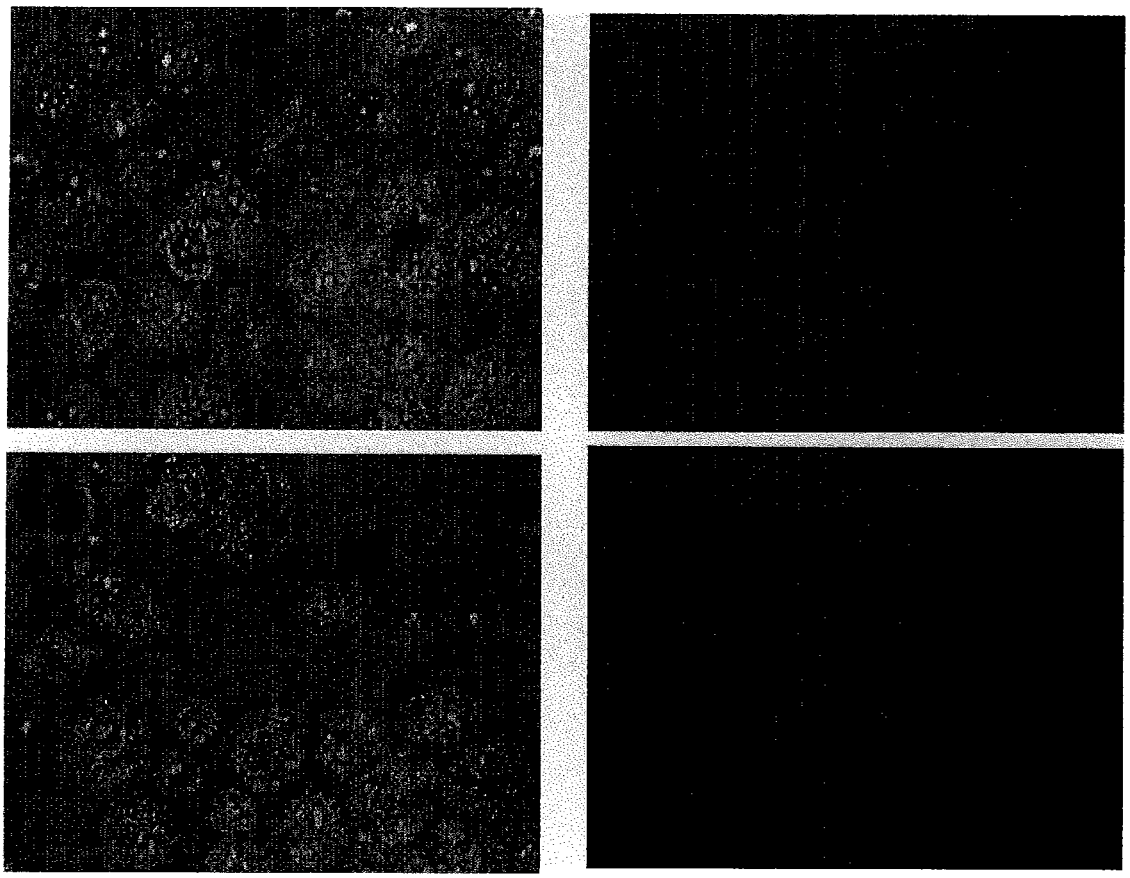
FIG. 13 shows images of Eu-QM_CTMC-PKI 195 dosed TTU-1 cells.

The next step was to dose the cells with the contrast agent. FIG. 13 shows the white light images and the corresponding fluorescence images after dosing the cells with Eu-QM-CTMC-PK11195. The imaging was accomplished by growing the cells as stated above, then dosing them with a 50 µM solution of the contrast agent for 40 minutes. After the incubation time, the cells were rinsed with 0.10% saline and wet mounted for imaging. As with the auto-fluorescence images, the integration time was set to 30 seconds. The contrast ratio for the dosed TTU-1 cells over the background is estimated to be approximately 10:1.

Figure 14:
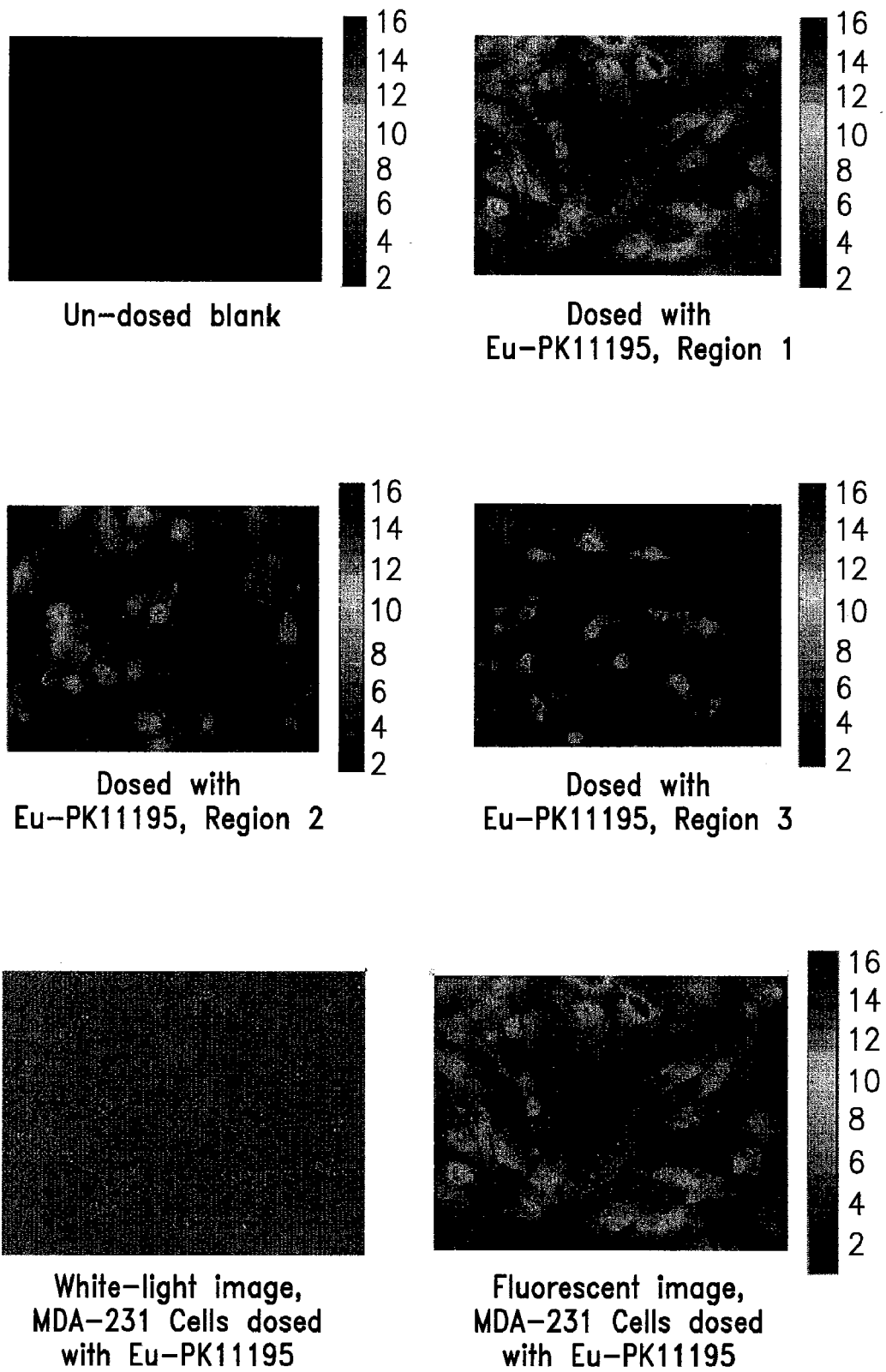
FIG. 14 shows MDA-231 cell images of breast cancer cells-Ln-PK11195.

A parallel series of experiments was conducted involving the use of a second human breast cancer cell line, MDA-231. It has been previously determined that these particular cells constitute one of the highest PBR expressing breast cancer cell lines known. MDA-231 cells were grown, dosed and imaged as described above. FIG. 14 shows the results from dosing the MDA-231 cells with Ln-PK11195 for 40 minutes. Camera integration time was set to 30 seconds. From FIG. 14, the MDA-231 cells are uptaking the contrast agent. The contrast ratio for the dosed MDA-231 cells over the background is estimated to be approximately 15:1.

It should be noted that depending on several factors including cell cycle and confluency level, the actual location of the PBRs can vary. This could potentially explain why there seems to be some fluorescence stemming from the nucleus, cytosol, and plasma membrane.

EXAMPLE 4

An alternate conjugation of 1-(2-methylene-6-methyl quinoline)-4,10 bis(methylene-phosphonic acid)-7-(acetic acid)-1,4,7,10-tetraazacyclododecane to PK11195 is prepared as follows to prepare chelates with enhanced stability and resistance to enzyme cleavage. To a stirring mixture of 1-(2-methylene-6-methyl quinoline)-4,10 Bis(methylene-phosphonic acid)-7-(acetic acid)-1,4,7,10-tetraazacyclododecane and bezotriazol-1-yloxy-tris(dimethylamino) phosphonium hexafluorophosphate (BOP) (1 equivalent of each) in dioxane-DMF solution, a mixture of 1-(2-chlorophenyl)-N-hexylamino-3-iosoquinoline carboxamide and one equivalent of diisopropyl ethyl amine (DIEA) was added slowly via canula. The resulting reaction mixture was allowed to stir at rt under positive $N_2$ pressure for 4 hours. The desired product was isolated (40%) on a silca gel column eluting with a 50:4:1 mixture of chloroform, methanol, and ammonium hydroxide.

In addition to the six-carbon linker currently used in the present Ln-PK11195 chelates, conjugated chelates with longer and shorter linker chain lengths (spacer group) may be prepared. For example, the synthesize agents may contain linker chains with 2, 4, 8 and 10 carbons.

EXAMPLE 5

Using the lanthanide metal ions $Nd^{3+}$, and $Yb^{3+}$ and the cyclen-based lanthanide chelates prepared using Scheme V, NIR absorbing and emitting complexes containing lanthanide chelates are prepared.

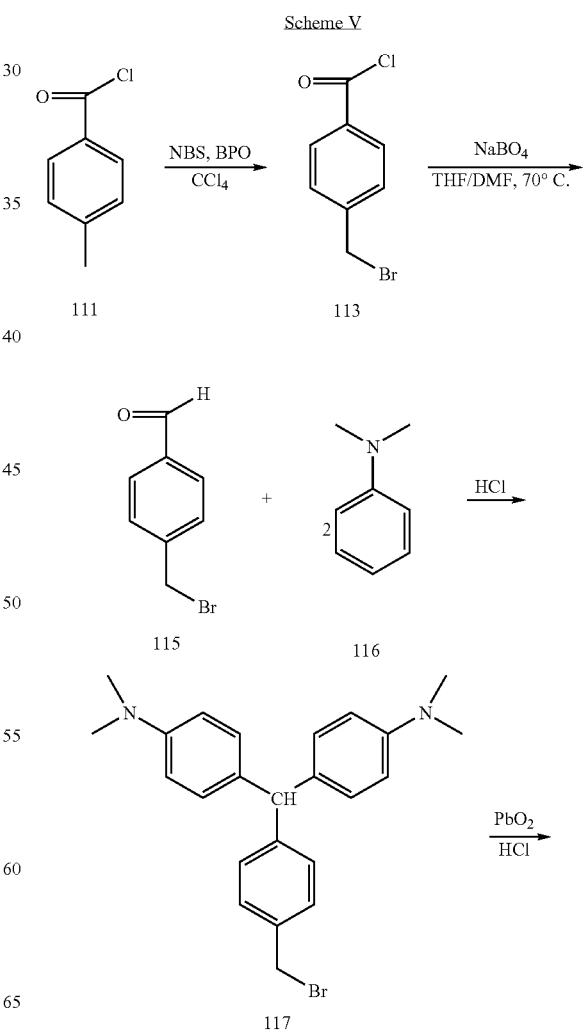

Scheme V

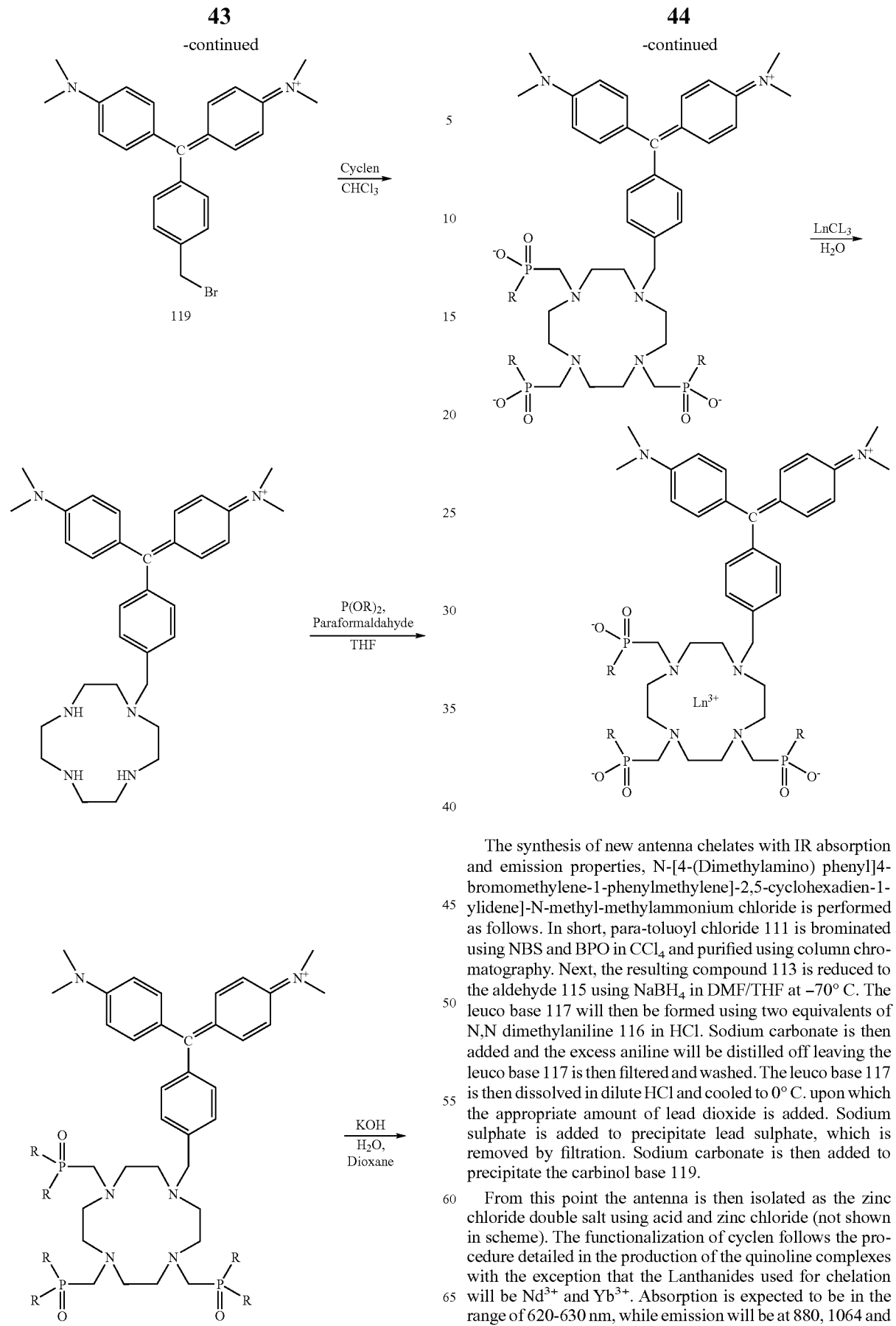

The synthesis of new antenna chelates with IR absorption and emission properties, N-[4-(Dimethylamino) phenyl]4-bromomethylene-1-phenylmethylene]-2,5-cyclohexadien-1-ylidene]-N-methyl-methylammonium chloride is performed as follows. In short, para-toluoyl chloride 111 is brominated using NBS and BPO in $CCl_4$ and purified using column chromatography. Next, the resulting compound 113 is reduced to the aldehyde 115 using $NaBH_4$ in DMF/THF at −70° C. The leuco base 117 will then be formed using two equivalents of N,N dimethylaniline 116 in HCl. Sodium carbonate is then added and the excess aniline will be distilled off leaving the leuco base 117 is then filtered and washed. The leuco base 117 is then dissolved in dilute HCl and cooled to 0° C. upon which the appropriate amount of lead dioxide is added. Sodium sulphate is added to precipitate lead sulphate, which is removed by filtration. Sodium carbonate is then added to precipitate the carbinol base 119.

From this point the antenna is then isolated as the zinc chloride double salt using acid and zinc chloride (not shown in scheme). The functionalization of cyclen follows the procedure detailed in the production of the quinoline complexes with the exception that the Lanthanides used for chelation will be $Nd^{3+}$ and $Yb^{3+}$. Absorption is expected to be in the range of 620-630 nm, while emission will be at 880, 1064 and 1330 nm for Nd(III) or 980 nm for Yb(III).

EXAMPLE 6

Scheme VI shows a method for producing an NIR lanthanide chelate. The NIR lanthanide chelate may be used for producing NIR images in a tissue transparent window. The NIR lanthanide chelate may be used in combination with fluorescence. The NIR lanthanide chelate has the following general structure:

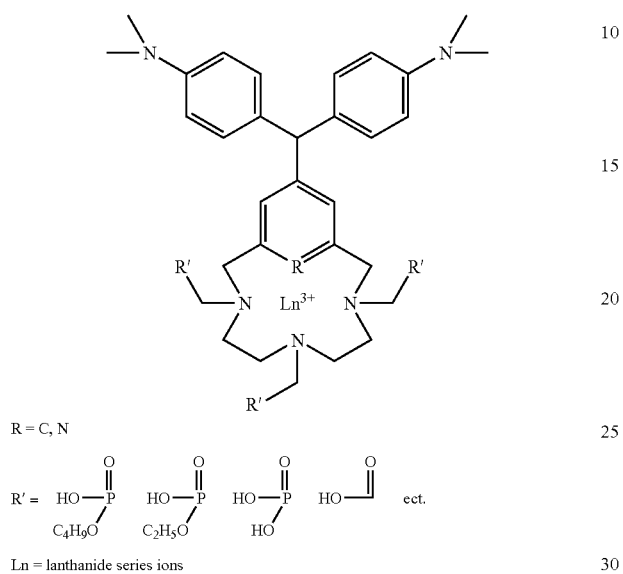

R = C, N

R' = HO—P(=O)(OC$_4$H$_9$)—, HO—P(=O)(OC$_2$H$_5$)—, HO—P(=O)(OH)—, HO—C(=O)— ect.

Ln = lanthanide series ions

The following process may be used to make 13-[Bis-(4-dimethylamino-phenyl)-methyl]-3,9-bis-phosphonomethyl-3,6,9-triaza-bicyclo[9.3.1]pentadeca-1(14),11(15),12-trien-6-yl}-acetic acid 138, wherein R is C, R' is a phosphoester and R" is a carboxylate.

Scheme VI

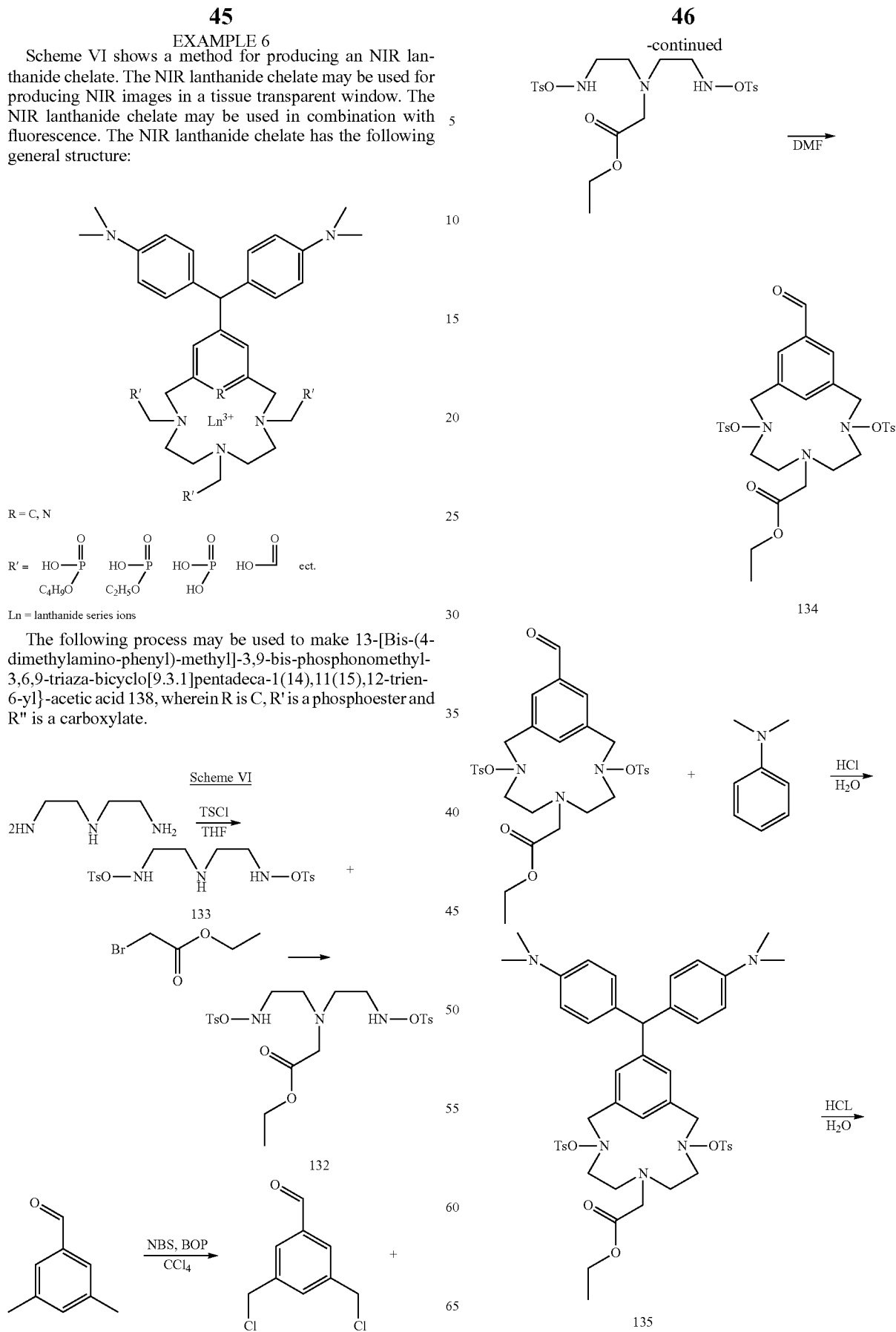

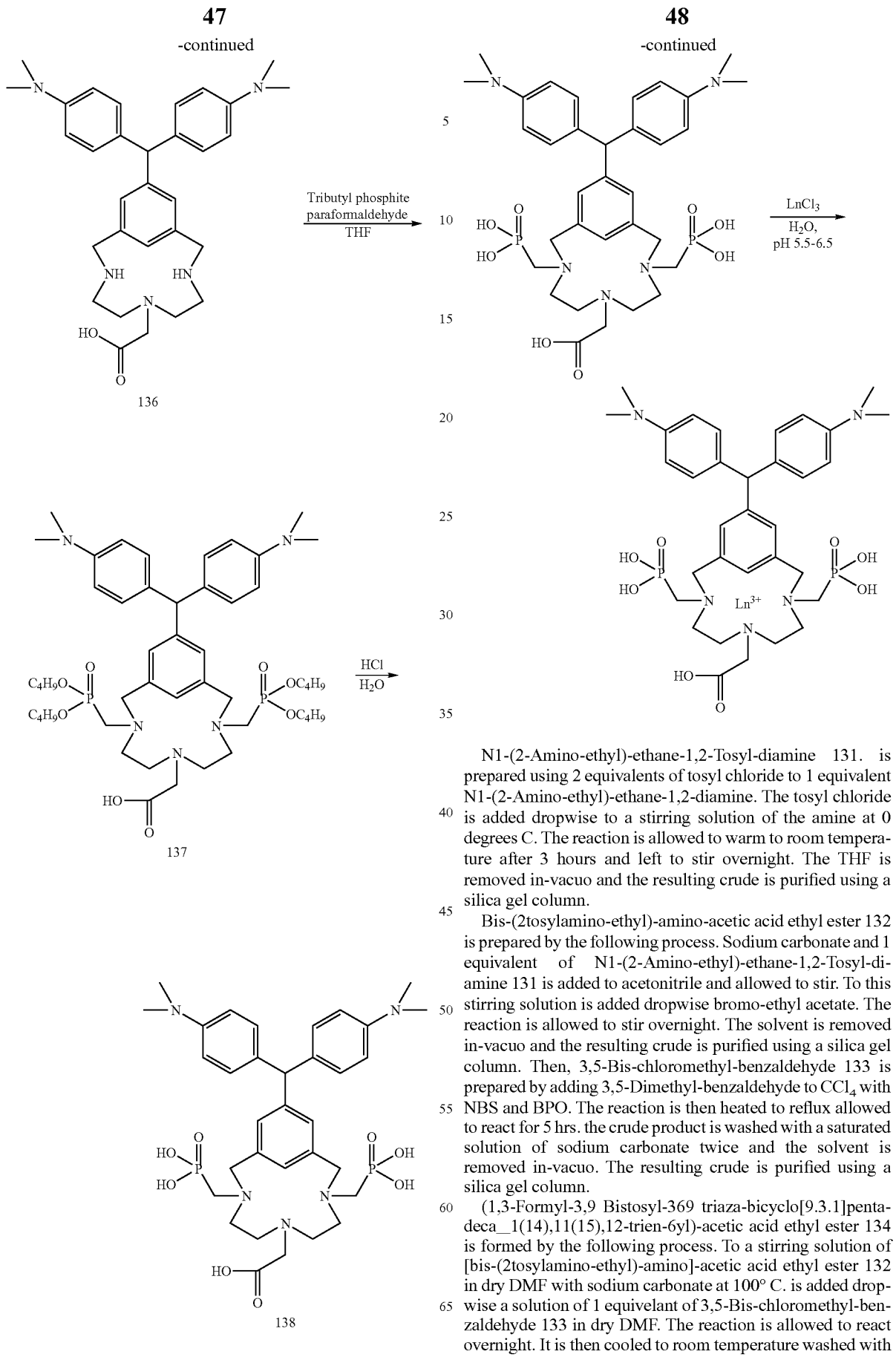

N1-(2-Amino-ethyl)-ethane-1,2-Tosyl-diamine 131. is prepared using 2 equivalents of tosyl chloride to 1 equivalent N1-(2-Amino-ethyl)-ethane-1,2-diamine. The tosyl chloride is added dropwise to a stirring solution of the amine at 0 degrees C. The reaction is allowed to warm to room temperature after 3 hours and left to stir overnight. The THF is removed in-vacuo and the resulting crude is purified using a silica gel column.

Bis-(2tosylamino-ethyl)-amino-acetic acid ethyl ester 132 is prepared by the following process. Sodium carbonate and 1 equivalent of N1-(2-Amino-ethyl)-ethane-1,2-Tosyl-diamine 131 is added to acetonitrile and allowed to stir. To this stirring solution is added dropwise bromo-ethyl acetate. The reaction is allowed to stir overnight. The solvent is removed in-vacuo and the resulting crude is purified using a silica gel column. Then, 3,5-Bis-chloromethyl-benzaldehyde 133 is prepared by adding 3,5-Dimethyl-benzaldehyde to $CCl_4$ with NBS and BPO. The reaction is then heated to reflux allowed to react for 5 hrs. the crude product is washed with a saturated solution of sodium carbonate twice and the solvent is removed in-vacuo. The resulting crude is purified using a silica gel column.

(1,3-Formyl-3,9 Bistosyl-369 triaza-bicyclo[9.3.1]pentadeca_1(14),11(15),12-trien-6yl)-acetic acid ethyl ester 134 is formed by the following process. To a stirring solution of [bis-(2tosylamino-ethyl)-amino]-acetic acid ethyl ester 132 in dry DMF with sodium carbonate at 100° C. is added dropwise a solution of 1 equivalent of 3,5-Bis-chloromethyl-benzaldehyde 133 in dry DMF. The reaction is allowed to react overnight. It is then cooled to room temperature washed with NaOH, dried with sodium sulfate, and rotovaped. the final complex will be purified by recrystallization in acetone.

{13-[bis-(4-dimethylamino-phenyl)-methyl]-3,9-bis tosyl-3,6,9-triaza-bicyclo[9.3.1]pentadeca-1(1(15),12 trien-6yl}-acetic acid ethyl ester 135 is produced by making a 1:1 mixture of dimethyl aniline and (1,3-Formyl-3,9 Bistosyl-369 triaza-bicyclo[9.3.1]pentadeca__1(14),11(15),12-trien-6yl)-acetic acid ethyl ester 134 and adding to a dilute HCl solution and heated to reflux and allowed to react overnight.

{13-[bis-(4-dimethylamino-phenyl)-methyl-3,6,9-triaza-bicyclo[9.3.1]pentadeca-1(1(15),12 trien-6yl}-acetic acid 136 is formed by adding to the crude above conc. HCl and the reaction is allowed to continue for 3 days under reflux. the HCl is removed by aziotropic distillation. The resulting crude is purified by silica gel column chromatography.

[13-[Bis-(4-dimethylamino-phenyl)-methyl]-3,9-bis-(dibutoxy-phosphorylmethyl)-3,6,9-triaza-bicyclo[9.3.1] pentadeca-[(14),11(15),12-trien-6-yl]-acetic acid 137 is formed by adding 2.15 equivalents of paraformaldehyde to 1 equivalent {13-[bis-(4-dimethylamino-phenyl)-methyl-3,6, 9-triaza-bicyclo[9.3.1]pentadeca-1(1(15),12 trien-6yl}-acetic acid 136 in dry THF. When the solvent becomes clear 2.15 equivalents of tributyl phosphite are added and the reaction is allowed to stir at room temp. for 2 days. The reaction is then rotovaped to remove the solvent and the resulting crude is heated under vacuume to remove butanol.

Finally, {13-[Bis-(4-dimethylamino-phenyl)-methyl]-3,9-bis-phosphonomethyl-3,6,9-triaza-bicyclo[9.3.1]pentadeca-1(14),11(15),12-trien-6-yl}-acetic acid 138 is prepared by the following process. A solution of [13-[Bis-(4-dimethylamino-phenyl)-methyl]-3,9-bis-(dibutoxy-phosphorylmethyl)-3,6,9-triaza-bicyclo[9.3.1]pentadeca-[(14),11(15),12-trien-6-yl]-acetic acid 137 in 6M HCl is brought to reflux and allowed to stir for 3 days. The HCl is removed by aziotropic distillation and the product is lyophilized.

Adding the chelating ion is accomplished by similar techniques as described in the previous examples.

EXAMPLE 7

Using the unique chemistry described previously and shown in Scheme II, a trifunctional ligand is prepared. Then, using Scheme VII, a new bimetallic complex is prepared.

Scheme VII

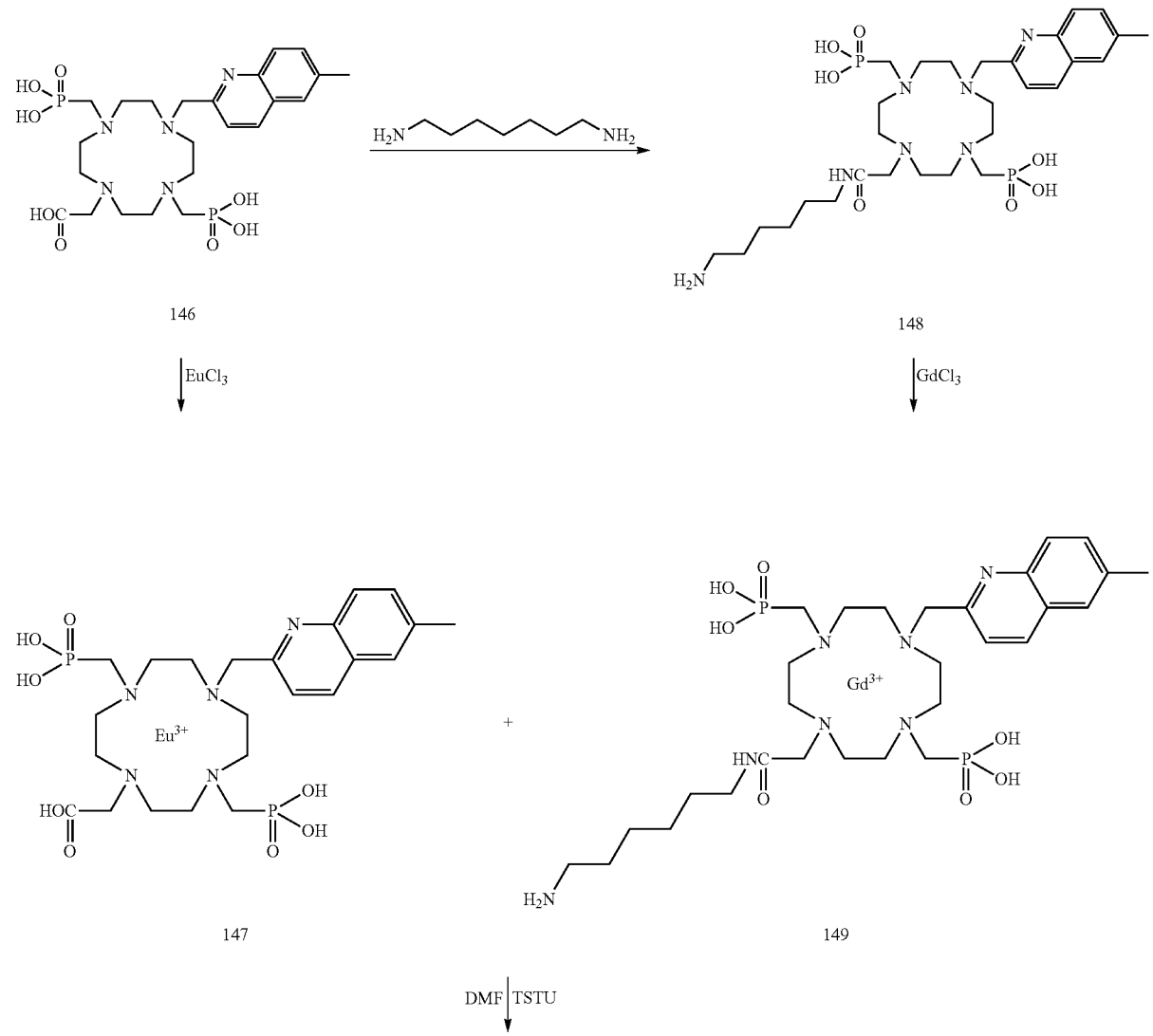

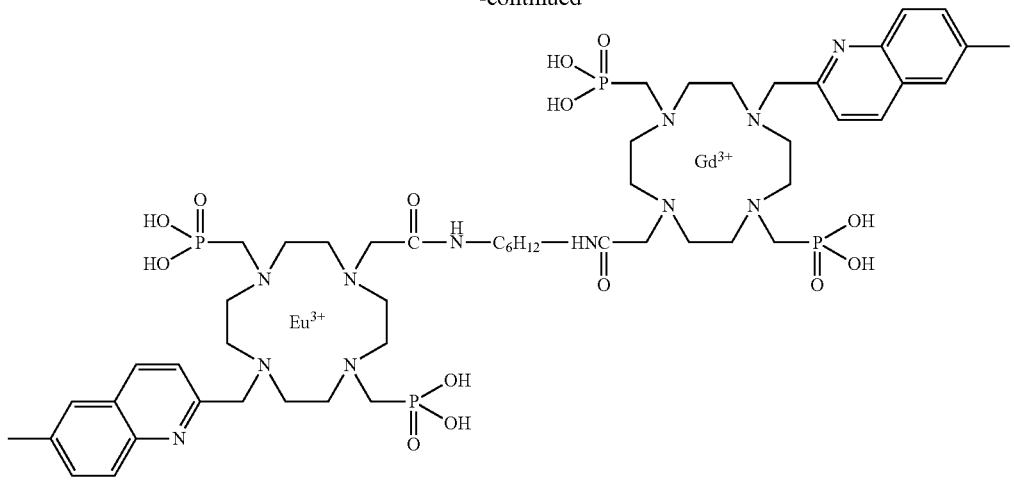

150

The bimetallic complex is synthesized by first forming Ln-1-(2-methylene-6-methyl quinoline)-4,10 Bis(methylene-phosphonic acid)-7-(acetic acid)-1,4,7,10-tetraazacyclododecane 147. To 50 mL of nano-pure water, 0.500 grams of 1-(2-methylene-6-methyl quinoline)-4,10 Bis(methylene-phosphonic acid)-7-(acetic acid)-1,4,7,10-tetraazacyclododecane 146 was added and allowed to dissolve. Upon complete dissolution, the pH was adjusted to 6.5 via a small addition of 1N KOH solution. When the pH stabilized, a solution of $LnCl_3$ was slowly added (1 equivalent by mass) and the pH was maintained around 6 with the KOH. After complete addition, the solution was lyophilized. Complexation was monitored with HPLC and metal content determined by ICP.

Next 1-(2-methylene-6-methyl quinoline)-4,10 Bis(methylene-phosphonic acid)-(N-hexylamine)-1,4,7,10-tetraazacyclododecane 148 is formed by the following process. To a stirring mixture of 1-(2-methylene-6-methyl quinoline)-4,10 Bis(methylene-phosphonic acid)-7-(acetic acid)-1,4,7,10-tetraazacyclododecane and O—(N-Succinimidyl)-N,N,N',N'-Tetramethyluronium tetrafluoroborate (TSTU) (1 equivalent of each) in a water-dioxane solution, a mixture of 1,6 diaminohexane and one equivalent of triethyl amine was added slowly via cannula. The resulting reaction mixture was allowed to stir at room temperature under positive $N_2$ pressure for 4 hours. The desired product was isolated via chloroform:ammonium hydroxide washes and lyophilized.

Then, Ln-1-(2-methylene-6-methyl quinoline)-4,10 Bis(methylene-phosphonic acid)-(N-hexylamine)-1,4,7,10-tetraazacyclododecane 149 is formed as following. To 50 mL of nano-pure water, 0.500 grams of 1-(2-methylene-6-methyl quinoline)-4,10 Bis(methylene-phosphonic acid)-(N-hexylamine)-1,4,7,10-tetraazacyclododecane 148 was added and allowed to dissolve. Upon complete dissolution, the pH was adjusted to 6.5 via a small addition of 1N KOH solution. When the pH stabilized, a solution of $LnCl_3$ was slowly added (1 equivalent by mass) and the pH was maintained around 6 with the KOH. After complete addition, the solution was lyophilized. Complexation was monitored with HPLC and metal content determined by inductively coupled plasma spectrometry (ICP).

Finally, the bimetallic complex Bis[Ln-bis-1-(2-methylene-6-methyl quinoline)-4,10 Bis(methylene-phosphonic acid-1,4,7,10-tetraazacyclododecane])-N-hexyldiamide 150 is produced as follows. To a stirring mixture of Ln-1-(2-methylene-6-methyl quinoline)-4,10 Bis(methylene-phosphonic acid)-7-(acetic acid)-1,4,7,10-tetraazacyclododecane 147 and O—(N-Succinimidyl)-N,N,N',N'-Tetramethyluronium tetrafluoroborate (TSTU) (1 equivalent of each) in a water-dioxane solution, a mixture of Ln-1-(2-methylene-6-methyl quinoline)-4,10 Bis(methylene-phosphonic acid)-(N-hexylamine)-1,4,7,10-tetraazacyclododecane 149 and one equivalent of triethyl amine was added slowly via canula. The resulting reaction mixture was allowed to stir at room temperature under positive $N_2$ pressure for 12 hours. The desired product was isolated via chloroform:ammonium hydroxide washes, filtered through dialysis tubing and microfilters, and lyophilized. Conjugation was monitored via HPLC.

The bimetallic complex is tested as with all of the previous agents. Parameters include; a) optical and NMR spectral properties, b) stability, c) cellular uptake, d) cytotoxicity and e) biodistribution. The bimetallic complex will be evaluated as a bi-modal (fluorescence and MR) imaging agent.

EXAMPLE 8

In an effort to demonstrate long blood half-life, large MR signatures, and disease specificity PEG and PEG-PL are used as synthetic polymeric carriers for the cyclen-based lanthanide chelates.

First, 5 grams of MPEG 5000 was dissolved in 400 mL of dioxane and heated to 90° C. To this mixture, 1.2 g of succinic anhydride and 0.1 g of N,N'-dimethylaminopyridine were added and the mixture was reacted at 110° C. for 7 hours. Next, the solute was concentrated in-vacuo and filtered through a small celite column. To the mother-liquor, 10 mL of EtOAc and 50 mL ether was then added to precipitate the desired PEG disuccinate. The product was further purified by passage through a Sephadex G-25 column.

The preparation of PEG bound Ln-QM-CTMC (PEG-Gd-QM-CTMC) 151 as shown below is performed using the following process.

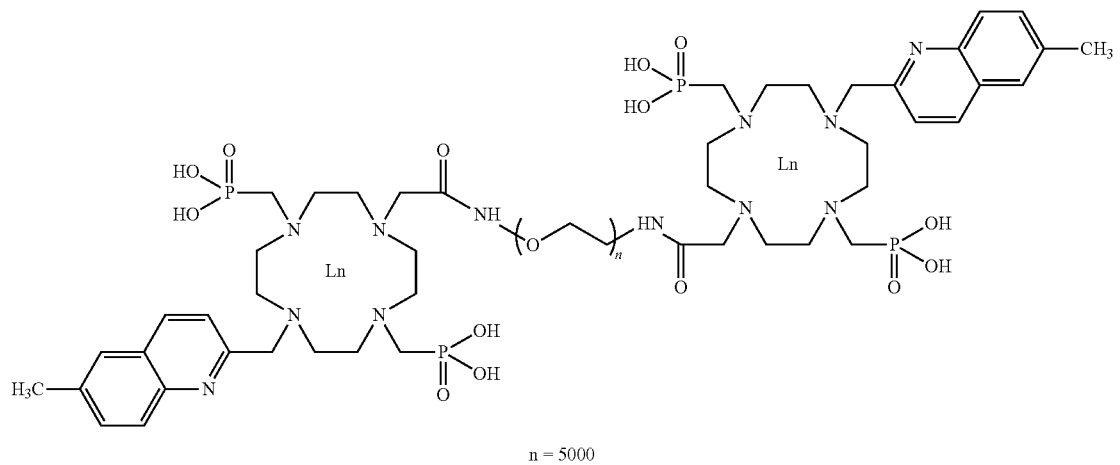

151 n = 5000

To an aqueous stirring solution of MPEG5000 disuccinate (5 mM) at pH 8.5, 10 equivalents of Ln-1-(2-methylene-6-methyl quinoline)-4,10 Bis(methylene-phosphonic acid)-(N-hexylamine)-1,4,7,10-tetraazacyclododecane was added and allowed to react for 3 hours. The products were purified via ultra-filtration and finally passed through a Sephadex A-25 column, which was preequilabrated with water.

As shown below, PEG-Polylysine (PL) bound Ln-QM-CTMC (PEG-PL-Ln-QM-CTMC) 155 is prepared by the following method.

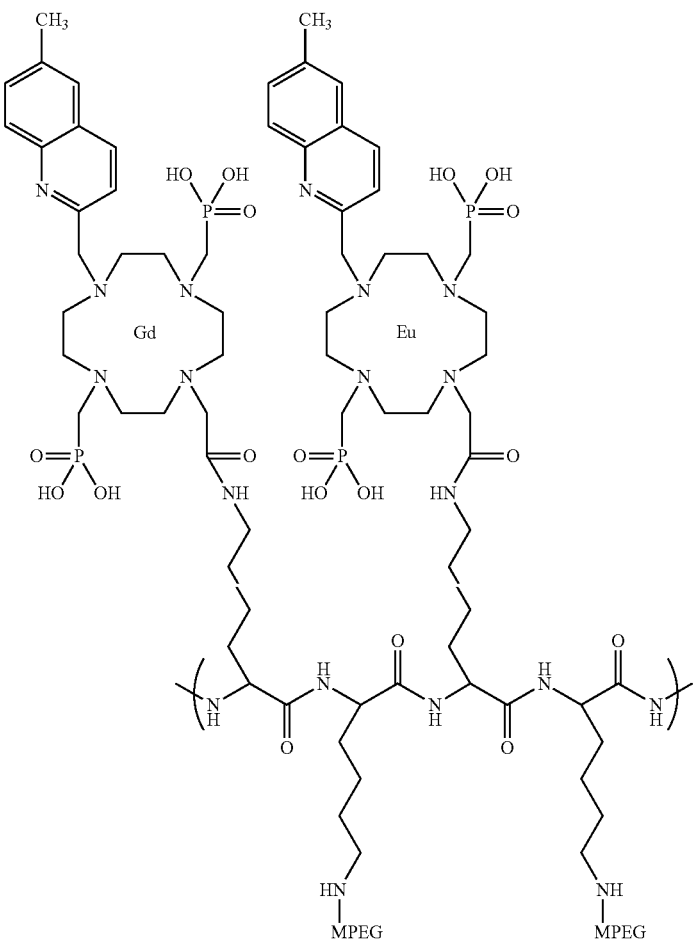

155

To a stirring 25 mM solution of PL (25 KD), 5 mM (equivalent) activated MPEG 5000 was added and allowed to react at room temperature for 1 hour at pH 8.5. This will substitute approximately 30% of the available amino groups on PL. The remaining amino groups were substituted with the succinate ester of Ln-QM-CTMC via aqueous coupling, pH 8.5 (5 molar excess). The products were purified via ultra-filtration and finally passed through a Sephadex A-25 column, which was preequilabrated with water.

The size of the contrast agent was determined via gel filtration, (1×40 cm Ultragel AcA34 column) precalibrated with protein molecular weight markers. Laser light scattering size determinations will also be performed with an N4MD device by using sample particle-size distribution analysis.

Although the present invention has been disclosed in terms of a preferred embodiment, it will be understood that numerous additional modifications and variations could be made thereto without departing from the scope of the invention as defined by the following claims:

We claim:

1. A method for delivering an agent to a sample of cells, comprising:
   (a) providing a compound the following formula:

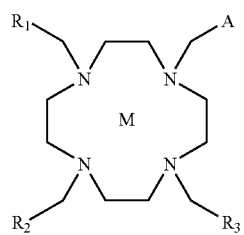

wherein:

M is a chelating ion selected from the group consisting of gallium (Ga), copper (Cu), nickel (Ni), indium (In), technetium (Tc), yttrium (Y) and lanthanide (Ln) series ions;

$R_1$ and $R_3$ are, independently,

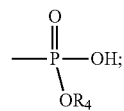

$R_2$ is

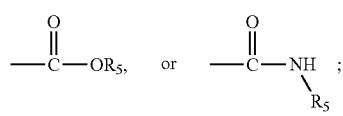

$R_4$ is H, $CH_3$, $C_2H_5$, $C_3H_7$, $C_4H_9$, $C_5H_{11}$, $C_6H_{13}$;

A is a sensitizer; and $R_5$ is:

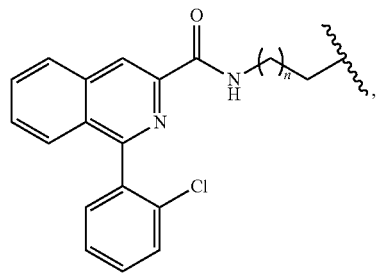

with n is 0-10; and
   (b) introducing the conjugate to the sample of cells.

2. The method of claim 1, wherein A is selected from the group consisting of:

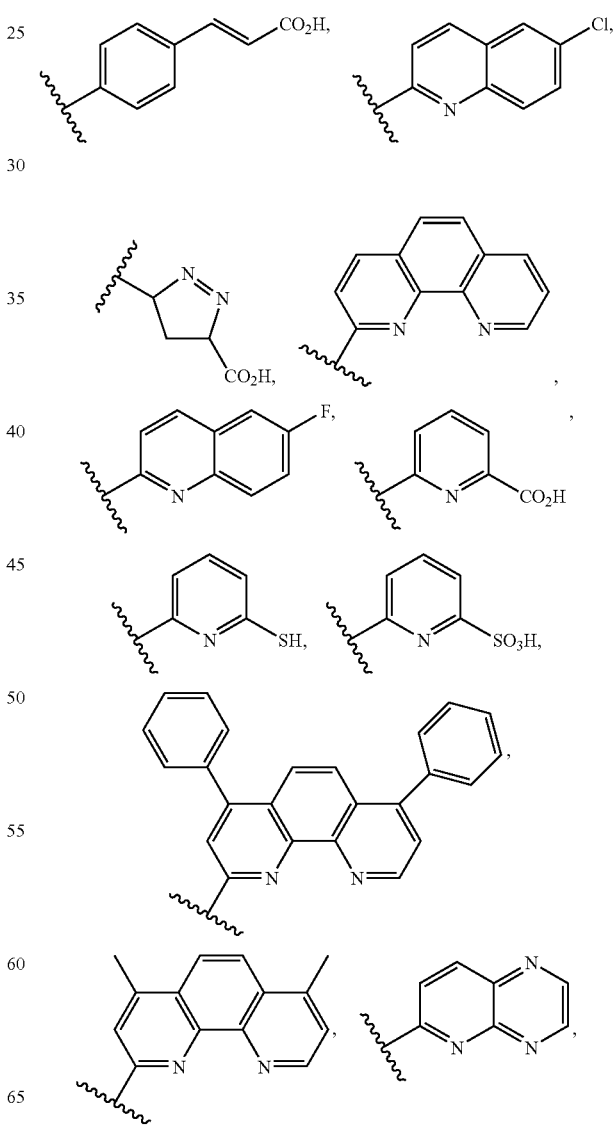

-continued
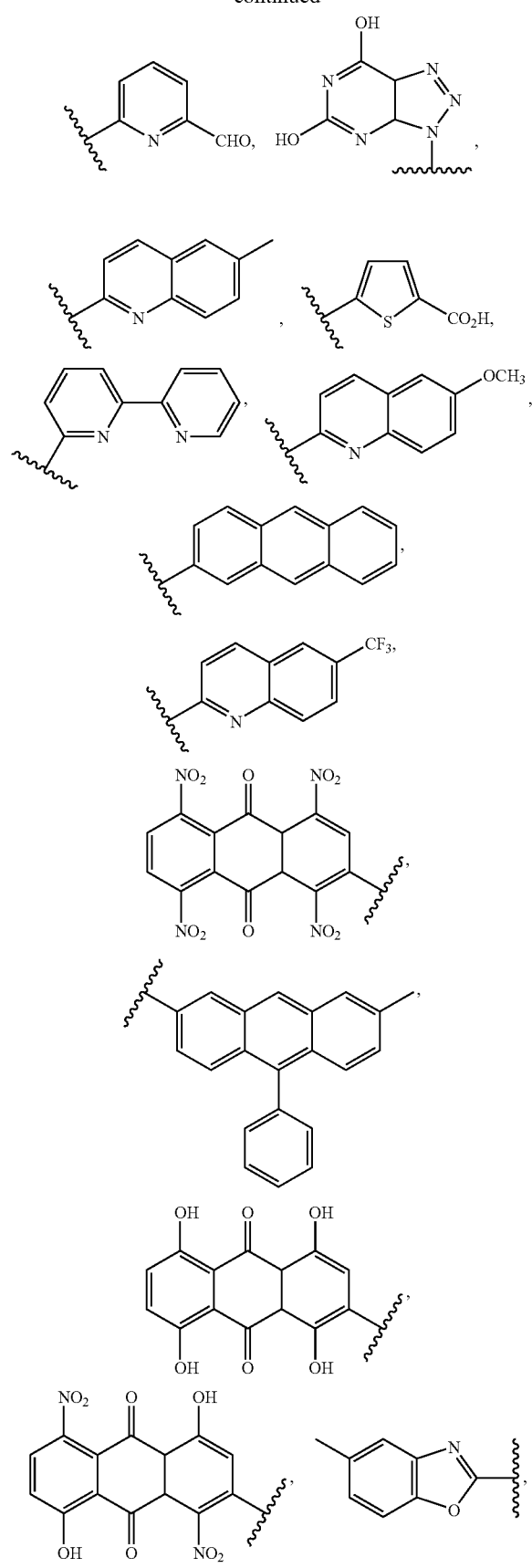
-continued
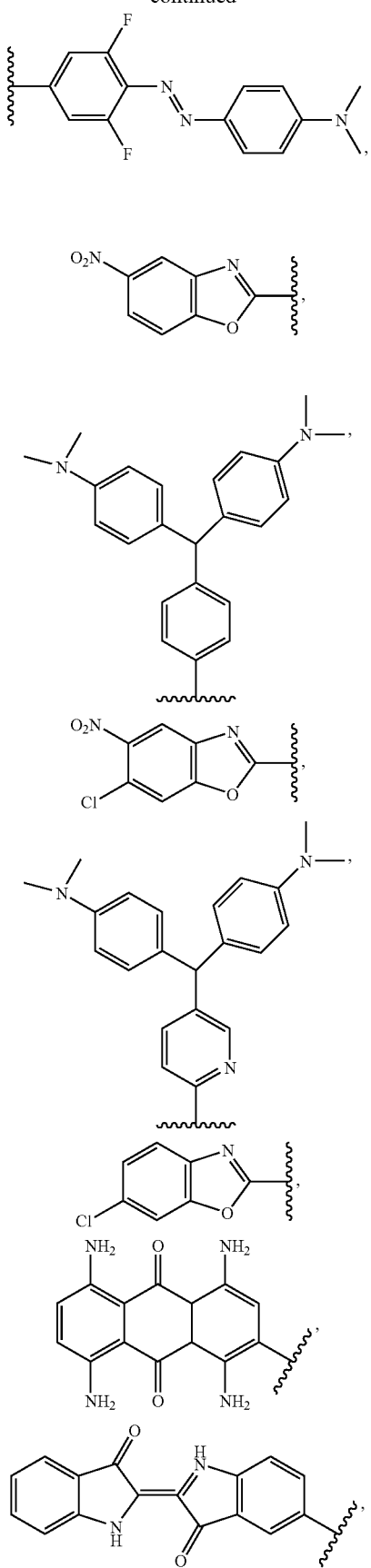

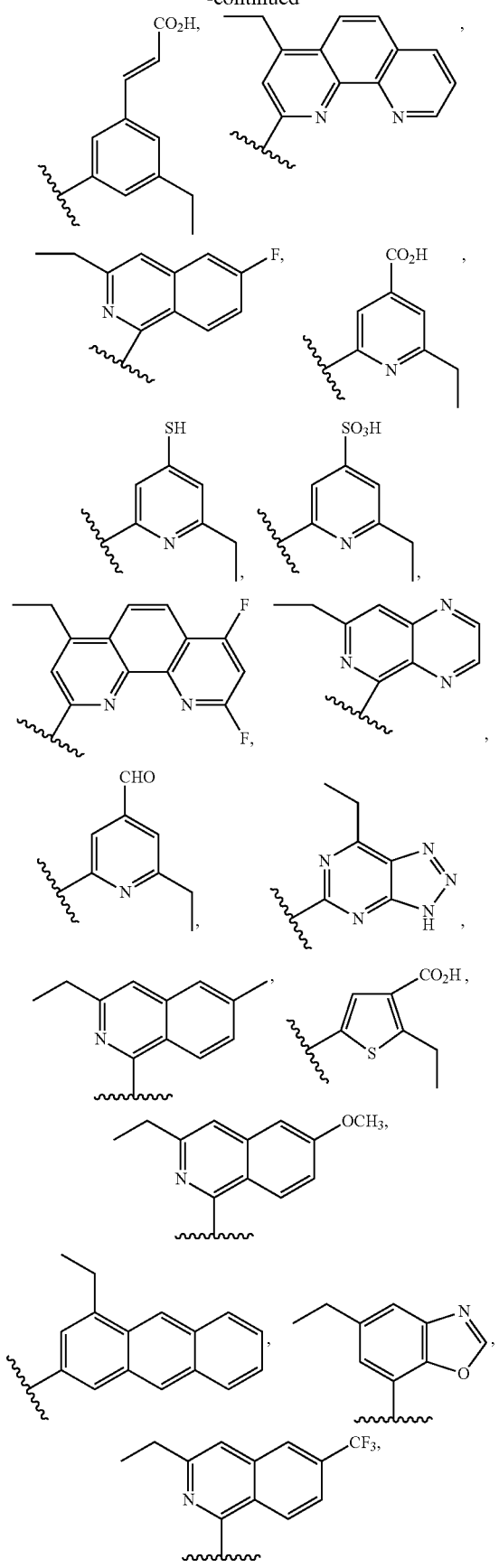
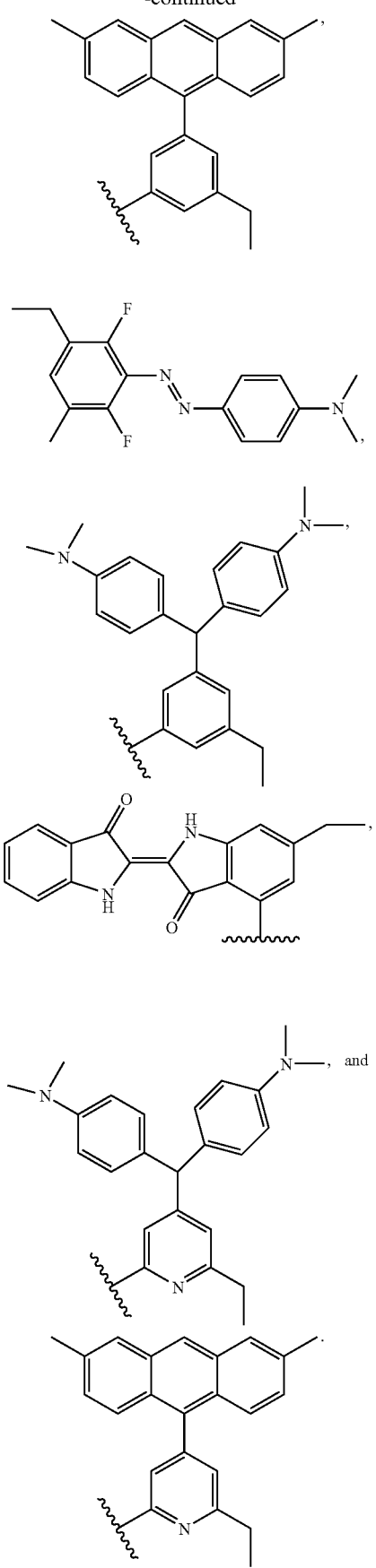

3. The method of claim 1, wherein A is

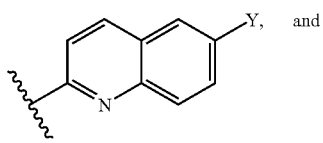

Y is F, Cl, CH₃, OCH₃, CF₃, or NO₂.

4. The method of claim 1, wherein M is a lanthanide series ion.

5. The method of claim 1, wherein the lanthanide series ion is selected from the group consisting of gadolinium (Gd), terbium (Th), europium (Eu), ytterbium (Yb), neodymium (Nd), lutetium (Lu), erbium (Er) ions.

6. The method of claim 1, wherein step (a) provides the following compound:

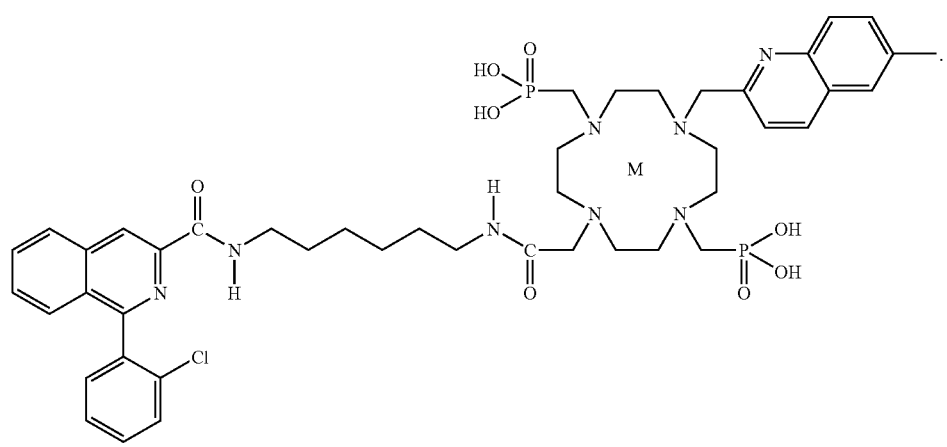

7. A method for multi-modal imaging a sample of cells comprises, (a) administering to said sample of cells an effective amount of a cyclen-based chelate of the Formula (I):

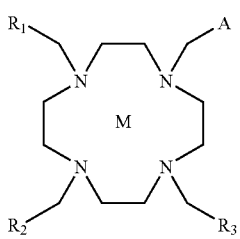

wherein:

M is a chelating ion selected from the group comprising, gallium (Ga), copper (Cu), nickel (Ni), indium (In), technetium (Tc), yttrium (Y) and lanthanide (Ln) series ion;

$R_1$ and $R_3$ are, independently,

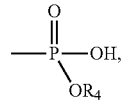

$R_2$ is

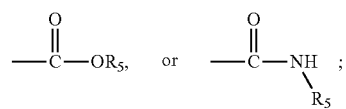

$R_4$ is H, CH₃, C₂H₅, C₃H₇, C₄H₉, C₅H₁₁, C₆H₁₃;

A is a photo-stable sensitizer;

$R_5$ is a compound of the formula:

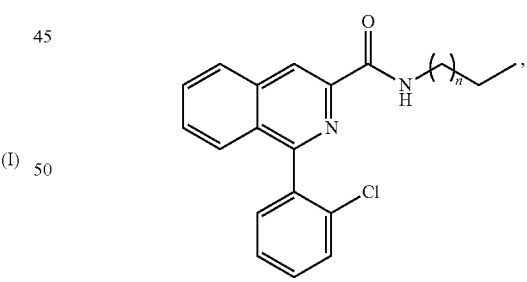

wherein n is 0-10; and (b) detecting a signal from said cyclen-based chelate.

8. The method of claim 7, wherein A is selected from the group consisting of:

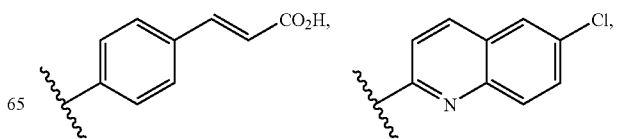

-continued
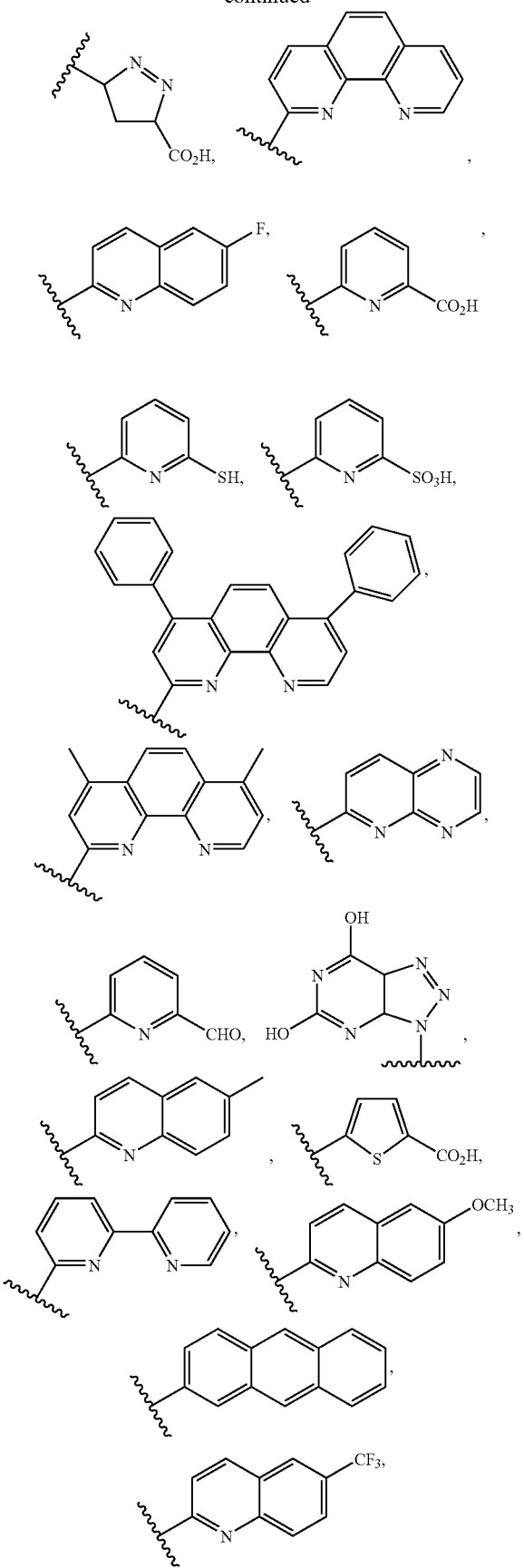
-continued
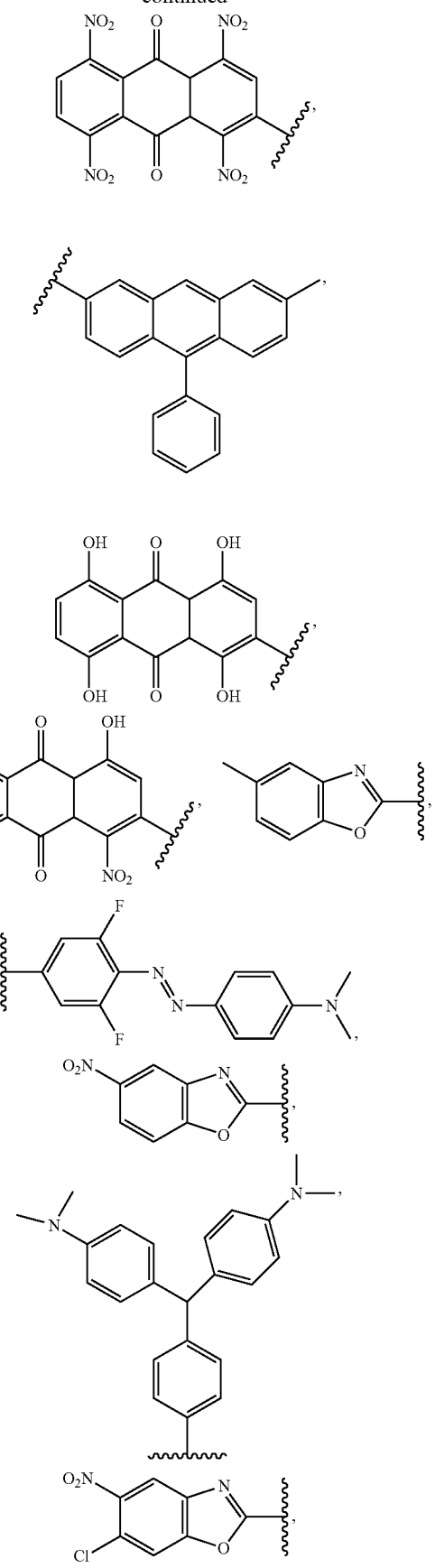

65
-continued
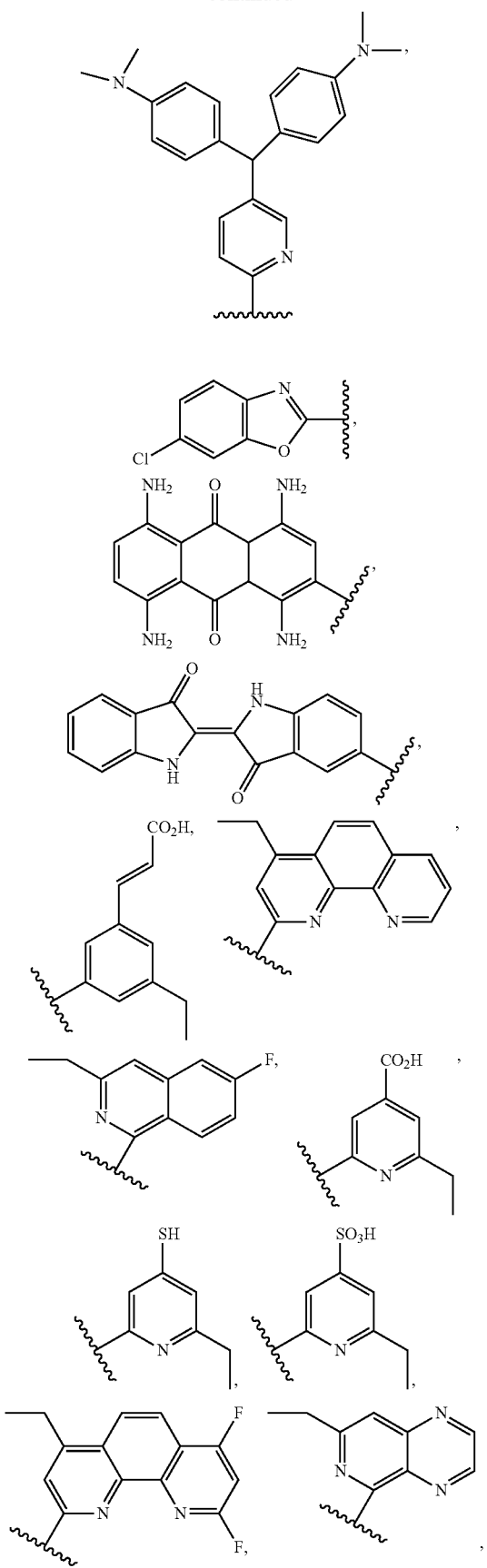
66
-continued
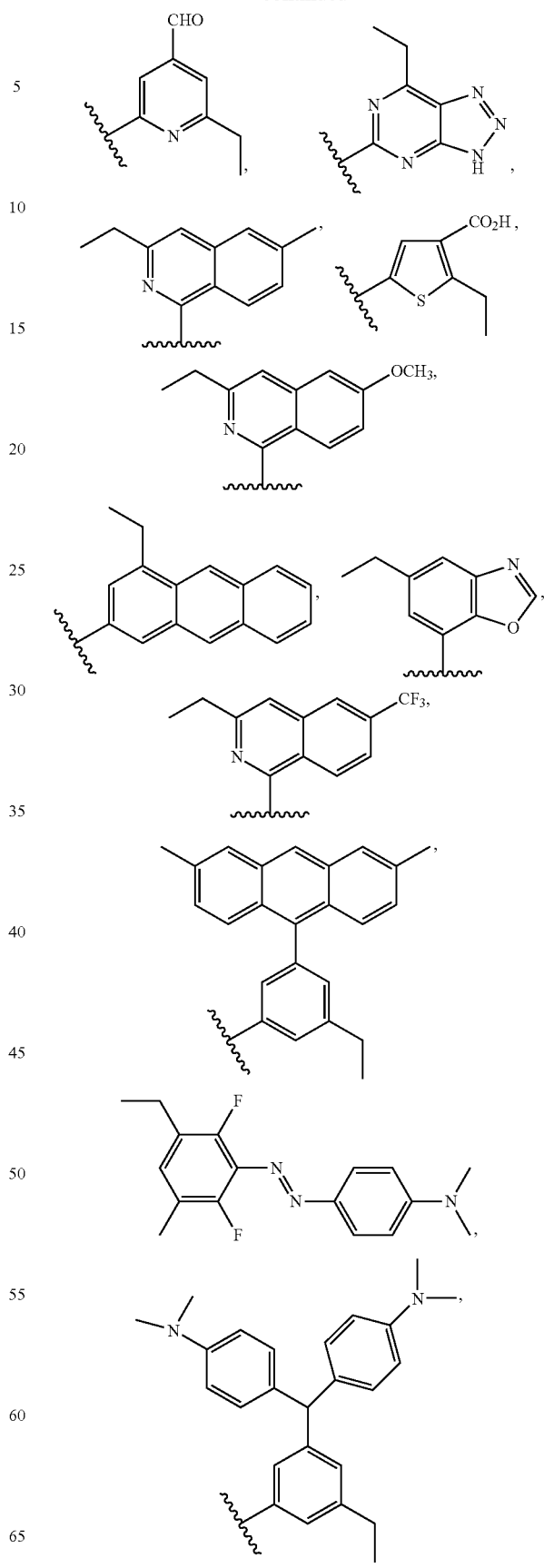

-continued

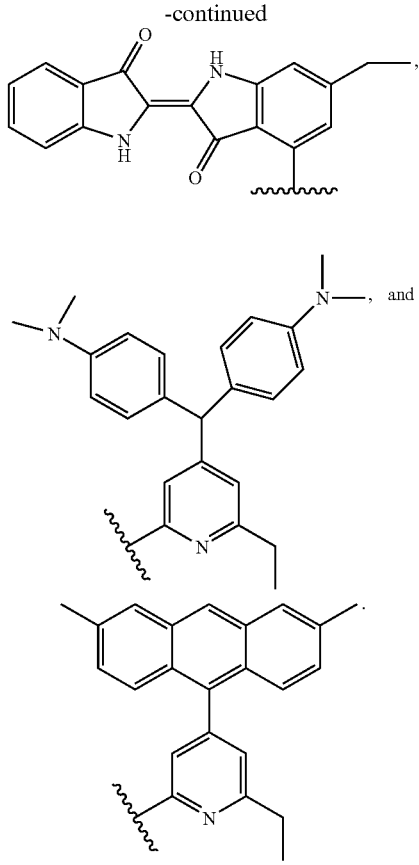

9. The method of claim 7, further comprising:
   administering to said sample of cells an effective amount of a second imaging agent; and
   detecting a second signal from said second imaging agent.

10. The method of claim 9, wherein the administering a second imaging agent step occurs before detecting the first signal.

11. The method of claim 7, further comprising:
    administering to a sample of cells an effective amount of a second imaging agent, the second imaging agent being a cyclen-based chelate of the Formula (I); and
    detecting a second signal from said second imaging agent.

12. The method of claim 7, wherein said sample of cells is a cell line.

13. The method of claim 7, further comprising the step of:
    analyzing said signal to diagnose a disease state.

14. The method of claim 7, wherein said disease state is cancer.

15. The method of claim 7, wherein said disease state is brain cancer or breast cancer.

16. The method of claim 7, wherein the signal is selected from the group comprising a fluorescent image, a MRI image, a NIR image, a PET image, a CT image or an x-ray image.

17. The method of claim 7, wherein the cyclen-based chelate of the Formula (I) comprises a polymeric delivery vehicle binded thereto.

18. The method of claim 17, wherein the polymeric delivery vehicle is at least one of a polyvinyl alcohol delivery vehicle or a polyethylene glycol delivery vehicle.

* * * * *